United States Patent
Sun et al.

(10) Patent No.: US 11,180,720 B2
(45) Date of Patent: Nov. 23, 2021

(54) POLYPEPTIDES HAVING DNASE ACTIVITY

(71) Applicant: Novozymes A/S, Bagsvaerd (DK)

(72) Inventors: Tianqi Sun, Beijing (CN); Klaus Gori, Dyssegaard (DK); Mary Ann Stringer, Bagsvaerd (DK); Jesper Salomon, Holte (DK); Kirk Matthew Schnorr, Holte (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 16/495,147

(22) PCT Filed: Mar. 23, 2018

(86) PCT No.: PCT/CN2018/080156
§ 371 (c)(1),
(2) Date: Sep. 18, 2019

(87) PCT Pub. No.: WO2018/177203
PCT Pub. Date: Apr. 10, 2018

(65) Prior Publication Data
US 2020/0032169 A1    Jan. 30, 2020

(30) Foreign Application Priority Data
Mar. 31, 2017 (EP) .................... 17164340

(51) Int. Cl.
| C11D 3/386 | (2006.01) |
| C11D 3/00 | (2006.01) |
| C11D 11/00 | (2006.01) |
| C12N 9/22 | (2006.01) |
| C12N 15/52 | (2006.01) |

(52) U.S. Cl.
CPC ........ *C11D 3/38636* (2013.01); *C11D 3/0036* (2013.01); *C11D 3/0068* (2013.01); *C11D 3/38663* (2013.01); *C11D 11/0017* (2013.01); *C12N 9/22* (2013.01); *C12N 15/52* (2013.01)

(58) Field of Classification Search
None
See application file for complete search history.

(56) References Cited

U.S. PATENT DOCUMENTS

| 10,081,783 B2 * | 9/2018 | Lant ................ C11D 3/38609 |
| 2017/0152462 A1 | 6/2017 | Baltsen |

FOREIGN PATENT DOCUMENTS

| EP | 2617824 A1 | 7/2013 |
| EP | 3088505 A1 | 11/2016 |
| WO | 2014087011 A1 | 6/2014 |
| WO | 2015155350 A1 | 10/2015 |
| WO | 2016162556 A1 | 10/2016 |
| WO | 2017001471 A1 | 1/2017 |
| WO | 2017001472 A1 | 1/2017 |

OTHER PUBLICATIONS

Traeger et al., "The Genome and Development-Dependent Transcriptomes of Pyronema confluens: A Window inot Fungal Evolution", PLoS Genet 9(9): e1003820 (Year: 2013).*
Martin et al, 2010, EBI Accession No. D5GLX7.
Martin et al, 2010, NCBI Accession No. XP_002841353.1.
Traeger et al, 2013, EBI Accession No. U4LP83.
Traeger et al., 2013, GenBank Accession No. CCX33377.1.

* cited by examiner

*Primary Examiner* — Anand U Desai
(74) *Attorney, Agent, or Firm* — Yoshimi Barron

(57) ABSTRACT

The present invention provides polypeptides having DNase activity and polynucleotides encoding the polypeptides. The invention also provides nucleic acid constructs, vectors, and host cells comprising the polynucleotides as well as methods of producing and using the polypeptides.

28 Claims, 2 Drawing Sheets
Specification includes a Sequence Listing.

SEQUENCE LISTING

```
<160> NUMBER OF SEQ ID NOS: 48

<210> SEQ ID NO 1
<211> LENGTH: 751
<212> TYPE: DNA
<213> ORGANISM: Ascobolus stictoideus
<220> FEATURE:
<221> NAME/KEY: CDS
<222> LOCATION: (1)..(242)
<220> FEATURE:
<221> NAME/KEY: sig_peptide
<222> LOCATION: (1)..(54)
<220> FEATURE:
<221> NAME/KEY: mat_peptide
<222> LOCATION: (55)..(748)
<220> FEATURE:
<221> NAME/KEY: CDS
<222> LOCATION: (310)..(572)
<220> FEATURE:
<221> NAME/KEY: CDS
<222> LOCATION: (639)..(748)

<400> SEQUENCE: 1 atg aag ctc act ttc ctc acc gct ctt gct gcc tct ttg gct ctc acc        48
Met Lys Leu Thr Phe Leu Thr Ala Leu Ala Ala Ser Leu Ala Leu Thr
            -15                 -10                 -5 gct gcc aac cca ctc cca gct cca gct cca cca aac atc cca tcc gct        96
Ala Ala Asn Pro Leu Pro Ala Pro Ala Pro Pro Asn Ile Pro Ser Ala
    -1   1               5                  10 gcc acc gca aag tct gag ctt gct gct ctc ggc acc aga acc agc gat       144
Ala Thr Ala Lys Ser Glu Leu Ala Ala Leu Gly Thr Arg Thr Ser Asp
 15                  20                  25                  30 gcc cct ggt tac tcc cgc gat ctc ttc aac cac tgg atc acc att tct       192
Ala Pro Gly Tyr Ser Arg Asp Leu Phe Asn His Trp Ile Thr Ile Ser
                 35                  40                  45 ggc caa tgc aac acc cgc gag act gtc ctc aag cgt gac gga acc aac       240
Gly Gln Cys Asn Thr Arg Glu Thr Val Leu Lys Arg Asp Gly Thr Asn
             50                  55                  60 gt  gtaagaccac cctcctcctc ctcctacatt gttgcaaaca taaatactaa            292
Val caaaaagccc tctatag t gtc caa gcc tcc aac tgc gct gcc acc tcc gga      343
                      Val Gln Ala Ser Asn Cys Ala Ala Thr Ser Gly
                       65                  70 acc tgg tac tct ccc ttc gat ggc gcc acc tgg acc gcc gcc tcc gac       391
Thr Trp Tyr Ser Pro Phe Asp Gly Ala Thr Trp Thr Ala Ala Ser Asp
 75                  80                  85                  90 ctc gac att gac cac gtt gtc cca ctc tcc aac gcc tgg aag tct gga       439
```

```
Leu Asp Ile Asp His Val Pro Leu Ser Asn Ala Trp Lys Ser Gly
             95                 100                 105 gcc gga act tgg act gct gct cgt cgt caa cag ttc gca aat gac ttg    487
Ala Gly Thr Trp Thr Ala Ala Arg Arg Gln Gln Phe Ala Asn Asp Leu
        110                 115                 120 gtt aac ccc caa ctc att gcc gtt act gat tcg gtc aac cag gcc aag    535
Val Asn Pro Gln Leu Ile Ala Val Thr Asp Ser Val Asn Gln Ala Lys
            125                 130                 135 ggt gat aag tcc cct gat gcc tgg aag cca cca ctt a gtaagttctt       582
Gly Asp Lys Ser Pro Asp Ala Trp Lys Pro Pro Leu
    140                 145                 150 ccccatgat ccatccacat gaaaggattg aattgagata ccaacctttg atatag cc    640
                                                              Thr tct tac tac tgc acc tac gcc agg atg tgg gtt aga gtc aag tat gtt    688
Ser Tyr Tyr Cys Thr Tyr Ala Arg Met Trp Val Arg Val Lys Tyr Val
            155                 160                 165 tac ggc ttg act gtc act gct gct gag aag tcg gct ttg act agc atg    736
Tyr Gly Leu Thr Val Thr Ala Ala Glu Lys Ser Ala Leu Thr Ser Met
        170                 175                 180 ttg aac act tgc tag                                                 751
Leu Asn Thr Cys
    185
```

<210> SEQ ID NO 2
<211> LENGTH: 205
<212> TYPE: PRT
<213> ORGANISM: Ascobolus stictoideus

<400> SEQUENCE: 2

```
Met Lys Leu Thr Phe Leu Thr Ala Leu Ala Ala Ser Leu Ala Leu Thr
            -15                 -10                  -5

Ala Ala Asn Pro Leu Pro Ala Pro Ala Pro Asn Ile Pro Ser Ala
 -1   1               5                  10

Ala Thr Ala Lys Ser Glu Leu Ala Ala Leu Gly Thr Arg Thr Ser Asp
 15              20                  25                      30

Ala Pro Gly Tyr Ser Arg Asp Leu Phe Asn His Trp Ile Thr Ile Ser
                 35                  40                  45

Gly Gln Cys Asn Thr Arg Glu Thr Val Leu Lys Arg Asp Gly Thr Asn
             50                  55                  60

Val Val Gln Ala Ser Asn Cys Ala Ala Thr Ser Gly Thr Trp Tyr Ser
         65                  70                  75

Pro Phe Asp Gly Ala Thr Trp Thr Ala Ala Ser Asp Leu Asp Ile Asp
 80                  85                  90

His Val Pro Leu Ser Asn Ala Trp Lys Ser Gly Ala Gly Thr Trp
 95                 100                 105                 110

Thr Ala Ala Arg Arg Gln Gln Phe Ala Asn Asp Leu Val Asn Pro Gln
                 115                 120                 125

Leu Ile Ala Val Thr Asp Ser Val Asn Gln Ala Lys Gly Asp Lys Ser
             130                 135                 140

Pro Asp Ala Trp Lys Pro Pro Leu Thr Ser Tyr Tyr Cys Thr Tyr Ala
         145                 150                 155

Arg Met Trp Val Arg Val Lys Tyr Val Tyr Gly Leu Thr Val Thr Ala
     160                 165                 170

Ala Glu Lys Ser Ala Leu Thr Ser Met Leu Asn Thr Cys
175                 180                 185
```

<210> SEQ ID NO 3

-continued

```
<211> LENGTH: 187
<212> TYPE: PRT
<213> ORGANISM: Ascobolus stictoideus

<400> SEQUENCE: 3

Asn Pro Leu Pro Ala Pro Ala Pro Pro Asn Ile Pro Ser Ala Ala Thr
1               5                   10                  15

Ala Lys Ser Glu Leu Ala Ala Leu Gly Thr Arg Thr Ser Asp Ala Pro
            20                  25                  30

Gly Tyr Ser Arg Asp Leu Phe Asn His Trp Ile Thr Ile Ser Gly Gln
        35                  40                  45

Cys Asn Thr Arg Glu Thr Val Leu Lys Arg Asp Gly Thr Asn Val Val
50                  55                  60

Gln Ala Ser Asn Cys Ala Ala Thr Ser Gly Thr Trp Tyr Ser Pro Phe
65                  70                  75                  80

Asp Gly Ala Thr Trp Thr Ala Ala Ser Asp Leu Asp Ile Asp His Val
                85                  90                  95

Val Pro Leu Ser Asn Ala Trp Lys Ser Gly Ala Gly Thr Trp Thr Ala
            100                 105                 110

Ala Arg Arg Gln Gln Phe Ala Asn Asp Leu Val Asn Pro Gln Leu Ile
        115                 120                 125

Ala Val Thr Asp Ser Val Asn Gln Ala Lys Gly Asp Lys Ser Pro Asp
    130                 135                 140

Ala Trp Lys Pro Pro Leu Thr Ser Tyr Tyr Cys Thr Tyr Ala Arg Met
145                 150                 155                 160

Trp Val Arg Val Lys Tyr Val Tyr Gly Leu Thr Val Thr Ala Ala Glu
                165                 170                 175

Lys Ser Ala Leu Thr Ser Met Leu Asn Thr Cys
            180                 185

<210> SEQ ID NO 4
<211> LENGTH: 973
<212> TYPE: DNA
<213> ORGANISM: Urnula sp-56769
<220> FEATURE:
<221> NAME/KEY: CDS
<222> LOCATION: (1)..(227)
<220> FEATURE:
<221> NAME/KEY: sig_peptide
<222> LOCATION: (1)..(48)
<220> FEATURE:
<221> NAME/KEY: mat_peptide
<222> LOCATION: (49)..(970)
<220> FEATURE:
<221> NAME/KEY: CDS
<222> LOCATION: (310)..(433)
<220> FEATURE:
<221> NAME/KEY: CDS
<222> LOCATION: (493)..(549)
<220> FEATURE:
<221> NAME/KEY: CDS
<222> LOCATION: (614)..(670)
<220> FEATURE:
<221> NAME/KEY: CDS
<222> LOCATION: (741)..(804)
<220> FEATURE:
<221> NAME/KEY: CDS
<222> LOCATION: (861)..(970)

<400> SEQUENCE: 4 atg aag ttt tcc acc gtt ctt cct ctc gtg ttc act ctg gtc gcg ggg    48
Met Lys Phe Ser Thr Val Leu Pro Leu Val Phe Thr Leu Val Ala Gly
    -15                 -10                 -5                  -1 gca cca gcg cca aca ccg atc gtc gac caa gct gca atc gag aag cgt    96
```

```
Ala Pro Ala Pro Thr Pro Ile Val Asp Gln Ala Ala Ile Glu Lys Arg
1               5                   10                  15 ctg cca aca ggc att ccc acc gcc gct acc gca aag acc ttg ttg gct    144
Leu Pro Thr Gly Ile Pro Thr Ala Ala Thr Ala Lys Thr Leu Leu Ala
            20                  25                  30 ggg ttg ggc acc aga act act gat gcg act gga tac gac cgg gac ctg    192
Gly Leu Gly Thr Arg Thr Thr Asp Ala Thr Gly Tyr Asp Arg Asp Leu
                35                  40                  45 ttc ccg cac tgg atc acc att tct gga aac tgc aa  gtgcgttttg         237
Phe Pro His Trp Ile Thr Ile Ser Gly Asn Cys Asn
    50                  55                  60 aacccagcct tagattatct accaaatcag tatttcttgt gtatcaatca ttctaagacg  297
tatggattac ag c acc cgt gag acg gtc tta aac cgt gac ggc acg aac    346
               Thr Arg Glu Thr Val Leu Asn Arg Asp Gly Thr Asn
                                65                  70 ctt gat att ggc acc gat tgt tac cct gac agc ggc acc tgg gtc agt    394
Leu Asp Ile Gly Thr Asp Cys Tyr Pro Asp Ser Gly Thr Trp Val Ser
        75                  80                  85 cct tat gat gga gct acc tgg act gcg gct tcg gat gtg gtatgtttcc    443
Pro Tyr Asp Gly Ala Thr Trp Thr Ala Ala Ser Asp Val
    90                  95                  100 aacaacttaa tacgcataga attcacatac taatactcca tttaactag gat atc gac  501
                                                        Asp Ile Asp cat gtt gtg ccg ctg tct gaa gct tgg aaa gct ggt gcg aat gca tgg    549
His Val Val Pro Leu Ser Glu Ala Trp Lys Ala Gly Ala Asn Ala Trp
    105                 110                 115                 120 gtacttagca caatatctct actcacacaa ttagctcata ctaatacact tcatcttcct  609 gaag act act gcc cag cgc cag gca ttc gcc aat gac ctc acc aat cct   658
     Thr Thr Ala Gln Arg Gln Ala Phe Ala Asn Asp Leu Thr Asn Pro
                 125                 130                 135 caa tta gtc gct gtgagtttct ttcccttcac agacaggtaa acaacctgga        710
Gln Leu Val Ala aactcaggga tgctgattga acgtgttcag gtc acg gat aat gtc aac tcc gcc   764
                                Val Thr Asp Asn Val Asn Ser Ala
                                            140                 145 aag ggt gat aag acc ccc gac ctt tgg aag ccc ccg ttg a gtatgttttc   814
Lys Gly Asp Lys Thr Pro Asp Leu Trp Lys Pro Pro Leu
        150                 155                 160 ctcttgtacg acatgcttgg aatcttacta accacgttta taacag cc  tcg ttc     868
                                                     Thr Ser Phe cac tgc acc tat gcc cgg atg tac gtc aag gtc aag agc gtc tac agc    916
His Cys Thr Tyr Ala Arg Met Tyr Val Lys Val Lys Ser Val Tyr Ser
    165                 170                 175 ctc acg gtt aag tct gct gag agg acg gcc ctt act tct atg ttg gct    964
Leu Thr Val Lys Ser Ala Glu Arg Thr Ala Leu Thr Ser Met Leu Ala
180                 185                 190                 195 act tgt taa                                                        973
Thr Cys

<210> SEQ ID NO 5
<211> LENGTH: 213
<212> TYPE: PRT
<213> ORGANISM: Urnula sp-56769

<400> SEQUENCE: 5

Met Lys Phe Ser Thr Val Leu Pro Leu Val Phe Thr Leu Val Ala Gly
        -15                 -10                 -5              -1

Ala Pro Ala Pro Thr Pro Ile Val Asp Gln Ala Ala Ile Glu Lys Arg
```

-continued

```
                1               5                   10                  15
            Leu Pro Thr Gly Ile Pro Thr Ala Ala Thr Ala Lys Thr Leu Leu Ala
                            20                  25                  30
            Gly Leu Gly Thr Arg Thr Thr Asp Ala Thr Gly Tyr Asp Arg Asp Leu
                            35                  40                  45
            Phe Pro His Trp Ile Thr Ile Ser Gly Asn Cys Asn Thr Arg Glu Thr
                            50                  55                  60
            Val Leu Asn Arg Asp Gly Thr Asn Leu Asp Ile Gly Thr Asp Cys Tyr
             65                 70                  75                  80
            Pro Asp Ser Gly Thr Trp Val Ser Pro Tyr Asp Gly Ala Thr Trp Thr
                            85                  90                  95
            Ala Ala Ser Asp Val Asp Ile Asp His Val Val Pro Leu Ser Glu Ala
                            100                 105                 110
            Trp Lys Ala Gly Ala Asn Ala Trp Thr Thr Ala Gln Arg Gln Ala Phe
                            115                 120                 125
            Ala Asn Asp Leu Thr Asn Pro Gln Leu Val Ala Val Thr Asp Asn Val
                            130                 135                 140
            Asn Ser Ala Lys Gly Asp Lys Thr Pro Asp Leu Trp Lys Pro Pro Leu
            145                 150                 155                 160
            Thr Ser Phe His Cys Thr Tyr Ala Arg Met Tyr Val Lys Val Lys Ser
                            165                 170                 175
            Val Tyr Ser Leu Thr Val Lys Ser Ala Glu Arg Thr Ala Leu Thr Ser
                            180                 185                 190
            Met Leu Ala Thr Cys
                            195

<210> SEQ ID NO 6
<211> LENGTH: 197
<212> TYPE: PRT
<213> ORGANISM: Urnula sp-56769

<400> SEQUENCE: 6

Ala Pro Ala Pro Thr Pro Ile Val Asp Gln Ala Ala Ile Glu Lys Arg
             1               5                   10                  15
            Leu Pro Thr Gly Ile Pro Thr Ala Ala Thr Ala Lys Thr Leu Leu Ala
                            20                  25                  30
            Gly Leu Gly Thr Arg Thr Thr Asp Ala Thr Gly Tyr Asp Arg Asp Leu
                            35                  40                  45
            Phe Pro His Trp Ile Thr Ile Ser Gly Asn Cys Asn Thr Arg Glu Thr
                            50                  55                  60
            Val Leu Asn Arg Asp Gly Thr Asn Leu Asp Ile Gly Thr Asp Cys Tyr
             65                 70                  75                  80
            Pro Asp Ser Gly Thr Trp Val Ser Pro Tyr Asp Gly Ala Thr Trp Thr
                            85                  90                  95
            Ala Ala Ser Asp Val Asp Ile Asp His Val Val Pro Leu Ser Glu Ala
                            100                 105                 110
            Trp Lys Ala Gly Ala Asn Ala Trp Thr Thr Ala Gln Arg Gln Ala Phe
                            115                 120                 125
            Ala Asn Asp Leu Thr Asn Pro Gln Leu Val Ala Val Thr Asp Asn Val
                            130                 135                 140
            Asn Ser Ala Lys Gly Asp Lys Thr Pro Asp Leu Trp Lys Pro Pro Leu
            145                 150                 155                 160
            Thr Ser Phe His Cys Thr Tyr Ala Arg Met Tyr Val Lys Val Lys Ser
                            165                 170                 175
```

```
Val Tyr Ser Leu Thr Val Lys Ser Ala Glu Arg Thr Ala Leu Thr Ser
            180                 185                 190

Met Leu Ala Thr Cys
        195

<210> SEQ ID NO 7
<211> LENGTH: 728
<212> TYPE: DNA
<213> ORGANISM: Ascobolus sp. ZY179
<220> FEATURE:
<221> NAME/KEY: CDS
<222> LOCATION: (1)..(242)
<220> FEATURE:
<221> NAME/KEY: sig_peptide
<222> LOCATION: (1)..(54)
<220> FEATURE:
<221> NAME/KEY: mat_peptide
<222> LOCATION: (55)..(725)
<220> FEATURE:
<221> NAME/KEY: CDS
<222> LOCATION: (294)..(556)
<220> FEATURE:
<221> NAME/KEY: CDS
<222> LOCATION: (616)..(725)

<400> SEQUENCE: 7 atg aag gtc act ttc ctc gcc gct ctc gct gcc act ttg gct ctc act       48
Met Lys Val Thr Phe Leu Ala Ala Leu Ala Ala Thr Leu Ala Leu Thr
            -15                 -10                  -5 tct gcc aat ccg ctc cca gtc cca act cca cca aac att cca tcc gct       96
Ser Ala Asn Pro Leu Pro Val Pro Thr Pro Pro Asn Ile Pro Ser Ala
 -1   1               5                  10 acc acc gcg aag gct gag ttg gct gcc ctc ggc acc aga acc acc gac      144
Thr Thr Ala Lys Ala Glu Leu Ala Ala Leu Gly Thr Arg Thr Thr Asp
 15              20                  25                  30 gcc acc ggc tac tct cgt gac tac ttc aac cat tgg atc acc atc tcg      192
Ala Thr Gly Tyr Ser Arg Asp Tyr Phe Asn His Trp Ile Thr Ile Ser
                 35                  40                  45 ggc gcg tgc aac act cgt gag act gtt ctc aag cgt gat gga acc aac      240
Gly Ala Cys Asn Thr Arg Glu Thr Val Leu Lys Arg Asp Gly Thr Asn
             50                  55                  60 gt  gtaagctcta cttttgcgtt atatgcatcc atgctgacaa agagactata g t       294
Val gtt acc gac tct agc tgc tat gcc acc tcc gga acc tgg tac tct cca      342
Val Thr Asp Ser Ser Cys Tyr Ala Thr Ser Gly Thr Trp Tyr Ser Pro
 65                  70                  75 ttt gac ggt gcc acc tgg acc gcc gcc tcc gat gtc gat atc gac cac      390
Phe Asp Gly Ala Thr Trp Thr Ala Ala Ser Asp Val Asp Ile Asp His
 80                  85                  90                  95 gtc gtt cct ctc tcc aac gcc tgg aag tct ggt gcc aac acc tgg act      438
Val Val Pro Leu Ser Asn Ala Trp Lys Ser Gly Ala Asn Thr Trp Thr
                100                 105                 110 tct tcc aga cgc cag caa ttc gcc aat gac ttg acc aac cct caa ctc      486
Ser Ser Arg Arg Gln Gln Phe Ala Asn Asp Leu Thr Asn Pro Gln Leu
                115                 120                 125 att gcc gtc aca gac gac gtc aac caa gcc aag ggt gac aag tct cca      534
Ile Ala Val Thr Asp Asp Val Asn Gln Ala Lys Gly Asp Lys Ser Pro
            130                 135                 140 gat gcc tgg aag cca cca ctt a gtaagttcaa tctcaaacac ttgaaagtca       586
Asp Ala Trp Lys Pro Pro Leu
 145                 150 ttgaatcgga cgactaactt gttttttcag cc  tcc tac tac tgc acc tac gcc    638
                                    Thr Ser Tyr Tyr Cys Thr Tyr Ala
                                                    155
```

```
aag atg tgg gtt cgt gtc aag tat gtc tac gac ttg act gtc acc gcc    686
Lys Met Trp Val Arg Val Lys Tyr Val Tyr Asp Leu Thr Val Thr Ala
160                 165                 170 gct gag aag agc gct ttg acc agc atg ttg aac act tgc taa            728
Ala Glu Lys Ser Ala Leu Thr Ser Met Leu Asn Thr Cys
175                 180                 185
```

<210> SEQ ID NO 8
<211> LENGTH: 205
<212> TYPE: PRT
<213> ORGANISM: Ascobolus sp. ZY179

<400> SEQUENCE: 8

```
Met Lys Val Thr Phe Leu Ala Ala Leu Ala Ala Thr Leu Ala Leu Thr
            -15                 -10                 -5

Ser Ala Asn Pro Leu Pro Val Pro Thr Pro Asn Ile Pro Ser Ala
    -1  1               5                   10

Thr Thr Ala Lys Ala Glu Leu Ala Ala Leu Gly Thr Arg Thr Thr Asp
15                  20                  25                  30

Ala Thr Gly Tyr Ser Arg Asp Tyr Phe Asn His Trp Ile Thr Ile Ser
                35                  40                  45

Gly Ala Cys Asn Thr Arg Glu Thr Val Leu Lys Arg Asp Gly Thr Asn
                50                  55                  60

Val Val Thr Asp Ser Ser Cys Tyr Ala Thr Ser Gly Thr Trp Tyr Ser
                65                  70                  75

Pro Phe Asp Gly Ala Thr Trp Thr Ala Ala Ser Asp Val Asp Ile Asp
80                  85                  90

His Val Val Pro Leu Ser Asn Ala Trp Lys Ser Gly Ala Asn Thr Trp
95                  100                 105                 110

Thr Ser Ser Arg Arg Gln Gln Phe Ala Asn Asp Leu Thr Asn Pro Gln
                115                 120                 125

Leu Ile Ala Val Thr Asp Asp Val Asn Gln Ala Lys Gly Asp Lys Ser
                130                 135                 140

Pro Asp Ala Trp Lys Pro Pro Leu Thr Ser Tyr Tyr Cys Thr Tyr Ala
                145                 150                 155

Lys Met Trp Val Arg Val Lys Tyr Val Tyr Asp Leu Thr Val Thr Ala
                160                 165                 170

Ala Glu Lys Ser Ala Leu Thr Ser Met Leu Asn Thr Cys
175                 180                 185
```

<210> SEQ ID NO 9
<211> LENGTH: 187
<212> TYPE: PRT
<213> ORGANISM: Ascobolus sp. ZY179

<400> SEQUENCE: 9

```
Asn Pro Leu Pro Val Pro Thr Pro Asn Ile Pro Ser Ala Thr Thr
1               5                   10                  15

Ala Lys Ala Glu Leu Ala Ala Leu Gly Thr Arg Thr Thr Asp Ala Thr
                20                  25                  30

Gly Tyr Ser Arg Asp Tyr Phe Asn His Trp Ile Thr Ile Ser Gly Ala
                35                  40                  45

Cys Asn Thr Arg Glu Thr Val Leu Lys Arg Asp Gly Thr Asn Val Val
                50                  55                  60

Thr Asp Ser Ser Cys Tyr Ala Thr Ser Gly Thr Trp Tyr Ser Pro Phe
65                  70                  75                  80
```

```
                  Asp Gly Ala Thr Trp Thr Ala Ala Ser Asp Val Asp Ile Asp His Val
                                  85                  90                  95

Val Pro Leu Ser Asn Ala Trp Lys Ser Gly Ala Asn Trp Thr Ser
            100                 105                 110

Ser Arg Arg Gln Gln Phe Ala Asn Asp Leu Thr Asn Pro Gln Leu Ile
        115                 120                 125

Ala Val Thr Asp Asp Val Asn Gln Ala Lys Gly Asp Lys Ser Pro Asp
    130                 135                 140

Ala Trp Lys Pro Pro Leu Thr Ser Tyr Tyr Cys Thr Tyr Ala Lys Met
145                 150                 155                 160

Trp Val Arg Val Lys Tyr Val Tyr Asp Leu Thr Val Thr Ala Ala Glu
                165                 170                 175

Lys Ser Ala Leu Thr Ser Met Leu Asn Thr Cys
                180                 185
```

<210> SEQ ID NO 10
<211> LENGTH: 907
<212> TYPE: DNA
<213> ORGANISM: Morchella costata
<220> FEATURE:
<221> NAME/KEY: CDS
<222> LOCATION: (1)..(197)
<220> FEATURE:
<221> NAME/KEY: sig_peptide
<222> LOCATION: (1)..(45)
<220> FEATURE:
<221> NAME/KEY: mat_peptide
<222> LOCATION: (46)..(904)
<220> FEATURE:
<221> NAME/KEY: CDS
<222> LOCATION: (248)..(371)
<220> FEATURE:
<221> NAME/KEY: CDS
<222> LOCATION: (492)..(605)
<220> FEATURE:
<221> NAME/KEY: CDS
<222> LOCATION: (662)..(725)
<220> FEATURE:
<221> NAME/KEY: CDS
<222> LOCATION: (795)..(904)

<400> SEQUENCE: 10

```
atg aag ctc aca gca gta gcc ctc ttc ttt acg acc gct ctc gca gct    48
Met Lys Leu Thr Ala Val Ala Leu Phe Phe Thr Thr Ala Leu Ala Ala
-15             -10                 -5                  -1  1 cct acg cta gag aag cga act cct cct aat att ccc act gcc gct tcc    96
Pro Thr Leu Glu Lys Arg Thr Pro Pro Asn Ile Pro Thr Ala Ala Ser
            5                   10                  15 gcg aat act atg ctt gcc gct ctc aca aca agg acc aca gat gcc act   144
Ala Asn Thr Met Leu Ala Ala Leu Thr Thr Arg Thr Thr Asp Ala Thr
        20                  25                  30 ggt tac tcc cgc gat ctt ttc ccg cat tgg att acc cag agc ggg tct   192
Gly Tyr Ser Arg Asp Leu Phe Pro His Trp Ile Thr Gln Ser Gly Ser
    35                  40                  45 tgc aa  gtaaggcatc tggtaatcat tcataaattt cattcctgac gaaagagcag c   248
Cys Asn
50 acc cgt gag gta gtt ctt gcc cgc gat gga tcc aac gtg gtc cag gcc   296
Thr Arg Glu Val Val Leu Ala Arg Asp Gly Ser Asn Val Val Gln Ala
            55                  60                  65 agc gac tgc tca gcc tcg agc gga acc tgg ttt tcg cct tac gac ggt   344
Ser Asp Cys Ser Ala Ser Ser Gly Thr Trp Phe Ser Pro Tyr Asp Gly
        70                  75                  80 gcg acc tgg acc gct gct tct gat ctt gtaagttttc attgccacat          391
Ala Thr Trp Thr Ala Ala Ser Asp Leu
```

```
Ala Thr Trp Thr Ala Ala Ser Asp Leu
 85                  90 gtggcttgat atttgcatga gatgctcgcc gggagaaaaa aacccgtcga tattttttta        451 ttttttggc ggtaggcact gacatatccg actgtttcag gac att gat cat gtt          506
                                            Asp Ile Asp His Val
                                                         95 gtg cct ctc tcc gat gca tgg aag tcc ggg gcc aac acc tgg act aca          554
Val Pro Leu Ser Asp Ala Trp Lys Ser Gly Ala Asn Thr Trp Thr Thr
            100                 105                 110 gcc gga cgt caa gcc ttt gcc aac gat ctc acg aac ccc cag ttg att          602
Ala Gly Arg Gln Ala Phe Ala Asn Asp Leu Thr Asn Pro Gln Leu Ile
        115                 120                 125 gcc gtaagtcgtt aattctctgc tgcctcgagg aacataaac tgacggcgtg gttcag         661
Ala
130 gtc acc gat aat gta aat cag gcc aag ggt gat aag tcg cct gat gcg          709
Val Thr Asp Asn Val Asn Gln Ala Lys Gly Asp Lys Ser Pro Asp Ala
                135                 140                 145 tgg aaa cca cct ctc a gtaagttctt ttgttttcc atcagttttt ttcagcgaaa         765
Trp Lys Pro Pro Leu
            150 agagaactaa ccctaatatc tgtgttcag ca tcg tac tac tgc acc tat gca           817
                                  Thr Ser Tyr Tyr Cys Thr Tyr Ala
                                                  155 agg atg tgg gtt aag gtg aag agt gtg tat tca ttg tct gtg acc tca          865
Arg Met Trp Val Lys Val Lys Ser Val Tyr Ser Leu Ser Val Thr Ser
160                 165                 170                 175 gct gag cgt tcg gcg ttg acg agc atg ttg aac acg tgc tga                  907
Ala Glu Arg Ser Ala Leu Thr Ser Met Leu Asn Thr Cys
                180                 185

<210> SEQ ID NO 11
<211> LENGTH: 203
<212> TYPE: PRT
<213> ORGANISM: Morchella costata

<400> SEQUENCE: 11

Met Lys Leu Thr Ala Val Ala Leu Phe Phe Thr Thr Ala Leu Ala Ala
-15                 -10                  -5                  -1  1

Pro Thr Leu Glu Lys Arg Thr Pro Pro Asn Ile Pro Thr Ala Ala Ser
             5                  10                  15

Ala Asn Thr Met Leu Ala Ala Leu Thr Thr Arg Thr Thr Asp Ala Thr
            20                  25                  30

Gly Tyr Ser Arg Asp Leu Phe Pro His Trp Ile Thr Gln Ser Gly Ser
        35                  40                  45

Cys Asn Thr Arg Glu Val Val Leu Ala Arg Asp Gly Ser Asn Val Val
50                  55                  60                  65

Gln Ala Ser Asp Cys Ser Ala Ser Ser Gly Thr Trp Phe Ser Pro Tyr
                70                  75                  80

Asp Gly Ala Thr Trp Thr Ala Ala Ser Asp Leu Asp Ile Asp His Val
            85                  90                  95

Val Pro Leu Ser Asp Ala Trp Lys Ser Gly Ala Asn Thr Trp Thr Thr
            100                 105                 110

Ala Gly Arg Gln Ala Phe Ala Asn Asp Leu Thr Asn Pro Gln Leu Ile
        115                 120                 125

Ala Val Thr Asp Asn Val Asn Gln Ala Lys Gly Asp Lys Ser Pro Asp
130                 135                 140                 145
```

```
Ala Trp Lys Pro Pro Leu Thr Ser Tyr Tyr Cys Thr Tyr Ala Arg Met
            150                 155                 160

Trp Val Lys Val Lys Ser Val Tyr Ser Leu Ser Val Thr Ser Ala Glu
        165                 170                 175

Arg Ser Ala Leu Thr Ser Met Leu Asn Thr Cys
        180                 185

<210> SEQ ID NO 12
<211> LENGTH: 188
<212> TYPE: PRT
<213> ORGANISM: Morchella costata

<400> SEQUENCE: 12

Ala Pro Thr Leu Glu Lys Arg Thr Pro Pro Asn Ile Pro Thr Ala Ala
1               5                   10                  15

Ser Ala Asn Thr Met Leu Ala Ala Leu Thr Thr Arg Thr Thr Asp Ala
            20                  25                  30

Thr Gly Tyr Ser Arg Asp Leu Phe Pro His Trp Ile Thr Gln Ser Gly
        35                  40                  45

Ser Cys Asn Thr Arg Glu Val Val Leu Ala Arg Asp Gly Ser Asn Val
    50                  55                  60

Val Gln Ala Ser Asp Cys Ser Ala Ser Ser Gly Thr Trp Phe Ser Pro
65                  70                  75                  80

Tyr Asp Gly Ala Thr Trp Thr Ala Ala Ser Asp Leu Asp Ile Asp His
                85                  90                  95

Val Val Pro Leu Ser Asp Ala Trp Lys Ser Gly Ala Asn Thr Trp Thr
            100                 105                 110

Thr Ala Gly Arg Gln Ala Phe Ala Asn Asp Leu Thr Asn Pro Gln Leu
        115                 120                 125

Ile Ala Val Thr Asp Asn Val Asn Gln Ala Lys Gly Asp Lys Ser Pro
    130                 135                 140

Asp Ala Trp Lys Pro Pro Leu Thr Ser Tyr Tyr Cys Thr Tyr Ala Arg
145                 150                 155                 160

Met Trp Val Lys Val Lys Ser Val Tyr Ser Leu Ser Val Thr Ser Ala
                165                 170                 175

Glu Arg Ser Ala Leu Thr Ser Met Leu Asn Thr Cys
            180                 185

<210> SEQ ID NO 13
<211> LENGTH: 822
<212> TYPE: DNA
<213> ORGANISM: Trichobolus zukalii
<220> FEATURE:
<221> NAME/KEY: CDS
<222> LOCATION: (1)..(175)
<220> FEATURE:
<221> NAME/KEY: sig_peptide
<222> LOCATION: (1)..(57)
<220> FEATURE:
<221> NAME/KEY: mat_peptide
<222> LOCATION: (58)..(819)
<220> FEATURE:
<221> NAME/KEY: CDS
<222> LOCATION: (234)..(402)
<220> FEATURE:
<221> NAME/KEY: CDS
<222> LOCATION: (464)..(642)
<220> FEATURE:
<221> NAME/KEY: CDS
<222> LOCATION: (710)..(819)

<400> SEQUENCE: 13
```

```
atg cat ttc tca tcc ttc gtc ctc ccg gtg att gcg ctg gca tcc agc        48
Met His Phe Ser Ser Phe Val Leu Pro Val Ile Ala Leu Ala Ser Ser
            -15                 -10                 -5 gct ctg gct gct ccg act ccg gct ccc ctc ctc gag aag cgt tct cct        96
Ala Leu Ala Ala Pro Thr Pro Ala Pro Leu Leu Glu Lys Arg Ser Pro
    -1  1                   5                   10 ccg aat atc cca tcc aag tct tcc gcg gtc tca atg ctt gca ggc ctc       144
Pro Asn Ile Pro Ser Lys Ser Ser Ala Val Ser Met Leu Ala Gly Leu
        15                  20                  25 agc aca cga acc agc gat gcc acc gga tat g gtatgttcca gcattcaaag       195
Ser Thr Arg Thr Ser Asp Ala Thr Gly Tyr
30                  35 ggagataggc tgcattcgaa aactgacaat atctacag ac  cgc gat ctc ttc ccc     250
                                             Asp Arg Asp Leu Phe Pro
                                              40              45 cac tgg atc aca atc tct ggc acc tgc aat acc cgt gag acc gtc ctc       298
His Trp Ile Thr Ile Ser Gly Thr Cys Asn Thr Arg Glu Thr Val Leu
                50                  55                  60 aag cgc gac gcc agt tcc atc act gtt ggc gac aac tgt gcc gct acc       346
Lys Arg Asp Ala Ser Ser Ile Thr Val Gly Asp Asn Cys Ala Ala Thr
                65                  70                  75 tct gga tcg tgg ttt tcg ccg tac gat ggc gcc acc tgg acg gct gct       394
Ser Gly Ser Trp Phe Ser Pro Tyr Asp Gly Ala Thr Trp Thr Ala Ala
                80                  85                  90 tcc gac ct gtaagcatgc atttttttt tttttacccc tcctgtgaac                 442
Ser Asp Leu
        95 gttcctctaa cagcttccca g t gat atc gac cat gtt gtt cct ttg agt gac     494
                         Asp Ile Asp His Val Val Pro Leu Ser Asp
                                100                 105 gcc tgg aag tct ggt gcc aat acc tgg acc acc gcc aag cgc caa acc       542
Ala Trp Lys Ser Gly Ala Asn Thr Trp Thr Thr Ala Lys Arg Gln Thr
                110                 115                 120 ttt gcc aat gat ctg acc aac ccc cag ctt att gct gtt acc gat aat       590
Phe Ala Asn Asp Leu Thr Asn Pro Gln Leu Ile Ala Val Thr Asp Asn
            125                 130                 135 gtc aac cag gct aag gga gat aag tcc ccg gac gca tgg aag ccg ccc       638
Val Asn Gln Ala Lys Gly Asp Lys Ser Pro Asp Ala Trp Lys Pro Pro
        140                 145                 150 ttg t gtaagtttcc cgagtctccg ttctgtgtat ccccttcgag gagattgatg          692
Leu
155 ctaatggatt cttacag cc  tct tac tac tgc acc tac gcc aag atg tgg        741
                      Ser Ser Tyr Tyr Cys Thr Tyr Ala Lys Met Trp
                                    160                 165 gtc aag gtc aaa agc gct tat ggg ctt tcc gtc aag gct gct gag agg       789
Val Lys Val Lys Ser Ala Tyr Gly Leu Ser Val Lys Ala Ala Glu Arg
                170                 175                 180 act gct ttg act tcc atg ttg aac act tgc tag                           822
Thr Ala Leu Thr Ser Met Leu Asn Thr Cys
            185                 190

<210> SEQ ID NO 14
<211> LENGTH: 211
<212> TYPE: PRT
<213> ORGANISM: Trichobolus zukalii

<400> SEQUENCE: 14

Met His Phe Ser Ser Phe Val Leu Pro Val Ile Ala Leu Ala Ser Ser
                -15                 -10                 -5
```

```
Ala Leu Ala Ala Pro Thr Pro Ala Pro Leu Leu Glu Lys Arg Ser Pro
    -1   1               5                      10

Pro Asn Ile Pro Ser Lys Ser Ser Ala Val Ser Met Leu Ala Gly Leu
     15              20                  25

Ser Thr Arg Thr Ser Asp Ala Thr Gly Tyr Asp Arg Asp Leu Phe Pro
 30              35              40                          45

His Trp Ile Thr Ile Ser Gly Thr Cys Asn Thr Arg Glu Thr Val Leu
             50              55                      60

Lys Arg Asp Ala Ser Ser Ile Thr Val Gly Asp Asn Cys Ala Ala Thr
             65              70              75

Ser Gly Ser Trp Phe Ser Pro Tyr Asp Gly Ala Thr Trp Thr Ala Ala
             80              85                      90

Ser Asp Leu Asp Ile Asp His Val Val Pro Leu Ser Asp Ala Trp Lys
         95              100                 105

Ser Gly Ala Asn Thr Trp Thr Thr Ala Lys Arg Gln Thr Phe Ala Asn
110                 115                 120                 125

Asp Leu Thr Asn Pro Gln Leu Ile Ala Val Thr Asp Asn Val Asn Gln
                 130                 135                 140

Ala Lys Gly Asp Lys Ser Pro Asp Ala Trp Lys Pro Pro Leu Ser Ser
             145                 150                 155

Tyr Tyr Cys Thr Tyr Ala Lys Met Trp Val Lys Val Lys Ser Ala Tyr
             160                 165                 170

Gly Leu Ser Val Lys Ala Ala Glu Arg Thr Ala Leu Thr Ser Met Leu
         175                 180                 185

Asn Thr Cys
190

<210> SEQ ID NO 15
<211> LENGTH: 192
<212> TYPE: PRT
<213> ORGANISM: Trichobolus zukalii

<400> SEQUENCE: 15

Ala Pro Thr Pro Ala Pro Leu Leu Glu Lys Arg Ser Pro Pro Asn Ile
  1               5                  10                  15

Pro Ser Lys Ser Ser Ala Val Ser Met Leu Ala Gly Leu Ser Thr Arg
                 20                  25                  30

Thr Ser Asp Ala Thr Gly Tyr Asp Arg Asp Leu Phe Pro His Trp Ile
             35                  40                  45

Thr Ile Ser Gly Thr Cys Asn Thr Arg Glu Thr Val Leu Lys Arg Asp
 50                  55                  60

Ala Ser Ser Ile Thr Val Gly Asp Asn Cys Ala Ala Thr Ser Gly Ser
 65                  70                  75                  80

Trp Phe Ser Pro Tyr Asp Gly Ala Thr Trp Thr Ala Ala Ser Asp Leu
                 85                  90                  95

Asp Ile Asp His Val Val Pro Leu Ser Asp Ala Trp Lys Ser Gly Ala
             100                 105                 110

Asn Thr Trp Thr Thr Ala Lys Arg Gln Thr Phe Ala Asn Asp Leu Thr
         115                 120                 125

Asn Pro Gln Leu Ile Ala Val Thr Asp Asn Val Asn Gln Ala Lys Gly
     130                 135                 140

Asp Lys Ser Pro Asp Ala Trp Lys Pro Pro Leu Ser Ser Tyr Tyr Cys
145                 150                 155                 160

Thr Tyr Ala Lys Met Trp Val Lys Val Lys Ser Ala Tyr Gly Leu Ser
                 165                 170                 175
```

```
Val Lys Ala Ala Glu Arg Thr Ala Leu Thr Ser Met Leu Asn Thr Cys
        180                 185                 190

<210> SEQ ID NO 16
<211> LENGTH: 787
<212> TYPE: DNA
<213> ORGANISM: Trichophaea saccata
<220> FEATURE:
<221> NAME/KEY: CDS
<222> LOCATION: (1)..(158)
<220> FEATURE:
<221> NAME/KEY: sig_peptide
<222> LOCATION: (1)..(51)
<220> FEATURE:
<221> NAME/KEY: mat_peptide
<222> LOCATION: (52)..(784)
<220> FEATURE:
<221> NAME/KEY: CDS
<222> LOCATION: (215)..(437)
<220> FEATURE:
<221> NAME/KEY: CDS
<222> LOCATION: (493)..(592)
<220> FEATURE:
<221> NAME/KEY: CDS
<222> LOCATION: (654)..(784)

<400> SEQUENCE: 16 atg aag ttc tct cct ctt gcc ctc ctc ggc ctc gtc gcc agc gcc tct      48
Met Lys Phe Ser Pro Leu Ala Leu Leu Gly Leu Val Ala Ser Ala Ser
        -15                 -10                  -5 gcg gct gcg atc gag aag cgc acg cca cca aac att ccc agc act tcc      96
Ala Ala Ala Ile Glu Lys Arg Thr Pro Pro Asn Ile Pro Ser Thr Ser
 -1   1               5                  10                  15 agc gcc aag tcc atg ctt gcg ggt ttg agc gtt cgg acc act gat gcc     144
Ser Ala Lys Ser Met Leu Ala Gly Leu Ser Val Arg Thr Thr Asp Ala
                20                  25                  30 act ggt tac gac cg gttagtgaac ccactgccac gcacgtgatg tcggtcgtta     198
Thr Gly Tyr Asp Arg
                35 atggtcactc ctccag a tcc ctc ttc cct cac tgg atc act atc tct ggc     248
                  Ser Leu Phe Pro His Trp Ile Thr Ile Ser Gly
                                      40                  45 acg tgc gac act cgt gag acg gtg ctg aac cgt gat ggc acc ggc ctc     296
Thr Cys Asp Thr Arg Glu Thr Val Leu Asn Arg Asp Gly Thr Gly Leu
        50                  55                  60 act atc ggc agt gac tgc tac cct act gcc ggc acc tgg tac tct cca     344
Thr Ile Gly Ser Asp Cys Tyr Pro Thr Ala Gly Thr Trp Tyr Ser Pro
 65                  70                  75 tac gac gga gcc acc tgg act gca gcc tcg gat ttg gac atc gac cac     392
Tyr Asp Gly Ala Thr Trp Thr Ala Ala Ser Asp Leu Asp Ile Asp His
 80                  85                  90                  95 gtt gtc ccc ctt tct gac gca tgg aag tcg ggt gca aat ctc tgg           437
Val Val Pro Leu Ser Asp Ala Trp Lys Ser Gly Ala Asn Leu Trp
                    100                 105                 110 gtacattccc tcccctcttt tccttcagt gggcaataac taacatcatg aacag act      495
                                                            Thr acc tcc cag cgc cag aac ttc gcc aat gac ctt acc aac ccg cag ctg     543
Thr Ser Gln Arg Gln Asn Phe Ala Asn Asp Leu Thr Asn Pro Gln Leu
            115                 120                 125 att gcg gtt acg gat aac gtc aac cag gca aag ggt gac aag agc cct g   592
Ile Ala Val Thr Asp Asn Val Asn Gln Ala Lys Gly Asp Lys Ser Pro
        130                 135                 140 gtatatagcc ccacccgaac cagtatcctc tcactgtacc gacggctgac ttgagaaaaa     652
```

```
g at  ttg tgg aag ccc ccg ttg act tcg tac cat tgc aca tat gcc aag       700
  Asp Leu Trp Lys Pro Pro Leu Thr Ser Tyr His Cys Thr Tyr Ala Lys
      145                 150                 155 atg tgg gtt aag gtc aag agc gtg tac tcc ctc tcg gtc acc gcc gct         748
Met Trp Val Lys Val Lys Ser Val Tyr Ser Leu Ser Val Thr Ala Ala
160                 165                 170                 175 gag aag tcg gcc ttg acg tcc atg ttg aac acc tgt taa                     787
Glu Lys Ser Ala Leu Thr Ser Met Leu Asn Thr Cys
                180                 185
```

<210> SEQ ID NO 17
<211> LENGTH: 204
<212> TYPE: PRT
<213> ORGANISM: Trichophaea saccata

<400> SEQUENCE: 17

```
Met Lys Phe Ser Pro Leu Ala Leu Leu Gly Leu Val Ala Ser Ala Ser
        -15                 -10                  -5

Ala Ala Ala Ile Glu Lys Arg Thr Pro Pro Asn Ile Pro Ser Thr Ser
 -1  1               5                  10                  15

Ser Ala Lys Ser Met Leu Ala Gly Leu Ser Val Arg Thr Thr Asp Ala
                20                  25                  30

Thr Gly Tyr Asp Arg Ser Leu Phe Pro His Trp Ile Thr Ile Ser Gly
            35                  40                  45

Thr Cys Asp Thr Arg Glu Thr Val Leu Asn Arg Asp Gly Thr Gly Leu
        50                  55                  60

Thr Ile Gly Ser Asp Cys Tyr Pro Thr Ala Gly Thr Trp Tyr Ser Pro
    65                  70                  75

Tyr Asp Gly Ala Thr Trp Thr Ala Ala Ser Asp Leu Asp Ile Asp His
80                  85                  90                  95

Val Val Pro Leu Ser Asp Ala Trp Lys Ser Gly Ala Asn Leu Trp Thr
                100                 105                 110

Thr Ser Gln Arg Gln Asn Phe Ala Asn Asp Leu Thr Asn Pro Gln Leu
            115                 120                 125

Ile Ala Val Thr Asp Asn Val Asn Gln Ala Lys Gly Asp Lys Ser Pro
        130                 135                 140

Asp Leu Trp Lys Pro Pro Leu Thr Ser Tyr His Cys Thr Tyr Ala Lys
    145                 150                 155

Met Trp Val Lys Val Lys Ser Val Tyr Ser Leu Ser Val Thr Ala Ala
160                 165                 170                 175

Glu Lys Ser Ala Leu Thr Ser Met Leu Asn Thr Cys
                180                 185
```

<210> SEQ ID NO 18
<211> LENGTH: 187
<212> TYPE: PRT
<213> ORGANISM: Trichophaea saccata

<400> SEQUENCE: 18

```
Ala Ala Ile Glu Lys Arg Thr Pro Pro Asn Ile Pro Ser Thr Ser Ser
1               5                  10                  15

Ala Lys Ser Met Leu Ala Gly Leu Ser Val Arg Thr Thr Asp Ala Thr
            20                  25                  30

Gly Tyr Asp Arg Ser Leu Phe Pro His Trp Ile Thr Ile Ser Gly Thr
        35                  40                  45

Cys Asp Thr Arg Glu Thr Val Leu Asn Arg Asp Gly Thr Gly Leu Thr
    50                  55                  60
```

```
Ile Gly Ser Asp Cys Tyr Pro Thr Ala Gly Thr Trp Tyr Ser Pro Tyr
 65                  70                  75                  80

Asp Gly Ala Thr Trp Thr Ala Ala Ser Asp Leu Asp Ile Asp His Val
                 85                  90                  95

Val Pro Leu Ser Asp Ala Trp Lys Ser Gly Ala Asn Leu Trp Thr Thr
            100                 105                 110

Ser Gln Arg Gln Asn Phe Ala Asn Asp Leu Thr Asn Pro Gln Leu Ile
        115                 120                 125

Ala Val Thr Asp Asn Val Asn Gln Ala Lys Gly Asp Lys Ser Pro Asp
    130                 135                 140

Leu Trp Lys Pro Pro Leu Thr Ser Tyr His Cys Thr Tyr Ala Lys Met
145                 150                 155                 160

Trp Val Lys Val Lys Ser Val Tyr Ser Leu Ser Val Thr Ala Ala Glu
                165                 170                 175

Lys Ser Ala Leu Thr Ser Met Leu Asn Thr Cys
            180                 185

<210> SEQ ID NO 19
<211> LENGTH: 784
<212> TYPE: DNA
<213> ORGANISM: Trichophaea minuta
<220> FEATURE:
<221> NAME/KEY: CDS
<222> LOCATION: (1)..(158)
<220> FEATURE:
<221> NAME/KEY: sig_peptide
<222> LOCATION: (1)..(51)
<220> FEATURE:
<221> NAME/KEY: mat_peptide
<222> LOCATION: (52)..(781)
<220> FEATURE:
<221> NAME/KEY: CDS
<222> LOCATION: (215)..(437)
<220> FEATURE:
<221> NAME/KEY: CDS
<222> LOCATION: (494)..(593)
<220> FEATURE:
<221> NAME/KEY: CDS
<222> LOCATION: (651)..(781)

<400> SEQUENCE: 19 atg aag ttc tct cct ctt gcc ctt ttt ggc ctc gtc gcc agc gta tct      48
Met Lys Phe Ser Pro Leu Ala Leu Phe Gly Leu Val Ala Ser Val Ser
        -15                 -10                  -5 gcc gct gca atc gag aag cgc aca cct cca aac att ccc agc acc tcc      96
Ala Ala Ala Ile Glu Lys Arg Thr Pro Pro Asn Ile Pro Ser Thr Ser
 -1   1               5                  10                  15 agc gcc cag tct atg ctt tcg ggc ttg agc att cgg acc act aat gcc     144
Ser Ala Gln Ser Met Leu Ser Gly Leu Ser Ile Arg Thr Thr Asn Ala
                 20                  25                  30 act ggt tac gac cg gttagtaaac catcgttcac atacgagata tccagtgttt      198
Thr Gly Tyr Asp Arg
                35 aacattcccc atctag c tct ctc ttc cct cac tgg atc acc atc tct ggc     248
                 Ser Leu Phe Pro His Trp Ile Thr Ile Ser Gly
                                 40                  45 aac tgc gac acc cgc gag aca gtg ctg aac cgt gac gga acc gac ctt     296
Asn Cys Asp Thr Arg Glu Thr Val Leu Asn Arg Asp Gly Thr Asp Leu
         50                  55                  60 acc atc ggc agc gac tgc tat cct agt gac ggc act tgg tac tct ccc     344
Thr Ile Gly Ser Asp Cys Tyr Pro Ser Asp Gly Thr Trp Tyr Ser Pro
 65                  70                  75 tac gac ggc gcc act tgg act gcc gcc tcg gat ttg gac atc gat cac     392
Tyr Asp Gly Ala Thr Trp Thr Ala Ala Ser Asp Leu Asp Ile Asp His
```

```
Tyr Asp Gly Ala Thr Trp Thr Ala Ala Ser Asp Leu Asp Ile Asp His
 80              85                  90                  95 gtt gtt ccc ctt tcc gat gct tgg aag tcg ggt gca aac ctc tgg         437
Val Val Pro Leu Ser Asp Ala Trp Lys Ser Gly Ala Asn Leu Trp
                100                 105                 110 gtatctccac actccgcccc tcatgtctag aaggcaatat ttaatgtcat aatcag act    496
                                                              Thr act gcc cag cgc cag aac ttc gca aat gac ctc tcc aac ccg cag ctt     544
Thr Ala Gln Arg Gln Asn Phe Ala Asn Asp Leu Ser Asn Pro Gln Leu
            115                 120                 125 att gcg gtc acg gac agt gtc aac caa gca aag agt gac aag agc cct g   593
Ile Ala Val Thr Asp Ser Val Asn Gln Ala Lys Ser Asp Lys Ser Pro
        130                 135                 140 gtatgcctcc accaccatcc tctcactgaa ggcaaccccc cgctgacata atgaaag       650 at ttg tgg aag ccc ccg ctc acc tcg tac cac tgc act tac gcc aag      697
Asp Leu Trp Lys Pro Pro Leu Thr Ser Tyr His Cys Thr Tyr Ala Lys
        145                 150                 155 atg tgg gtt aag gtc aag agt gtt tac tcc ctc tcg gtc act tcg gct     745
Met Trp Val Lys Val Lys Ser Val Tyr Ser Leu Ser Val Thr Ser Ala
160                 165                 170                 175 gag aag tcg gct ttg acg tct atg ttg aac acg tgt taa                 784
Glu Lys Ser Ala Leu Thr Ser Met Leu Asn Thr Cys
                180                 185

<210> SEQ ID NO 20
<211> LENGTH: 204
<212> TYPE: PRT
<213> ORGANISM: Trichophaea minuta

<400> SEQUENCE: 20

Met Lys Phe Ser Pro Leu Ala Leu Phe Gly Leu Val Ala Ser Val Ser
        -15                 -10                  -5

Ala Ala Ala Ile Glu Lys Arg Thr Pro Pro Asn Ile Pro Ser Thr Ser
 -1  1               5                  10                  15

Ser Ala Gln Ser Met Leu Ser Gly Leu Ser Ile Arg Thr Thr Asn Ala
                 20                  25                  30

Thr Gly Tyr Asp Arg Ser Leu Phe Pro His Trp Ile Thr Ile Ser Gly
             35                  40                  45

Asn Cys Asp Thr Arg Glu Thr Val Leu Asn Arg Asp Gly Thr Asp Leu
         50                  55                  60

Thr Ile Gly Ser Asp Cys Tyr Pro Ser Asp Gly Thr Trp Tyr Ser Pro
     65                  70                  75

Tyr Asp Gly Ala Thr Trp Thr Ala Ala Ser Asp Leu Asp Ile Asp His
 80                  85                  90                  95

Val Val Pro Leu Ser Asp Ala Trp Lys Ser Gly Ala Asn Leu Trp Thr
                100                 105                 110

Thr Ala Gln Arg Gln Asn Phe Ala Asn Asp Leu Ser Asn Pro Gln Leu
            115                 120                 125

Ile Ala Val Thr Asp Ser Val Asn Gln Ala Lys Ser Asp Lys Ser Pro
        130                 135                 140

Asp Leu Trp Lys Pro Pro Leu Thr Ser Tyr His Cys Thr Tyr Ala Lys
    145                 150                 155

Met Trp Val Lys Val Lys Ser Val Tyr Ser Leu Ser Val Thr Ser Ala
160                 165                 170                 175

Glu Lys Ser Ala Leu Thr Ser Met Leu Asn Thr Cys
                180                 185
```

<210> SEQ ID NO 21
<211> LENGTH: 187
<212> TYPE: PRT
<213> ORGANISM: Trichophaea minuta

<400> SEQUENCE: 21

Ala Ala Ile Glu Lys Arg Thr Pro Pro Asn Ile Pro Ser Thr Ser Ser
1               5                   10                  15

Ala Gln Ser Met Leu Ser Gly Leu Ser Ile Arg Thr Thr Asn Ala Thr
            20                  25                  30

Gly Tyr Asp Arg Ser Leu Phe Pro His Trp Ile Thr Ile Ser Gly Asn
        35                  40                  45

Cys Asp Thr Arg Glu Thr Val Leu Asn Arg Asp Gly Thr Asp Leu Thr
    50                  55                  60

Ile Gly Ser Asp Cys Tyr Pro Ser Asp Gly Thr Trp Tyr Ser Pro Tyr
65                  70                  75                  80

Asp Gly Ala Thr Trp Thr Ala Ala Ser Asp Leu Asp Ile Asp His Val
                85                  90                  95

Val Pro Leu Ser Asp Ala Trp Lys Ser Gly Ala Asn Leu Trp Thr Thr
            100                 105                 110

Ala Gln Arg Gln Asn Phe Ala Asn Asp Leu Ser Asn Pro Gln Leu Ile
        115                 120                 125

Ala Val Thr Asp Ser Val Asn Gln Ala Lys Ser Asp Lys Ser Pro Asp
    130                 135                 140

Leu Trp Lys Pro Pro Leu Thr Ser Tyr His Cys Thr Tyr Ala Lys Met
145                 150                 155                 160

Trp Val Lys Val Lys Ser Val Tyr Ser Leu Ser Val Thr Ser Ala Glu
                165                 170                 175

Lys Ser Ala Leu Thr Ser Met Leu Asn Thr Cys
            180                 185

<210> SEQ ID NO 22
<211> LENGTH: 787
<212> TYPE: DNA
<213> ORGANISM: Trichophaea minuta
<220> FEATURE:
<221> NAME/KEY: CDS
<222> LOCATION: (1)..(158)
<220> FEATURE:
<221> NAME/KEY: sig_peptide
<222> LOCATION: (1)..(51)
<220> FEATURE:
<221> NAME/KEY: mat_peptide
<222> LOCATION: (52)..(784)
<220> FEATURE:
<221> NAME/KEY: CDS
<222> LOCATION: (215)..(437)
<220> FEATURE:
<221> NAME/KEY: CDS
<222> LOCATION: (494)..(593)
<220> FEATURE:
<221> NAME/KEY: CDS
<222> LOCATION: (654)..(784)

<400> SEQUENCE: 22 atg aag ttc tct cct ctt gcc ctc ttt ggc ctc gtc gcc agc gcc tct     48
Met Lys Phe Ser Pro Leu Ala Leu Phe Gly Leu Val Ala Ser Ala Ser
        -15                 -10                 -5 gcc gct gca atc gag aag cgc act ccc cca aac att ccc agc acc tcc     96
Ala Ala Ala Ile Glu Lys Arg Thr Pro Pro Asn Ile Pro Ser Thr Ser
  -1  1               5                   10                  15 agc gcc aag tcc atg ctt tcg ggc ttg agc att cgg acc act gat gcc    144

```
Ser Ala Lys Ser Met Leu Ser Gly Leu Ser Ile Arg Thr Thr Asp Ala
            20                  25                  30 act ggt tac gac cg  gttagtaaac catcattcac acacgagata tccagtgttt       198
Thr Gly Tyr Asp Arg
            35 aacattcccc acccag c tct ctc ttc ccc cac tgg atc acc atc tct ggc       248
                    Ser Leu Phe Pro His Trp Ile Thr Ile Ser Gly
                                40                  45 aac tgc gac acc cgc gag aca gtg ctg aac cgt gac gga acc ggc ctt       296
Asn Cys Asp Thr Arg Glu Thr Val Leu Asn Arg Asp Gly Thr Gly Leu
            50                  55                  60 acc atc ggc agc gac tgc tac cct agt gcc ggc act tgg tac tct ccc       344
Thr Ile Gly Ser Asp Cys Tyr Pro Ser Ala Gly Thr Trp Tyr Ser Pro
65                  70                  75 tac gac gga gcc acc tgg act gcc gcc tcg gat ttg gac atc gac cac       392
Tyr Asp Gly Ala Thr Trp Thr Ala Ala Ser Asp Leu Asp Ile Asp His
80                  85                  90                  95 gtt gtt ccc ctt tcc gat gct tgg aag tcg ggt gca aac ctc tgg           437
Val Val Pro Leu Ser Asp Ala Trp Lys Ser Gly Ala Asn Leu Trp
                100                 105                 110 gtatctccac actccacccc tcatgtctag aaggcaatat ttaacgtcat attcag act     496
                                                                Thr acc gcc cag cgc cag aac ttc gca aat gac ctc tcc aac ccg cag ctt       544
Thr Ala Gln Arg Gln Asn Phe Ala Asn Asp Leu Ser Asn Pro Gln Leu
            115                 120                 125 att gcg gtc acg gat aat gtc aac caa gca aag agt gac aag agc cct g     593
Ile Ala Val Thr Asp Asn Val Asn Gln Ala Lys Ser Asp Lys Ser Pro
            130                 135                 140 gtatgcctcc accaccacca tcctctcact gaaggcaccc cccgctgaca taatgaaaag     653 at ttg tgg aag ccc ccg ctc acc tcg tac cac tgc act tac gcc aag        700
Asp Leu Trp Lys Pro Pro Leu Thr Ser Tyr His Cys Thr Tyr Ala Lys
    145                 150                 155 atg tgg gtt aag gtc aag agt gtt tac tcc ctc tcg gtc act tcg gct       748
Met Trp Val Lys Val Lys Ser Val Tyr Ser Leu Ser Val Thr Ser Ala
160                 165                 170                 175 gag aag tcg gct ttg acg tct atg ttg aac acg tgt taa                   787
Glu Lys Ser Ala Leu Thr Ser Met Leu Asn Thr Cys
                180                 185

<210> SEQ ID NO 23
<211> LENGTH: 204
<212> TYPE: PRT
<213> ORGANISM: Trichophaea minuta

<400> SEQUENCE: 23

Met Lys Phe Ser Pro Leu Ala Leu Phe Gly Leu Val Ala Ser Ala Ser
            -15                 -10                  -5

Ala Ala Ala Ile Glu Lys Arg Thr Pro Pro Asn Ile Pro Ser Thr Ser
-1   1              5                   10                  15

Ser Ala Lys Ser Met Leu Ser Gly Leu Ser Ile Arg Thr Thr Asp Ala
            20                  25                  30

Thr Gly Tyr Asp Arg Ser Leu Phe Pro His Trp Ile Thr Ile Ser Gly
            35                  40                  45

Asn Cys Asp Thr Arg Glu Thr Val Leu Asn Arg Asp Gly Thr Gly Leu
            50                  55                  60

Thr Ile Gly Ser Asp Cys Tyr Pro Ser Ala Gly Thr Trp Tyr Ser Pro
65                  70                  75

Tyr Asp Gly Ala Thr Trp Thr Ala Ala Ser Asp Leu Asp Ile Asp His
```

```
                80                  85                  90                  95
Val Val Pro Leu Ser Asp Ala Trp Lys Ser Gly Ala Asn Leu Trp Thr
                100                 105                 110

Thr Ala Gln Arg Gln Asn Phe Ala Asn Asp Leu Ser Asn Pro Gln Leu
                115                 120                 125

Ile Ala Val Thr Asp Asn Val Asn Gln Ala Lys Ser Asp Lys Ser Pro
                130                 135                 140

Asp Leu Trp Lys Pro Pro Leu Thr Ser Tyr His Cys Thr Tyr Ala Lys
            145                 150                 155

Met Trp Val Lys Val Lys Ser Val Tyr Ser Leu Ser Val Thr Ser Ala
160                 165                 170                 175

Glu Lys Ser Ala Leu Thr Ser Met Leu Asn Thr Cys
                180                 185

<210> SEQ ID NO 24
<211> LENGTH: 187
<212> TYPE: PRT
<213> ORGANISM: Trichophaea minuta

<400> SEQUENCE: 24

Ala Ala Ile Glu Lys Arg Thr Pro Pro Asn Ile Pro Ser Thr Ser Ser
1               5                   10                  15

Ala Lys Ser Met Leu Ser Gly Leu Ser Ile Arg Thr Thr Asp Ala Thr
                20                  25                  30

Gly Tyr Asp Arg Ser Leu Phe Pro His Trp Ile Thr Ile Ser Gly Asn
                35                  40                  45

Cys Asp Thr Arg Glu Thr Val Leu Asn Arg Asp Gly Thr Gly Leu Thr
            50                  55                  60

Ile Gly Ser Asp Cys Tyr Pro Ser Ala Gly Thr Trp Tyr Ser Pro Tyr
65              70                  75                  80

Asp Gly Ala Thr Trp Thr Ala Ala Ser Asp Leu Asp Ile Asp His Val
                85                  90                  95

Val Pro Leu Ser Asp Ala Trp Lys Ser Gly Ala Asn Leu Trp Thr Thr
                100                 105                 110

Ala Gln Arg Gln Asn Phe Ala Asn Asp Leu Ser Asn Pro Gln Leu Ile
                115                 120                 125

Ala Val Thr Asp Asn Val Asn Gln Ala Lys Ser Asp Lys Ser Pro Asp
                130                 135                 140

Leu Trp Lys Pro Pro Leu Thr Ser Tyr His Cys Thr Tyr Ala Lys Met
145                 150                 155                 160

Trp Val Lys Val Lys Ser Val Tyr Ser Leu Ser Val Thr Ser Ala Glu
                165                 170                 175

Lys Ser Ala Leu Thr Ser Met Leu Asn Thr Cys
                180                 185

<210> SEQ ID NO 25
<211> LENGTH: 793
<212> TYPE: DNA
<213> ORGANISM: Trichophaea abundans
<220> FEATURE:
<221> NAME/KEY: CDS
<222> LOCATION: (1)..(158)
<220> FEATURE:
<221> NAME/KEY: sig_peptide
<222> LOCATION: (1)..(51)
<220> FEATURE:
<221> NAME/KEY: mat_peptide
<222> LOCATION: (52)..(790)
<220> FEATURE:
```

<220> FEATURE:
<221> NAME/KEY: CDS
<222> LOCATION: (215)..(437)
<220> FEATURE:
<221> NAME/KEY: CDS
<222> LOCATION: (502)..(601)
<220> FEATURE:
<221> NAME/KEY: CDS
<222> LOCATION: (660)..(790)

<400> SEQUENCE: 25

```
atg aag ttc tct cct ctt gcc ttc ttc ggc ctc gtc gcc agc gtc tcg      48
Met Lys Phe Ser Pro Leu Ala Phe Phe Gly Leu Val Ala Ser Val Ser
    -15                 -10                 -5 gcc gct gca gtc gag aag cgt aca cct cca aac att ccc agc acc acc      96
Ala Ala Ala Val Glu Lys Arg Thr Pro Pro Asn Ile Pro Ser Thr Thr
-1   1               5                   10                  15 agc gcc aag tcc atg ctt tca ggc ttg aac att cgg act act gat gcc     144
Ser Ala Lys Ser Met Leu Ser Gly Leu Asn Ile Arg Thr Thr Asp Ala
                20                  25                  30 act ggt tac gac cg gttagtaaac catcacatac aactaatatt cgatagttaa      198
Thr Gly Tyr Asp Arg
            35 cagttccccc atccag c gcc ctc ttc ccc cat tgg atc acc atc tct ggc     248
                   Ala Leu Phe Pro His Trp Ile Thr Ile Ser Gly
                                40                  45 aac tgc aac acc cgc gag acg gtg ctg aac cgt gac gga acc ggc ctc     296
Asn Cys Asn Thr Arg Glu Thr Val Leu Asn Arg Asp Gly Thr Gly Leu
        50                  55                  60 acg atc ggt agc gac tgc tac ccc agt tcc ggc acc tgg ttc tct ccc     344
Thr Ile Gly Ser Asp Cys Tyr Pro Ser Ser Gly Thr Trp Phe Ser Pro
65                  70                  75 tac gac gga gcc acc tgg act gca gcc tcg gat ttg gac atc gac cac     392
Tyr Asp Gly Ala Thr Trp Thr Ala Ala Ser Asp Leu Asp Ile Asp His
80                  85                  90                  95 gtt gta ccc ctt tcc gat gct tgg aag tcg ggt gca aat ctc tgg          437
Val Val Pro Leu Ser Asp Ala Trp Lys Ser Gly Ala Asn Leu Trp
                100                 105                 110 gtatatatcc gcttttttc ttgtgtgatg gcatcggaaa ttgttaatca atgcctttaa    497 aaag act acc gct cag cgc cag aac ttc gcc aat gac ctc tct aac ccg    546
     Thr Thr Ala Gln Arg Gln Asn Phe Ala Asn Asp Leu Ser Asn Pro
                 115                 120                 125 cag cta atc gcg gtc acg gac aat gtc aac tct gca aag ggt gat aag    594
Gln Leu Ile Ala Val Thr Asp Asn Val Asn Ser Ala Lys Gly Asp Lys
            130                 135                 140 agc cct g gtacgcacct ccctccctcc ctcctctcaa tgattgctgc tgacatcatg    651
Ser Pro atcaaaag at ttg tgg aag ccc ccg ctc tcc tcg tac tac tgc act tac    700
          Asp Leu Trp Lys Pro Pro Leu Ser Ser Tyr Tyr Cys Thr Tyr
             145                 150                 155 gcc aaa atg tgg gtt aag gtc aag agc gtg tac tcg ctg tcg gtg acc    748
Ala Lys Met Trp Val Lys Val Lys Ser Val Tyr Ser Leu Ser Val Thr
        160                 165                 170 tct gct gag aag tcg gct ttg acg tct atg ttg aac acg tgt taa        793
Ser Ala Glu Lys Ser Ala Leu Thr Ser Met Leu Asn Thr Cys
175                 180                 185
```

<210> SEQ ID NO 26
<211> LENGTH: 204
<212> TYPE: PRT
<213> ORGANISM: Trichophaea abundans

<400> SEQUENCE: 26

```
Met Lys Phe Ser Pro Leu Ala Phe Phe Gly Leu Val Ala Ser Val Ser
        -15             -10             -5
Ala Ala Ala Val Glu Lys Arg Thr Pro Pro Asn Ile Pro Ser Thr Thr
-1  1            5                   10              15
Ser Ala Lys Ser Met Leu Ser Gly Leu Asn Ile Arg Thr Thr Asp Ala
                20              25              30
Thr Gly Tyr Asp Arg Ala Leu Phe Pro His Trp Ile Thr Ile Ser Gly
            35              40              45
Asn Cys Asn Thr Arg Glu Thr Val Leu Asn Arg Asp Gly Thr Gly Leu
        50              55              60
Thr Ile Gly Ser Asp Cys Tyr Pro Ser Ser Gly Thr Trp Phe Ser Pro
        65              70              75
Tyr Asp Gly Ala Thr Trp Thr Ala Ala Ser Asp Leu Asp Ile Asp His
80              85              90              95
Val Val Pro Leu Ser Asp Ala Trp Lys Ser Gly Ala Asn Leu Trp Thr
                100             105             110
Thr Ala Gln Arg Gln Asn Phe Ala Asn Asp Leu Ser Asn Pro Gln Leu
                115             120             125
Ile Ala Val Thr Asp Asn Val Asn Ser Ala Lys Gly Asp Lys Ser Pro
                130             135             140
Asp Leu Trp Lys Pro Pro Leu Ser Ser Tyr Tyr Cys Thr Tyr Ala Lys
        145             150             155
Met Trp Val Lys Val Lys Ser Val Tyr Ser Leu Ser Val Thr Ser Ala
160             165             170             175
Glu Lys Ser Ala Leu Thr Ser Met Leu Asn Thr Cys
                180             185

<210> SEQ ID NO 27
<211> LENGTH: 187
<212> TYPE: PRT
<213> ORGANISM: Trichophaea abundans

<400> SEQUENCE: 27

Ala Ala Val Glu Lys Arg Thr Pro Pro Asn Ile Pro Ser Thr Thr Ser
1               5                   10                  15
Ala Lys Ser Met Leu Ser Gly Leu Asn Ile Arg Thr Thr Asp Ala Thr
                20                  25                  30
Gly Tyr Asp Arg Ala Leu Phe Pro His Trp Ile Thr Ile Ser Gly Asn
            35                  40                  45
Cys Asn Thr Arg Glu Thr Val Leu Asn Arg Asp Gly Thr Gly Leu Thr
        50                  55                  60
Ile Gly Ser Asp Cys Tyr Pro Ser Ser Gly Thr Trp Phe Ser Pro Tyr
65                  70                  75                  80
Asp Gly Ala Thr Trp Thr Ala Ala Ser Asp Leu Asp Ile Asp His Val
                85                  90                  95
Val Pro Leu Ser Asp Ala Trp Lys Ser Gly Ala Asn Leu Trp Thr Thr
                100                 105                 110
Ala Gln Arg Gln Asn Phe Ala Asn Asp Leu Ser Asn Pro Gln Leu Ile
                115                 120                 125
Ala Val Thr Asp Asn Val Asn Ser Ala Lys Gly Asp Lys Ser Pro Asp
                130                 135                 140
Leu Trp Lys Pro Pro Leu Ser Ser Tyr Tyr Cys Thr Tyr Ala Lys Met
145                 150                 155                 160
Trp Val Lys Val Lys Ser Val Tyr Ser Leu Ser Val Thr Ser Ala Glu
```

-continued

```
                    165                 170                 175
Lys Ser Ala Leu Thr Ser Met Leu Asn Thr Cys
            180                 185

<210> SEQ ID NO 28
<211> LENGTH: 618
<212> TYPE: DNA
<213> ORGANISM: Pseudoplectania nigrella
<220> FEATURE:
<221> NAME/KEY: sig_peptide
<222> LOCATION: (1)..(54)
<220> FEATURE:
<221> NAME/KEY: CDS
<222> LOCATION: (1)..(615)
<220> FEATURE:
<221> NAME/KEY: mat_peptide
<222> LOCATION: (55)..(615)

<400> SEQUENCE: 28 atg aag ttc tct gtt tcc acc att gtc ttc ggc ctt gtt gcc act tcc      48
Met Lys Phe Ser Val Ser Thr Ile Val Phe Gly Leu Val Ala Thr Ser
            -15                 -10                 -5 tct gct gcc gcc att gaa aag cgg act cct ccc aac atc ccc tcc gcc      96
Ser Ala Ala Ala Ile Glu Lys Arg Thr Pro Pro Asn Ile Pro Ser Ala
        -1  1               5                   10 agc tcc gca aag acc atg ctt gca tcc atc ccc gtc aga acc act gat     144
Ser Ser Ala Lys Thr Met Leu Ala Ser Ile Pro Val Arg Thr Thr Asp
 15                  20                  25                  30 gca act gga tac caa cgc tcc ctt ttc ccc cac tgg atc acc atc tcc     192
Ala Thr Gly Tyr Gln Arg Ser Leu Phe Pro His Trp Ile Thr Ile Ser
                 35                  40                  45 ggt caa tgc aac acc cgt gaa acc gtc ctc aac cgt gac gga acc aac     240
Gly Gln Cys Asn Thr Arg Glu Thr Val Leu Asn Arg Asp Gly Thr Asn
             50                  55                  60 ctt tcc atc ggc agc gat tgc tat ccc gac agt gga acc tgg ttc tca     288
Leu Ser Ile Gly Ser Asp Cys Tyr Pro Asp Ser Gly Thr Trp Phe Ser
         65                  70                  75 gtt tat gac gga gcc acc tgg acc caa gct tct gac ctt gac atc gac     336
Val Tyr Asp Gly Ala Thr Trp Thr Gln Ala Ser Asp Leu Asp Ile Asp
     80                  85                  90 cat gtt gtg cca ctt tcc gac gcc tgg aag tca ggt gcc aat act tgg     384
His Val Val Pro Leu Ser Asp Ala Trp Lys Ser Gly Ala Asn Thr Trp
 95                 100                 105                 110 acc act gcc aag cgc cag gac ttt gca aac gac ttg aca aac ccc cag     432
Thr Thr Ala Lys Arg Gln Asp Phe Ala Asn Asp Leu Thr Asn Pro Gln
                115                 120                 125 ttg att gcg gtt acg gat act gtt aac cag gca aag ggt gat aag agc     480
Leu Ile Ala Val Thr Asp Thr Val Asn Gln Ala Lys Gly Asp Lys Ser
            130                 135                 140 ccg gat gct tgg aag cct cct ctt act aac tac cac tgc acc tac gct     528
Pro Asp Ala Trp Lys Pro Pro Leu Thr Asn Tyr His Cys Thr Tyr Ala
        145                 150                 155 aaa atg tgg gtt aag gtt aaa agt gtt tgg gga ctc tcg gtg acg gct     576
Lys Met Trp Val Lys Val Lys Ser Val Trp Gly Leu Ser Val Thr Ala
    160                 165                 170 ccc gaa aaa agt gct ttg act agt atg ttg aac acc tgt tga             618
Pro Glu Lys Ser Ala Leu Thr Ser Met Leu Asn Thr Cys
175                 180                 185

<210> SEQ ID NO 29
<211> LENGTH: 205
<212> TYPE: PRT
<213> ORGANISM: Pseudoplectania nigrella
```

<400> SEQUENCE: 29

Met Lys Phe Ser Val Ser Thr Ile Val Phe Gly Leu Val Ala Thr Ser
             -15                 -10                  -5

Ser Ala Ala Ala Ile Glu Lys Arg Thr Pro Pro Asn Ile Pro Ser Ala
     -1   1               5                  10

Ser Ser Ala Lys Thr Met Leu Ala Ser Ile Pro Val Arg Thr Thr Asp
 15              20                  25                       30

Ala Thr Gly Tyr Gln Arg Ser Leu Phe Pro His Trp Ile Thr Ile Ser
             35                  40                  45

Gly Gln Cys Asn Thr Arg Glu Thr Val Leu Asn Arg Asp Gly Thr Asn
             50                  55                  60

Leu Ser Ile Gly Ser Asp Cys Tyr Pro Asp Ser Gly Thr Trp Phe Ser
             65                  70                  75

Val Tyr Asp Gly Ala Thr Trp Thr Gln Ala Ser Asp Leu Asp Ile Asp
 80              85                  90

His Val Val Pro Leu Ser Asp Ala Trp Lys Ser Gly Ala Asn Thr Trp
 95             100                 105                      110

Thr Thr Ala Lys Arg Gln Asp Phe Ala Asn Asp Leu Thr Asn Pro Gln
                115                 120                 125

Leu Ile Ala Val Thr Asp Thr Val Asn Gln Ala Lys Gly Asp Lys Ser
                130                 135                 140

Pro Asp Ala Trp Lys Pro Pro Leu Thr Asn Tyr His Cys Thr Tyr Ala
             145                 150                 155

Lys Met Trp Val Lys Val Lys Ser Val Trp Gly Leu Ser Val Thr Ala
            160                 165                 170

Pro Glu Lys Ser Ala Leu Thr Ser Met Leu Asn Thr Cys
175                 180                 185

<210> SEQ ID NO 30
<211> LENGTH: 187
<212> TYPE: PRT
<213> ORGANISM: Pseudoplectania nigrella

<400> SEQUENCE: 30

Ala Ala Ile Glu Lys Arg Thr Pro Pro Asn Ile Pro Ser Ala Ser Ser
 1               5                  10                  15

Ala Lys Thr Met Leu Ala Ser Ile Pro Val Arg Thr Thr Asp Ala Thr
             20                  25                  30

Gly Tyr Gln Arg Ser Leu Phe Pro His Trp Ile Thr Ile Ser Gly Gln
             35                  40                  45

Cys Asn Thr Arg Glu Thr Val Leu Asn Arg Asp Gly Thr Asn Leu Ser
 50                  55                  60

Ile Gly Ser Asp Cys Tyr Pro Asp Ser Gly Thr Trp Phe Ser Val Tyr
 65                  70                  75                  80

Asp Gly Ala Thr Trp Thr Gln Ala Ser Asp Leu Asp Ile Asp His Val
             85                  90                  95

Val Pro Leu Ser Asp Ala Trp Lys Ser Gly Ala Asn Thr Trp Thr Thr
            100                 105                 110

Ala Lys Arg Gln Asp Phe Ala Asn Asp Leu Thr Asn Pro Gln Leu Ile
            115                 120                 125

Ala Val Thr Asp Thr Val Asn Gln Ala Lys Gly Asp Lys Ser Pro Asp
            130                 135                 140

Ala Trp Lys Pro Pro Leu Thr Asn Tyr His Cys Thr Tyr Ala Lys Met
145                 150                 155                 160

-continued

```
Trp Val Lys Val Lys Ser Val Trp Gly Leu Ser Val Thr Ala Pro Glu
                165                 170                 175

Lys Ser Ala Leu Thr Ser Met Leu Asn Thr Cys
        180                 185

<210> SEQ ID NO 31
<211> LENGTH: 957
<212> TYPE: DNA
<213> ORGANISM: Gyromitra esculenta
<220> FEATURE:
<221> NAME/KEY: CDS
<222> LOCATION: (1)..(197)
<220> FEATURE:
<221> NAME/KEY: sig
<222> LOCATION: (1)..(45)
<220> FEATURE:
<221> NAME/KEY: mat_peptide
<222> LOCATION: (46)..(954)
<220> FEATURE:
<221> NAME/KEY: CDS
<222> LOCATION: (255)..(378)
<220> FEATURE:
<221> NAME/KEY: CDS
<222> LOCATION: (448)..(504)
<220> FEATURE:
<221> NAME/KEY: CDS
<222> LOCATION: (585)..(641)
<220> FEATURE:
<221> NAME/KEY: CDS
<222> LOCATION: (703)..(766)
<220> FEATURE:
<221> NAME/KEY: CDS
<222> LOCATION: (845)..(954)

<400> SEQUENCE: 31 atg aag ttc tca atc ttt gcg ctt ttc atc tca gtc gcc gct gcc gct      48
Met Lys Phe Ser Ile Phe Ala Leu Phe Ile Ser Val Ala Ala Ala Ala
-15                 -10                 -5                  -1  1 cca gtt ttg gag aag agg aca ccg ccg aat gtc cct agc gga gct act      96
Pro Val Leu Glu Lys Arg Thr Pro Pro Asn Val Pro Ser Gly Ala Thr
            5                   10                  15 gcc aaa acc ctg ctt acg tct ctg tct gtc agg acc act gat gcc act     144
Ala Lys Thr Leu Leu Thr Ser Leu Ser Val Arg Thr Thr Asp Ala Thr
        20                  25                  30 gga tat gat cgt gac ctt ttc cca cac tgg atc acc cag agc ggt acc     192
Gly Tyr Asp Arg Asp Leu Phe Pro His Trp Ile Thr Gln Ser Gly Thr
    35                  40                  45 tgc aa  gtacgtcccc cagtcggatc tttttttttcc gcccgagtgc tgacggctct     247
Cys Asn
50 gctatag c acc cgc gag gtt gtc ttg aag cgt gat gga act agt gtt gtc   297
          Thr Arg Glu Val Val Leu Lys Arg Asp Gly Thr Ser Val Val
                    55                  60                  65 caa gca agc gat tgt tcg gcc acc agc gga tca tgg ttc agt ccc tac     345
Gln Ala Ser Asp Cys Ser Ala Thr Ser Gly Ser Trp Phe Ser Pro Tyr
        70                  75                  80 gat ggt gct acc tgg aca gct gct tcc gat ctc gtacgctacc cacccccgaa   398
Asp Gly Ala Thr Trp Thr Ala Ala Ser Asp Leu
    85                  90 gaatcattcg tacgtatcgt atcagctaac actgggggaa aaaatccag gac att gac   456
                                                      Asp Ile Asp
                                                                95 cat gtt gtc ccg ctt tct gac gcc tgg aag tct ggc gca aac gcc tgg     504
His Val Val Pro Leu Ser Asp Ala Trp Lys Ser Gly Ala Asn Ala Trp
        100                 105                 110
```

```
gtaattcatt cctcctcctc ctactagtat atgtagcgca ggggggtaac gaactactga      564
caaaaaaaaa aaacgaaaag aca act gcc aaa cgc cag tcc ttt gcc aac gac      617
                     Thr Thr Ala Lys Arg Gln Ser Phe Ala Asn Asp
                             115                 120 ctc aca aac ccc caa cta att gct gtgcgtcccc cactctcatc cctcgaaccc      671
Leu Thr Asn Pro Gln Leu Ile Ala
        125             130 tacaatggcc ctaagaacta aaggtccaca g gtt acc gat aac gtc aac caa         723
                                 Val Thr Asp Asn Val Asn Gln
                                                 135 tcc aaa ggt gac aaa tca cct gac ctt tgg aag cca ccc ctc g              766
Ser Lys Gly Asp Lys Ser Pro Asp Leu Trp Lys Pro Pro Leu
    140             145                 150 gtaagttata tatcattgca atgttagcta catacttggg aaatactaat gttttcccg      826 ggggggggat gggggcag ct tca tat tac tgc aca tac gca tgt atg tgg        876
                      Ala Ser Tyr Tyr Cys Thr Tyr Ala Cys Met Trp
                                  155                 160 gtt aag gtc aag agt gtc tgg gcg ctt tct gtc aca gct gct gag aag        924
Val Lys Val Lys Ser Val Trp Ala Leu Ser Val Thr Ala Ala Glu Lys
            165                 170                 175 tct gcg ctt acg agc atg ctt aat acg tgc tag                            957
Ser Ala Leu Thr Ser Met Leu Asn Thr Cys
    180                 185

<210> SEQ ID NO 32
<211> LENGTH: 203
<212> TYPE: PRT
<213> ORGANISM: Gyromitra esculenta

<400> SEQUENCE: 32

Met Lys Phe Ser Ile Phe Ala Leu Phe Ile Ser Val Ala Ala Ala
-15                 -10                 -5                  -1   1

Pro Val Leu Glu Lys Arg Thr Pro Pro Asn Val Pro Ser Gly Ala Thr
                 5                  10                  15

Ala Lys Thr Leu Leu Thr Ser Leu Ser Val Arg Thr Thr Asp Ala Thr
            20                  25                  30

Gly Tyr Asp Arg Asp Leu Phe Pro His Trp Ile Thr Gln Ser Gly Thr
        35                  40                  45

Cys Asn Thr Arg Glu Val Val Leu Lys Arg Asp Gly Thr Ser Val Val
50                  55                  60                  65

Gln Ala Ser Asp Cys Ser Ala Thr Ser Gly Ser Trp Phe Ser Pro Tyr
                70                  75                  80

Asp Gly Ala Thr Trp Thr Ala Ala Ser Asp Leu Asp Ile Asp His Val
            85                  90                  95

Val Pro Leu Ser Asp Ala Trp Lys Ser Gly Ala Asn Ala Trp Thr Thr
        100                 105                 110

Ala Lys Arg Gln Ser Phe Ala Asn Asp Leu Thr Asn Pro Gln Leu Ile
    115                 120                 125

Ala Val Thr Asp Asn Val Asn Gln Ser Lys Gly Asp Lys Ser Pro Asp
130                 135                 140                 145

Leu Trp Lys Pro Pro Leu Ala Ser Tyr Tyr Cys Thr Tyr Ala Cys Met
                150                 155                 160

Trp Val Lys Val Lys Ser Val Trp Ala Leu Ser Val Thr Ala Ala Glu
            165                 170                 175

Lys Ser Ala Leu Thr Ser Met Leu Asn Thr Cys
    180                 185
```

<210> SEQ ID NO 33
<211> LENGTH: 188
<212> TYPE: PRT
<213> ORGANISM: Gyromitra esculenta

<400> SEQUENCE: 33

Ala Pro Val Leu Glu Lys Arg Thr Pro Pro Asn Val Pro Ser Gly Ala
1               5                   10                  15

Thr Ala Lys Thr Leu Leu Thr Ser Leu Ser Val Arg Thr Thr Asp Ala
            20                  25                  30

Thr Gly Tyr Asp Arg Asp Leu Phe Pro His Trp Ile Thr Gln Ser Gly
        35                  40                  45

Thr Cys Asn Thr Arg Glu Val Val Leu Lys Arg Asp Gly Thr Ser Val
    50                  55                  60

Val Gln Ala Ser Asp Cys Ser Ala Thr Ser Gly Ser Trp Phe Ser Pro
65                  70                  75                  80

Tyr Asp Gly Ala Thr Trp Thr Ala Ala Ser Asp Leu Asp Ile Asp His
                85                  90                  95

Val Val Pro Leu Ser Asp Ala Trp Lys Ser Gly Ala Asn Ala Trp Thr
            100                 105                 110

Thr Ala Lys Arg Gln Ser Phe Ala Asn Asp Leu Thr Asn Pro Gln Leu
        115                 120                 125

Ile Ala Val Thr Asp Asn Val Asn Gln Ser Lys Gly Asp Lys Ser Pro
    130                 135                 140

Asp Leu Trp Lys Pro Pro Leu Ala Ser Tyr Tyr Cys Thr Tyr Ala Cys
145                 150                 155                 160

Met Trp Val Lys Val Lys Ser Val Trp Ala Leu Ser Val Thr Ala Ala
                165                 170                 175

Glu Lys Ser Ala Leu Thr Ser Met Leu Asn Thr Cys
            180                 185

<210> SEQ ID NO 34
<211> LENGTH: 904
<212> TYPE: DNA
<213> ORGANISM: Morchella esculenta
<220> FEATURE:
<221> NAME/KEY: CDS
<222> LOCATION: (1)..(197)
<220> FEATURE:
<221> NAME/KEY: sig_peptide
<222> LOCATION: (1)..(45)
<220> FEATURE:
<221> NAME/KEY: mat_peptide
<222> LOCATION: (46)..(901)
<220> FEATURE:
<221> NAME/KEY: CDS
<222> LOCATION: (247)..(370)
<220> FEATURE:
<221> NAME/KEY: CDS
<222> LOCATION: (488)..(601)
<220> FEATURE:
<221> NAME/KEY: CDS
<222> LOCATION: (655)..(718)
<220> FEATURE:
<221> NAME/KEY: CDS
<222> LOCATION: (792)..(901)

<400> SEQUENCE: 34 atg aag ctc aca gca gta gtc ctc ttc ttc acg acc gct ctc gca gct      48
Met Lys Leu Thr Ala Val Val Leu Phe Phe Thr Thr Ala Leu Ala Ala
-15                 -10                 -5                  -1   1 cct acg cta gag aag cgg act cct cct aat att cct act gcc gct tcc      96
Pro Thr Leu Glu Lys Arg Thr Pro Pro Asn Ile Pro Thr Ala Ala Ser

```
                  5                  10                   15
gcg aag act atg ctt gac gct ctc aca aca agg acc aca gat gcc act       144
Ala Lys Thr Met Leu Asp Ala Leu Thr Thr Arg Thr Thr Asp Ala Thr
         20                  25                  30 ggt tac tcc cgt gat ctc ttc ccg cat tgg att acc cag agc ggg tct       192
Gly Tyr Ser Arg Asp Leu Phe Pro His Trp Ile Thr Gln Ser Gly Ser
     35                  40                  45 tgc aa  gtaaggcatc tggtaatcat tcataagatt cattcctgac aaagagtag t       247
Cys Asn
50 acc cgt gag gta gtt ctt gcc cgc gat gga tcc agc gtg gtc cag gcc       295
Thr Arg Glu Val Val Leu Ala Arg Asp Gly Ser Ser Val Val Gln Ala
             55                  60                  65 agt gac tgc tca gcc tcg agc ggg acc tgg ttt tcc cct tac gac ggt       343
Ser Asp Cys Ser Ala Ser Ser Gly Thr Trp Phe Ser Pro Tyr Asp Gly
         70                  75                  80 gcg acc tgg acc gct gca tct gat ctt gtaagttttc attacaacat             390
Ala Thr Trp Thr Ala Ala Ser Asp Leu
     85                  90 gcagtttgag atttgcataa gatgctcgcc gggaaattaa agcccgtcga tatatttttg     450
ttttggcggt aggcactgac acatccggcc atttcag gac att gat cat gtt gtg     505
                                        Asp Ile Asp His Val Val
                                                            95 cct ctc tct gat gca tgg aag tcc ggg gcc gac acc tgg act aca gcc       553
Pro Leu Ser Asp Ala Trp Lys Ser Gly Ala Asp Thr Trp Thr Thr Ala
    100                 105                 110 aga cgt caa acc ttt gcc aac gat ctc acg aat ccc cag ttg atc gcc       601
Arg Arg Gln Thr Phe Ala Asn Asp Leu Thr Asn Pro Gln Leu Ile Ala
115                 120                 125                 130 gtaagtcaat tctcccctac ttcgagggaa cataaactga tggtgtggtt cag gtc       657
                                                            Val acc gat aat gta aat cag gcg aag ggt gat aag tcg cct gat gcg tgg       705
Thr Asp Asn Val Asn Gln Ala Lys Gly Asp Lys Ser Pro Asp Ala Trp
        135                 140                 145 aaa ccg cct ctt a gtaagttttt tccattcggc tttttttttt ttttttagc          758
Lys Pro Pro Leu
        150 taaaagagaa ctaaccctaa tatttgtgtc cag ca  tcg tac tac tgc act tat     811
                                        Thr Ser Tyr Tyr Cys Thr Tyr
                                                            155 gca agg atg tgg gtt aag gtg aag agt gtg tat tcg ttg tct gtg acc       859
Ala Arg Met Trp Val Lys Val Lys Ser Val Tyr Ser Leu Ser Val Thr
    160                 165                 170 tca gct gag aag acg gca ttg acg agt atg ttg aac acg tgc tga           904
Ser Ala Glu Lys Thr Ala Leu Thr Ser Met Leu Asn Thr Cys
175                 180                 185

<210> SEQ ID NO 35
<211> LENGTH: 203
<212> TYPE: PRT
<213> ORGANISM: Morchella esculenta

<400> SEQUENCE: 35

Met Lys Leu Thr Ala Val Val Leu Phe Phe Thr Thr Ala Leu Ala Ala
-15                 -10                 -5                -1  1

Pro Thr Leu Glu Lys Arg Thr Pro Pro Asn Ile Pro Thr Ala Ala Ser
             5                  10                  15

Ala Lys Thr Met Leu Asp Ala Leu Thr Thr Arg Thr Thr Asp Ala Thr
         20                  25                  30
```

```
Gly Tyr Ser Arg Asp Leu Phe Pro His Trp Ile Thr Gln Ser Gly Ser
        35                  40                  45

Cys Asn Thr Arg Glu Val Val Leu Ala Arg Asp Gly Ser Ser Val Val
 50                  55                  60                  65

Gln Ala Ser Asp Cys Ser Ala Ser Ser Gly Thr Trp Phe Ser Pro Tyr
                 70                  75                  80

Asp Gly Ala Thr Trp Thr Ala Ala Ser Asp Leu Asp Ile Asp His Val
             85                  90                  95

Val Pro Leu Ser Asp Ala Trp Lys Ser Gly Ala Asp Thr Trp Thr Thr
            100                 105                 110

Ala Arg Arg Gln Thr Phe Ala Asn Asp Leu Thr Asn Pro Gln Leu Ile
        115                 120                 125

Ala Val Thr Asp Asn Val Asn Gln Ala Lys Gly Asp Lys Ser Pro Asp
130                 135                 140                 145

Ala Trp Lys Pro Pro Leu Thr Ser Tyr Tyr Cys Thr Tyr Ala Arg Met
                150                 155                 160

Trp Val Lys Val Lys Ser Val Tyr Ser Leu Ser Val Thr Ser Ala Glu
            165                 170                 175

Lys Thr Ala Leu Thr Ser Met Leu Asn Thr Cys
        180                 185

<210> SEQ ID NO 36
<211> LENGTH: 188
<212> TYPE: PRT
<213> ORGANISM: Morchella esculenta

<400> SEQUENCE: 36

Ala Pro Thr Leu Glu Lys Arg Thr Pro Pro Asn Ile Pro Thr Ala Ala
 1               5                  10                  15

Ser Ala Lys Thr Met Leu Asp Ala Leu Thr Thr Arg Thr Thr Asp Ala
             20                  25                  30

Thr Gly Tyr Ser Arg Asp Leu Phe Pro His Trp Ile Thr Gln Ser Gly
         35                  40                  45

Ser Cys Asn Thr Arg Glu Val Val Leu Ala Arg Asp Gly Ser Ser Val
     50                  55                  60

Val Gln Ala Ser Asp Cys Ser Ala Ser Ser Gly Thr Trp Phe Ser Pro
 65                  70                  75                  80

Tyr Asp Gly Ala Thr Trp Thr Ala Ala Ser Asp Leu Asp Ile Asp His
                 85                  90                  95

Val Val Pro Leu Ser Asp Ala Trp Lys Ser Gly Ala Asp Thr Trp Thr
            100                 105                 110

Thr Ala Arg Arg Gln Thr Phe Ala Asn Asp Leu Thr Asn Pro Gln Leu
        115                 120                 125

Ile Ala Val Thr Asp Asn Val Asn Gln Ala Lys Gly Asp Lys Ser Pro
130                 135                 140

Asp Ala Trp Lys Pro Pro Leu Thr Ser Tyr Tyr Cys Thr Tyr Ala Arg
145                 150                 155                 160

Met Trp Val Lys Val Lys Ser Val Tyr Ser Leu Ser Val Thr Ser Ala
                165                 170                 175

Glu Lys Thr Ala Leu Thr Ser Met Leu Asn Thr Cys
            180                 185

<210> SEQ ID NO 37
<211> LENGTH: 905
<212> TYPE: DNA
```

```
<213> ORGANISM: Morchella crassipes
<220> FEATURE:
<221> NAME/KEY: CDS
<222> LOCATION: (1)..(197)
<220> FEATURE:
<221> NAME/KEY: sig_peptide
<222> LOCATION: (1)..(45)
<220> FEATURE:
<221> NAME/KEY: mat_peptide
<222> LOCATION: (46)..(902)
<220> FEATURE:
<221> NAME/KEY: CDS
<222> LOCATION: (247)..(370)
<220> FEATURE:
<221> NAME/KEY: CDS
<222> LOCATION: (488)..(601)
<220> FEATURE:
<221> NAME/KEY: CDS
<222> LOCATION: (655)..(718)
<220> FEATURE:
<221> NAME/KEY: CDS
<222> LOCATION: (793)..(902)

<400> SEQUENCE: 37
```

```
atg aag ctc aca gca gta gtc ctc ttt ttc acg acc gct ctc gca gct      48
Met Lys Leu Thr Ala Val Val Leu Phe Phe Thr Thr Ala Leu Ala Ala
-15             -10                 -5                  -1   1 cct acg cta gag aag cgg act cct ccc aat att ccc act gcc gct tcc      96
Pro Thr Leu Glu Lys Arg Thr Pro Pro Asn Ile Pro Thr Ala Ala Ser
                5                  10                  15 gcg aag act atg ctt gac gct ctc aca aca agg act aca gat gct act     144
Ala Lys Thr Met Leu Asp Ala Leu Thr Thr Arg Thr Thr Asp Ala Thr
            20                  25                  30 ggt tac tcc cgt gat ctc ttc ccg cat tgg att acc cag agc ggg tct     192
Gly Tyr Ser Arg Asp Leu Phe Pro His Trp Ile Thr Gln Ser Gly Ser
        35                  40                  45 tgc aa  gtaaggcatc tggtaatcat tcataaggtt cattcctgac aaagagtag t     247
Cys Asn
50 acc cgt gag gta gtt ctt gcc cgc gat gga tcc agc gtg gtc cag gcc     295
Thr Arg Glu Val Val Leu Ala Arg Asp Gly Ser Ser Val Val Gln Ala
                55                  60                  65 agt gac tgc tca gcc tcg agc ggg acc tgg ttt tcc cct tac gac ggt     343
Ser Asp Cys Ser Ala Ser Ser Gly Thr Trp Phe Ser Pro Tyr Asp Gly
        70                  75                  80 gcg acc tgg acc gct gca tct gat ctt gtaagttttc attacaacat           390
Ala Thr Trp Thr Ala Ala Ser Asp Leu
85                  90 gcagtttgag atttgcataa gatgctcgct gggaaattaa agctcgtcga tatattttg    450 ttttggcggt aggcactgac acatccggcc atttcag gac att gat cat gtt gtg    505
                                        Asp Ile Asp His Val Val
                                                        95 cct ctc tct gat gca tgg aag tcc ggg gcc gac acc tgg act aca gcc     553
Pro Leu Ser Asp Ala Trp Lys Ser Gly Ala Asp Thr Trp Thr Thr Ala
    100                 105                 110 aaa cgt caa acc ttt gcc aac gat ctc acg aat ccc cag ttg atc gcc     601
Lys Arg Gln Thr Phe Ala Asn Asp Leu Thr Asn Pro Gln Leu Ile Ala
115                 120                 125                 130 gtaagtcaat tctcccctac ttcgagggaa cataaactga tggtgtggtt cag gtc      657
                                                            Val acc gat aat gta aat cag gcg aag ggt gat aag tcg cct gat gcg tgg     705
Thr Asp Asn Val Asn Gln Ala Lys Gly Asp Lys Ser Pro Asp Ala Trp
                135                 140                 145 aaa ccg cct ctt a gtaagttttt tttcattcgg cttttttttt ttttttttag       758
Lys Pro Pro Leu
```

```
Lys Pro Pro Leu
        150 ctaaaagaga accaaccta atatttgtgt ccag ca  tcg tac tac tgc act tat       812
                                        Thr Ser Tyr Tyr Cys Thr Tyr
                                                    155 gca agg atg tgg gtt aag gtg aag agt gtg tat tcg ttg tct gtg acc         860
Ala Arg Met Trp Val Lys Val Lys Ser Val Tyr Ser Leu Ser Val Thr
160                 165                 170 tca gct gag aag acg gca ttg acg agt atg ttg aac acg tgc tga             905
Ser Ala Glu Lys Thr Ala Leu Thr Ser Met Leu Asn Thr Cys
175                 180                 185

<210> SEQ ID NO 38
<211> LENGTH: 203
<212> TYPE: PRT
<213> ORGANISM: Morchella crassipes

<400> SEQUENCE: 38

Met Lys Leu Thr Ala Val Val Leu Phe Phe Thr Thr Ala Leu Ala Ala
-15                 -10                 -5                  -1  1

Pro Thr Leu Glu Lys Arg Thr Pro Asn Ile Pro Thr Ala Ala Ser
            5                   10                  15

Ala Lys Thr Met Leu Asp Ala Leu Thr Thr Arg Thr Thr Asp Ala Thr
                20                  25                  30

Gly Tyr Ser Arg Asp Leu Phe Pro His Trp Ile Thr Gln Ser Gly Ser
        35                  40                  45

Cys Asn Thr Arg Glu Val Val Leu Ala Arg Asp Gly Ser Ser Val Val
50                  55                  60                  65

Gln Ala Ser Asp Cys Ser Ala Ser Ser Gly Thr Trp Phe Ser Pro Tyr
                70                  75                  80

Asp Gly Ala Thr Trp Thr Ala Ala Ser Asp Leu Asp Ile Asp His Val
            85                  90                  95

Val Pro Leu Ser Asp Ala Trp Lys Ser Gly Ala Asp Thr Trp Thr Thr
            100                 105                 110

Ala Lys Arg Gln Thr Phe Ala Asn Asp Leu Thr Asn Pro Gln Leu Ile
    115                 120                 125

Ala Val Thr Asp Asn Val Asn Gln Ala Lys Gly Asp Lys Ser Pro Asp
130                 135                 140                 145

Ala Trp Lys Pro Pro Leu Thr Ser Tyr Tyr Cys Thr Tyr Ala Arg Met
                150                 155                 160

Trp Val Lys Val Lys Ser Val Tyr Ser Leu Ser Val Thr Ser Ala Glu
            165                 170                 175

Lys Thr Ala Leu Thr Ser Met Leu Asn Thr Cys
        180                 185

<210> SEQ ID NO 39
<211> LENGTH: 188
<212> TYPE: PRT
<213> ORGANISM: Morchella crassipes

<400> SEQUENCE: 39

Ala Pro Thr Leu Glu Lys Arg Thr Pro Asn Ile Pro Thr Ala Ala
1               5                   10                  15

Ser Ala Lys Thr Met Leu Asp Ala Leu Thr Thr Arg Thr Thr Asp Ala
                20                  25                  30

Thr Gly Tyr Ser Arg Asp Leu Phe Pro His Trp Ile Thr Gln Ser Gly
        35                  40                  45
```

-continued

```
Ser Cys Asn Thr Arg Glu Val Val Leu Ala Arg Asp Gly Ser Ser Val
    50                  55                  60

Val Gln Ala Ser Asp Cys Ser Ala Ser Ser Gly Thr Trp Phe Ser Pro
 65                  70                  75                  80

Tyr Asp Gly Ala Thr Trp Thr Ala Ala Ser Asp Leu Asp Ile Asp His
                 85                  90                  95

Val Val Pro Leu Ser Asp Ala Trp Lys Ser Gly Ala Asp Thr Trp Thr
                100                 105                 110

Thr Ala Lys Arg Gln Thr Phe Ala Asn Asp Leu Thr Asn Pro Gln Leu
            115                 120                 125

Ile Ala Val Thr Asp Asn Val Asn Gln Ala Lys Gly Asp Lys Ser Pro
130                 135                 140

Asp Ala Trp Lys Pro Pro Leu Thr Ser Tyr Tyr Cys Thr Tyr Ala Arg
145                 150                 155                 160

Met Trp Val Lys Val Lys Ser Val Tyr Ser Leu Ser Val Thr Ser Ala
                165                 170                 175

Glu Lys Thr Ala Leu Thr Ser Met Leu Asn Thr Cys
            180                 185
```

```
<210> SEQ ID NO 40
<211> LENGTH: 841
<212> TYPE: DNA
<213> ORGANISM: Disciotis venosa
<220> FEATURE:
<221> NAME/KEY: CDS
<222> LOCATION: (1)..(197)
<220> FEATURE:
<221> NAME/KEY: sig_peptide
<222> LOCATION: (1)..(45)
<220> FEATURE:
<221> NAME/KEY: mat_peptide
<222> LOCATION: (46)..(838)
<220> FEATURE:
<221> NAME/KEY: CDS
<222> LOCATION: (253)..(376)
<220> FEATURE:
<221> NAME/KEY: CDS
<222> LOCATION: (438)..(551)
<220> FEATURE:
<221> NAME/KEY: CDS
<222> LOCATION: (607)..(670)
<220> FEATURE:
<221> NAME/KEY: CDS
<222> LOCATION: (729)..(838)
```

<400> SEQUENCE: 40

```
atg aag ctc tct gct att gtc att ttt atc tca gcc gtt gct gct gct         48
Met Lys Leu Ser Ala Ile Val Ile Phe Ile Ser Ala Val Ala Ala Ala
-15                 -10                 -5                  -1   1 cca gct ttg gag aag agg act ccc cca aac att ccc act gcg gca tct         96
Pro Ala Leu Glu Lys Arg Thr Pro Pro Asn Ile Pro Thr Ala Ala Ser
            5                   10                  15 gca aag act ttg ctt gct gca ttg acc act agg act act gat gcc acc        144
Ala Lys Thr Leu Leu Ala Ala Leu Thr Thr Arg Thr Thr Asp Ala Thr
        20                  25                  30 ggg tat gat cgt gat ctt ttc cct cac tgg att acc cag agc gga tcc        192
Gly Tyr Asp Arg Asp Leu Phe Pro His Trp Ile Thr Gln Ser Gly Ser
 35                  40                  45 tgc aa gtaagttaat ggaacgccta acacctccaa ctactctcta atatttccat          247
Cys Asn
 50 cttag c acc cgc gag gtt gtc ctg gca cgc gat gga acc aat gtc gtc        295
        Thr Arg Glu Val Val Leu Ala Arg Asp Gly Thr Asn Val Val
                    55                  60                  65
```

```
cag gcc agc gat tgc tct gct tca agt ggg aca tgg ttc tcc ccc tac      343
Gln Ala Ser Asp Cys Ser Ala Ser Ser Gly Thr Trp Phe Ser Pro Tyr
                 70                  75                  80 gat ggt gct aca tgg act gct gcc tca gat ctc gtatgtaacc caattgagta    396
Asp Gly Ala Thr Trp Thr Ala Ala Ser Asp Leu
             85                  90 attgtgctag atatcgtatt aacagtgccg cctgaatcta g gac att gac cac gtt    452
                                              Asp Ile Asp His Val
                                                              95 gtc cca ctt tcg gat gcc tgg aag tct ggt gcg gga acc tgg acc act      500
Val Pro Leu Ser Asp Ala Trp Lys Ser Gly Ala Gly Thr Trp Thr Thr
                100                 105                 110 gct aag cgt caa tca ttc gcc aac gac ctt aca aac ccc cag ctg att      548
Ala Lys Arg Gln Ser Phe Ala Asn Asp Leu Thr Asn Pro Gln Leu Ile
            115                 120                 125 gct gtaagccaca ttatactccc caagttggtg catcgactaa gctgatatct ctcag     606
Ala
130 gtt acc gac aac gtc aac caa gcc aag ggt gac aag tcc ccc gac gcc      654
Val Thr Asp Asn Val Asn Gln Ala Lys Gly Asp Lys Ser Pro Asp Ala
                135                 140                 145 tgg aag ccc cct ctc a gtaagccgcc tcatcacctg cctcttgggc tgagtaaata   710
Trp Lys Pro Pro Leu
            150 ctaacattag ttttctag cc tca tac tac tgc acc tac gcc cgt atg tgg       760
                       Thr Ser Tyr Tyr Cys Thr Tyr Ala Arg Met Trp
                                       155                 160 gtc aag gtc aag agt gtc tgg gaa ctc tct gtc acc gcg gct gag agg      808
Val Lys Val Lys Ser Val Trp Glu Leu Ser Val Thr Ala Ala Glu Arg
            165                 170                 175 act gcc ctc acg agc atg ctc aac aca tgc tag                          841
Thr Ala Leu Thr Ser Met Leu Asn Thr Cys
            180                 185

<210> SEQ ID NO 41
<211> LENGTH: 203
<212> TYPE: PRT
<213> ORGANISM: Disciotis venosa

<400> SEQUENCE: 41

Met Lys Leu Ser Ala Ile Val Ile Phe Ile Ser Ala Val Ala Ala Ala
-15                 -10                 -5                  -1  1

Pro Ala Leu Glu Lys Arg Thr Pro Pro Asn Ile Pro Thr Ala Ala Ser
                5                   10                  15

Ala Lys Thr Leu Leu Ala Ala Leu Thr Thr Arg Thr Thr Asp Ala Thr
            20                  25                  30

Gly Tyr Asp Arg Asp Leu Phe Pro His Trp Ile Thr Gln Ser Gly Ser
        35                  40                  45

Cys Asn Thr Arg Glu Val Val Leu Ala Arg Asp Gly Thr Asn Val Val
50                  55                  60                  65

Gln Ala Ser Asp Cys Ser Ala Ser Ser Gly Thr Trp Phe Ser Pro Tyr
                70                  75                  80

Asp Gly Ala Thr Trp Thr Ala Ala Ser Asp Leu Asp Ile Asp His Val
            85                  90                  95

Val Pro Leu Ser Asp Ala Trp Lys Ser Gly Ala Gly Thr Trp Thr Thr
        100                 105                 110

Ala Lys Arg Gln Ser Phe Ala Asn Asp Leu Thr Asn Pro Gln Leu Ile
    115                 120                 125
```

Ala Val Thr Asp Asn Val Asn Gln Ala Lys Gly Asp Lys Ser Pro Asp
130                 135                 140                 145

Ala Trp Lys Pro Pro Leu Thr Ser Tyr Tyr Cys Thr Tyr Ala Arg Met
            150                 155                 160

Trp Val Lys Val Lys Ser Val Trp Glu Leu Ser Val Thr Ala Ala Glu
        165                 170                 175

Arg Thr Ala Leu Thr Ser Met Leu Asn Thr Cys
        180                 185

<210> SEQ ID NO 42
<211> LENGTH: 188
<212> TYPE: PRT
<213> ORGANISM: Disciotis venosa

<400> SEQUENCE: 42

Ala Pro Ala Leu Glu Lys Arg Thr Pro Pro Asn Ile Pro Thr Ala Ala
1               5                   10                  15

Ser Ala Lys Thr Leu Leu Ala Ala Leu Thr Thr Arg Thr Thr Asp Ala
            20                  25                  30

Thr Gly Tyr Asp Arg Asp Leu Phe Pro His Trp Ile Thr Gln Ser Gly
        35                  40                  45

Ser Cys Asn Thr Arg Glu Val Val Leu Ala Arg Asp Gly Thr Asn Val
    50                  55                  60

Val Gln Ala Ser Asp Cys Ser Ala Ser Ser Gly Thr Trp Phe Ser Pro
65                  70                  75                  80

Tyr Asp Gly Ala Thr Trp Thr Ala Ser Asp Leu Asp Ile Asp His
                85                  90                  95

Val Val Pro Leu Ser Asp Ala Trp Lys Ser Gly Ala Gly Thr Trp Thr
            100                 105                 110

Thr Ala Lys Arg Gln Ser Phe Ala Asn Asp Leu Thr Asn Pro Gln Leu
        115                 120                 125

Ile Ala Val Thr Asp Asn Val Asn Gln Ala Lys Gly Asp Lys Ser Pro
130                 135                 140

Asp Ala Trp Lys Pro Pro Leu Thr Ser Tyr Tyr Cys Thr Tyr Ala Arg
145                 150                 155                 160

Met Trp Val Lys Val Lys Ser Val Trp Glu Leu Ser Val Thr Ala Ala
                165                 170                 175

Glu Arg Thr Ala Leu Thr Ser Met Leu Asn Thr Cys
            180                 185

<210> SEQ ID NO 43
<211> LENGTH: 5
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: X=E (Glu), D (Asp), H (His)
<220> FEATURE:
<221> NAME/KEY: MISC_FEATURE
<222> LOCATION: (3)..(3)
<223> OTHER INFORMATION: X=I (Ile), V (Val), L (Leu), F (Phe), M (Met)
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(5)

<223> OTHER INFORMATION: X=P (Pro), A (Ala), S (Ser)

<400> SEQUENCE: 43

Xaa His Xaa Xaa Xaa
1               5

<210> SEQ ID NO 44
<211> LENGTH: 5
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: X= T (Tyr), D (Asp), S (Ser)
<220> FEATURE:
<221> NAME/KEY: MISC_FEATURE
<222> LOCATION: (2)..(2)
<223> OTHER INFORMATION: X= G (Gly), N (Asn)

<400> SEQUENCE: 44

Xaa Xaa Pro Gln Leu
1               5

<210> SEQ ID NO 45
<211> LENGTH: 5
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: X= F (Phe), L (Leu), Y (Tyr), I (Ile)
<220> FEATURE:
<221> NAME/KEY: MISC_FEATURE
<222> LOCATION: (3)..(3)
<223> OTHER INFORMATION: X= N (Asn), R (Arg)
<220> FEATURE:
<221> NAME/KEY: MISC_FEATURE
<222> LOCATION: (5)..(5)
<223> OTHER INFORMATION: X= L (leu), I (Ile), P (Pro), V (Val)

<400> SEQUENCE: 45

Xaa Ala Xaa Asp Xaa
1               5

<210> SEQ ID NO 46
<211> LENGTH: 4
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (2)..(2)
<223> OTHER INFORMATION: X= Asp (D), Asn (N)
<220> FEATURE:
<221> NAME/KEY: MISC_FEATURE
<222> LOCATION: (4)..(4)
<223> OTHER INFORMATION: X= A (Ala), R (Arg)

<400> SEQUENCE: 46

Cys Xaa Thr Xaa
1

<210> SEQ ID NO 47
<211> LENGTH: 4
<212> TYPE: PRT
<213> ORGANISM: Artificial

```
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: X= D (Asp), Q (Gln)
<220> FEATURE:
<221> NAME/KEY: MISC_FEATURE
<222> LOCATION: (2)..(2)
<223> OTHER INFORMATION: X= I (Ile), V (Val)

<400> SEQUENCE: 47

Xaa Xaa Asp His
1

<210> SEQ ID NO 48
<211> LENGTH: 8
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (3)..(3)
<223> OTHER INFORMATION: X=T (Thr), S (Ser)
<220> FEATURE:
<221> NAME/KEY: MISC_FEATURE
<222> LOCATION: (4)..(4)
<223> OTHER INFORMATION: X=D (Asp), N (Asn)
<220> FEATURE:
<221> NAME/KEY: MISC_FEATURE
<222> LOCATION: (5)..(5)
<223> OTHER INFORMATION: X=A (Ala), P (Pro)
<220> FEATURE:
<221> NAME/KEY: MISC_FEATURE
<222> LOCATION: (6)..(6)
<223> OTHER INFORMATION: X=T (Thr), D (Asp), P (Pro), S (Ser)

<400> SEQUENCE: 48

Arg Thr Xaa Xaa Xaa Xaa Gly Tyr
1               5
```

POLYPEPTIDES HAVING DNASE ACTIVITY

CROSS-REFERENCE TO RELATED APPLICATIONS

This application is a 35 U.S.C. 371 national application of international application no. PCT/CN2018/080156 filed Mar. 23, 2018 which claims priority or the benefit under 35 U.S.C. 119 of European application no. 17164340.6 filed Mar. 31, 2017, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to polypeptides having DNase activity and polynucleotides encoding the polypeptides. The invention also relates to nucleic acid constructs, vectors, and host cells comprising the polynucleotides as well as methods of producing and using the polypeptides.

Description of the Related Art

Enzymes have been used in detergents for decades. Usually a cocktail of various enzymes is added to detergent compositions. The enzyme cocktail often comprises various enzymes, wherein each enzyme targets its specific substrate e.g. amylases are active towards starch stains, proteases on protein stains and so forth. Textiles and surfaces such as laundry and dishes become soiled with many different types of soiling. The soiling may be composed of proteins, grease, starch etc. One type of soiling comes from organic matter such as biofilm. The presence of biofilm provides several disadvantages. Biofilm comprises an extracellular polymeric matrix, composed of polysaccharides, extracellular DNA (eDNA), and proteins. The extracellular polymeric matrix may be sticky or glueing, which when present on textile, gives rise to redeposition or backstaining of soil resulting in a greying of the textile. Another drawback is that malodor may be trapped within the organic structure. Organic matter such as biofilm is therefore not desirable in textiles and surfaces associated with cleaning such as washing machines etc. As organic soiling is a complex mixture of polysaccharides, proteins, DNA etc. there is a need for enzymes which effectively prevent, remove or reduce components of such soiling e.g. DNA on items such of fabrics.

SUMMARY OF THE INVENTION

The present invention relates to polypeptides having DNase activity. In particular the invention relates to polypeptides of the RTTDA clade having DNase activity, wherein the polypeptide is selected from the group consisting of:
(a) a polypeptide having at least 80% sequence identity to the polypeptide of SEQ ID NO: 3;
(b) a polypeptide having at least 80% sequence identity to the polypeptide of SEQ ID NO: 6;
(c) a polypeptide having at least 80% sequence identity to the polypeptide of SEQ ID NO: 9;
(d) a polypeptide having at least 80% sequence identity to the polypeptide of SEQ ID NO: 12;
(e) a polypeptide having at least 80% sequence identity to the polypeptide of SEQ ID NO: 15;
(f) a polypeptide having at least 80% sequence identity to the polypeptide of SEQ ID NO: 18;
(g) a polypeptide having at least 80% sequence identity to the polypeptide of SEQ ID NO: 21;
(h) a polypeptide having at least 80% sequence identity to the polypeptide of SEQ ID NO: 24;
(i) a polypeptide having at least 80% sequence identity to the polypeptide of SEQ ID NO: 27;
(j) a polypeptide having at least 80% sequence identity to the polypeptide of SEQ ID NO: 30;
(k) a polypeptide having at least 80% sequence identity to the polypeptide of SEQ ID NO: 33;
(l) a polypeptide having at least 80% sequence identity to the polypeptide of SEQ ID NO: 36;
(m) a polypeptide having at least 80% sequence identity to the polypeptide of SEQ ID NO: 39;
(n) a polypeptide having at least 80% sequence identity to the polypeptide of SEQ ID NO: 42;
(o) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39 and SEQ ID NO: 42, wherein the variant has DNase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions;
(p) a polypeptide comprising the polypeptide of (a) to (n) and a N-terminal and/or C-terminal His-tag and/or HQ-tag;
(q) a polypeptide comprising the polypeptide of (a) to (n) and a N-terminal and/or C-terminal extension of between 1 and 10 amino acids;
(r) a fragment of the polypeptide of (a) to (n) having DNase activity and having at least 90% of the length of the mature polypeptide; and
(s) a polypeptide comprising the motif RT[TS][DN][AP][TDPS]GY (SEQ ID NO: 48).

The invention further relates to a composition e.g. a cleaning or detergent composition, an automatic dish wash (ADVV) composition, a laundry composition, comprising a polypeptide according to the invention.

The invention further relates to use of a polypeptide according to the invention for deep cleaning of an item, such as textile e.g. fabric. The invention further relates to the use of a DNase according to the invention,
(i) for preventing, reducing or removing stickiness of the item;
(ii) for pretreating stains on the item;
(iii) for preventing, reducing or removing redeposition of soil during a wash cycle;
(iv) for preventing, reducing or removing adherence of soil to the item;
(v) for maintaining or improving whiteness of the item;
(vi) for preventing, reducing or removal malodor from the item,
wherein the item is a textile.

The invention also relates to a method for laundering an item comprising the steps of:

a. Exposing an item to a wash liquor comprising a polypeptide according to the invention or a cleaning composition comprising a polypeptide according to the invention;
b. Completing at least one wash cycle; and
c. Optionally rinsing the item,
wherein the item is a textile.

The invention further relates to a polynucleotide encoding the polypeptide of the invention, and a nucleic acid construct or expression vector comprising a polynucleotide encoding a polypeptide of the invention, which is operably linked to one or more control sequences that direct the production of the polypeptide in an expression host. The invention further relates to a recombinant host cell comprising a polynucleotide encoding a polypeptide of the invention, which is operably linked to one or more control sequences that direct the production of the polypeptide, and a method comprising cultivating a cell, which in its wild-type form produces the polypeptide, under conditions conducive for production of the polypeptide and optionally recovering the polypeptide. The invention also relates to a method of producing a polypeptide having DNase activity, comprising cultivating a recombinant host cell comprising a polynucleotide encoding the polypeptide under conditions conducive for production of the polypeptide.

Overview of Sequences

SEQ ID NO: 1 DNA encoding full length polypeptide from *Ascobolus stictoideus*
SEQ ID NO: 2 polypeptide derived from SEQ ID NO: 1
SEQ ID NO: 3 mature polypeptide obtained from *Ascobolus stictoideus*
SEQ ID NO: 4 DNA encoding full length polypeptide from *Umula sp-56769*
SEQ ID NO: 5 polypeptide derived from SEQ ID NO: 4
SEQ ID NO: 6 mature polypeptide obtained from *Umula sp-56769*
SEQ ID NO: 7 DNA encoding full length polypeptide from *Ascobolus* sp. ZY179
SEQ ID NO: 8 polypeptide derived from SEQ ID NO: 7
SEQ ID NO: 9 mature polypeptide obtained from *Ascobolus* sp. ZY179
SEQ ID NO: 10 DNA encoding full length polypeptide from *Morchella costata*
SEQ ID NO: 11 polypeptide derived from SEQ ID NO: 10
SEQ ID NO: 12 mature polypeptide obtained from *Morchella costata*
SEQ ID NO: 13 DNA encoding full length polypeptide from *Trichobolus zukalii*
SEQ ID NO: 14 polypeptide derived from SEQ ID NO: 13
SEQ ID NO: 15 mature polypeptide obtained from *Trichobolus zukalii*
SEQ ID NO: 16 DNA encoding full length polypeptide from *Trichophaea saccata*
SEQ ID NO: 17 polypeptide derived from SEQ ID NO: 16
SEQ ID NO: 18 mature polypeptide obtained from *Trichophaea saccata*
SEQ ID NO: 19 DNA encoding full length polypeptide from *Trichophaea minuta*
SEQ ID NO: 20 polypeptide derived from SEQ ID NO: 19
SEQ ID NO: 21 mature polypeptide obtained from *Trichophaea minuta*
SEQ ID NO: 22 DNA encoding full length polypeptide from *Trichophaea minuta*
SEQ ID NO: 23 polypeptide derived from SEQ ID NO: 22
SEQ ID NO: 24 mature polypeptide obtained from *Trichophaea minuta*
SEQ ID NO: 25 DNA encoding full length polypeptide from *Trichophaea abundans*
SEQ ID NO: 26 polypeptide derived from SEQ ID NO: 25
SEQ ID NO: 27 mature polypeptide obtained from *Trichophaea abundans*
SEQ ID NO: 28 DNA encoding full length polypeptide from *Pseudoplectania nigrella*
SEQ ID NO: 29 polypeptide derived from SEQ ID NO: 28
SEQ ID NO: 30 mature polypeptide obtained from *Pseudoplectania nigrella*
SEQ ID NO: 31 DNA encoding full length polypeptide from *Gyromitra esculenta*
SEQ ID NO: 32 polypeptide derived from SEQ ID NO: 31
SEQ ID NO: 33 mature polypeptide obtained from *Gyromitra esculenta*
SEQ ID NO: 34 DNA encoding full length polypeptide from *Morchella esculenta*
SEQ ID NO: 35 polypeptide derived from SEQ ID NO: 34
SEQ ID NO: 36 mature polypeptide obtained from *Morchella esculenta*
SEQ ID NO: 37 DNA encoding full length polypeptide from *Morchella crassipes*
SEQ ID NO: 38 polypeptide derived from SEQ ID NO: 37
SEQ ID NO: 39 mature polypeptide obtained from *Morchella crassipes*
SEQ ID NO: 40 DNA encoding full length polypeptide from *Disciotis venosa*
SEQ ID NO: 41 polypeptide derived from SEQ ID NO: 40
SEQ ID NO: 42 mature polypeptide obtained from *Disciotis venosa*
SEQ ID NOs: 43-48 are motifs disclosed herein.

Definitions

Figure 1:
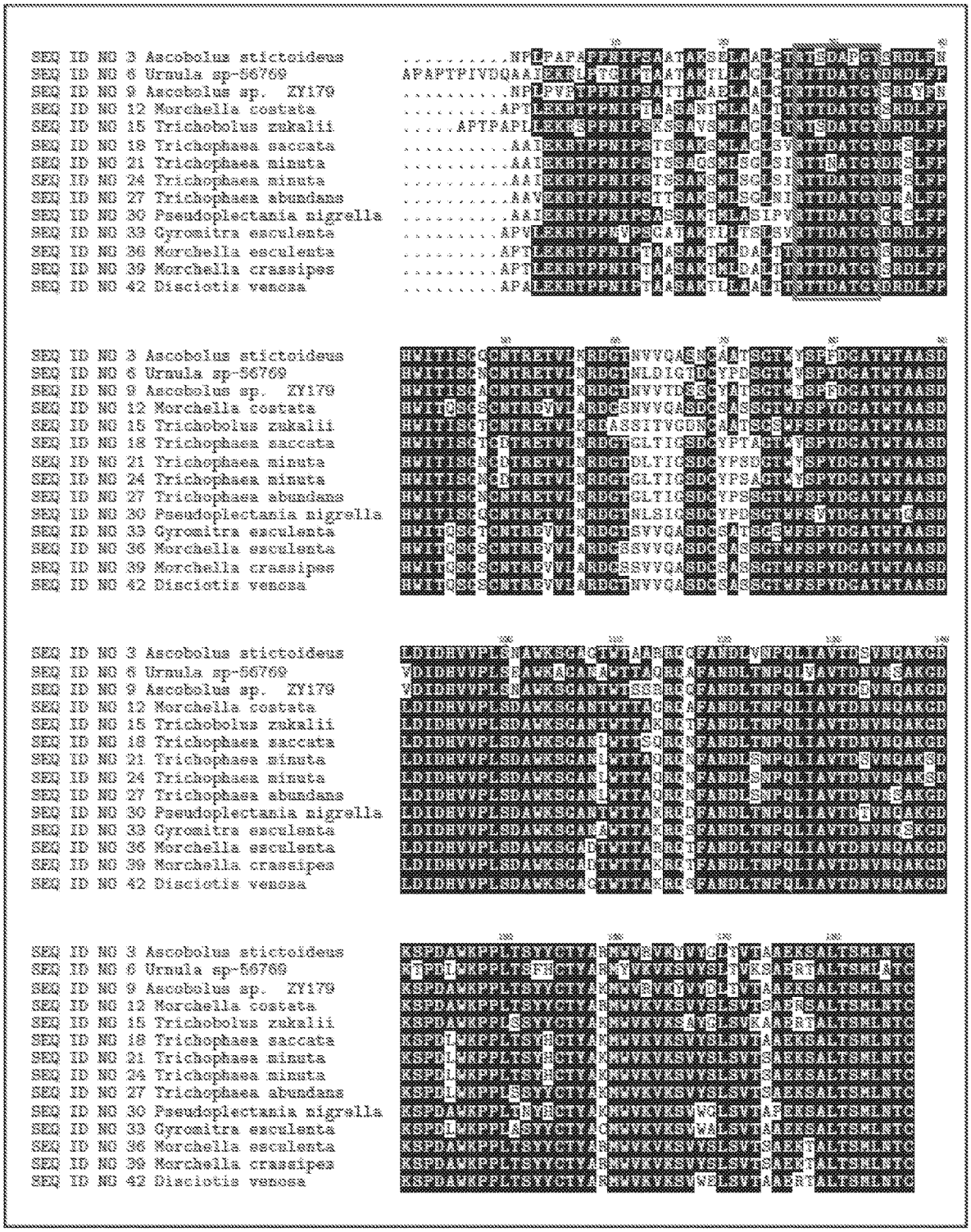
FIG. 1 shows an alignment of the polypeptides of the invention comprised in the clades.

The term "DNase" means a polypeptide with DNase activity that catalyzes the hydrolytic cleavage of phosphodiester linkages in the DNA backbone, thus degrading DNA. The term "DNases" and the expression "a polypeptide with DNase activity" are used interchangeably throughout the application. For purposes of the present invention, DNase activity is determined according to the procedure described in Assay I or Assay II. In one aspect, the polypeptide of the present invention have at least 20%, e.g., at least 40%, at least 50%, at least 60%, at least 70%, at least 80%, at least 90%, at least 95%, or at least 100% of the DNase activity of the mature polypeptide shown in SEQ ID NO: 3, 6, 9, 12, 15, 18, 21, 24, 27, 30, 33, 36, 39, or 42.

The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The term "biofilm" means organic matter produced by any group of microorganisms in which cells stick to each other or stick to a surface, such as a textile, dishware or hard surface or another kind of surface. These adherent cells are frequently embedded within a self-produced matrix of extracellular polymeric substance (EPS). Biofilm EPS is a polymeric conglomeration generally composed of extracellular DNA, proteins, and polysaccharides. Biofilms may form on living or non-living surfaces. The microbial cells growing in a biofilm are physiologically distinct from planktonic cells of the same organism, which, by contrast, are single-cells that may float or swim in a liquid medium. Bacteria living in a biofilm usually have significantly different properties from planktonic bacteria of the same species, as the dense and protected environment of the film allows them to cooperate and interact in various ways. One benefit of this environment for the microorganisms is increased resistance to detergents and antibiotics, as the dense extracellular matrix and the outer layer of cells protect the interior of the community. On laundry biofilm producing bacteria can be found among the following species including *Acinetobacter* sp., *Aeromicrobium* sp., *Brevundimonas* sp., *Microbacterium* sp., *Micrococcus luteus*, *Pseudomonas* sp., *Staphylococcus epidermidis*, and *Stenotrophomonas* sp. On hard surfaces biofilm producing bacteria can be found among the following species: *Acinetobacter* sp., *Aeromicrobium* sp., *Brevundimonas* sp., *Microbacterium* sp., *Micrococcus luteus*, *Pseudomonas* sp., *Staphylococcus epidermidis*, *Staphylococcus aureus* and *Stenotrophomonas* sp.

The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

The term "eDNA" means in the present context extracellular DNA.

The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

The term "deep cleaning" means disruption, reduction or removal of organic components such as polysaccharides, proteins, DNA, soil or other components present in organic matter such as biofilm.

The term "detergent adjunct ingredient" is different to the DNases of this invention. The precise nature of these additional adjunct components, and levels of incorporation thereof, will depend on the physical form of the composition and the nature of the operation for which it is to be used. Suitable adjunct materials include, but are not limited to the components described below such as surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric agents, clay soil removal/anti-redeposition agents, brighteners, suds suppressors, dyes, perfumes, structure elasticizing agents, fabric softeners, carriers, hydrotropes, builders and co-builders, fabric huing agents, anti-foaming agents, dispersants, processing aids, and/or pigments.

The term "detergent composition" refers to compositions that find use in the removal of undesired compounds from items to be cleaned, such as textiles. The terms "detergent compositions" and "cleaning compositions" are used interchangeably in the present application. The detergent composition may be used to e.g. clean textiles for both household cleaning and industrial cleaning. The terms encompass any materials/compounds selected for the particular type of cleaning composition desired and the form of the product (e.g., liquid, gel, powder, granulate, paste, or spray compositions) and includes, but is not limited to, detergent compositions (e.g., liquid and/or solid laundry detergents and fine fabric detergents; fabric fresheners; fabric softeners; and textile and laundry pre-spotters/pretreatment). In addition to containing the enzyme of the invention, the detergent formulation may contain one or more additional enzymes (such as proteases, amylases, lipases, cutinases, cellulases, endoglucanases, xyloglucanases, pectinases, pectin lyases, xanthanases, peroxidases, haloperoxygenases, catalases and mannanases, or any mixture thereof), and/or detergent adjunct ingredients such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

The term "expression" includes any step involved in the production of a polypeptide including, but not limited to, transcription, post-transcriptional modification, translation, post-translational modification, and secretion.

The term "expression vector" means a linear or circular DNA molecule that comprises a polynucleotide encoding a polypeptide and is operably linked to control sequences that provide for its expression. A control sequence may be foreign or heterologous to the expression vector.

A "His-tag" refers to a polyhistidine tag typically comprising at least 6 histidine residues, that may be added to the N- or C-terminal. His-tags are known in the art for use in e.g. protein purification, but may also be used for improving solubility at low pH values. Similarly, an "HQ-tag", i.e. a histidine-glutamine tag, may also be used for the purpose of purification as is known in the art.

The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance). An isolated substance may be present in a fermentation broth sample; e.g. a host cell may be genetically modified to express the polypeptide of the invention. The fermentation broth from that host cell will comprise the isolated polypeptide.

The term "laundering" relates to both household laundering and industrial laundering and means the process of treating textiles with a solution containing a cleaning or detergent composition of the present invention. The laundering process can for example be carried out using e.g. a household or an industrial washing machine or can be carried out by hand.

By the term "malodor" is meant an odor which is not desired on clean items. The cleaned item should smell fresh and clean without malodors adhered to the item. One example of malodor is compounds with an unpleasant smell, which may be produced by microorganisms and trapped within a biofilm or stick to the "glue" of a biofilm. Other examples of unpleasant smells are sweat or body odor adhered to an item, which has been in contact with human or animal. Other examples of malodor are odor from spices, which sticks to items for example curry or other exotic spices which smells strongly.

The term "mature polypeptide" means a polypeptide in its final form following translation and any post-translational modifications, such as N-terminal processing, C-terminal truncation, glycosylation, phosphorylation, etc.

In one aspect, the mature polypeptide is amino acids 1 to 187 of SEQ ID NO: 2. Amino acids −18 to −1 of SEQ ID NO: 2 is the signal peptide.

In one aspect, the mature polypeptide is amino acids 1 to 197 of SEQ ID NO: 5. Amino acids −16 to −1 of SEQ ID NO: 5 is the signal peptide.

In one aspect, the mature polypeptide is amino acids 1 to 187 of SEQ ID NO: 8. Amino acids −18 to −1 of SEQ ID NO: 8 is the signal peptide.

In one aspect, the mature polypeptide is amino acids 1 to 188 of SEQ ID NO: 11. Amino acids −15 to −1 of SEQ ID NO: 11 is the signal peptide.

In one aspect, the mature polypeptide is amino acids 1 to 192 of SEQ ID NO: 14. Amino acids −19 to −1 of SEQ ID NO: 14 is the signal peptide.

In one aspect, the mature polypeptide is amino acids 1 to 187 of SEQ ID NO: 17. Amino acids −17 to −1 of SEQ ID NO: 17 is the signal peptide.

In one aspect, the mature polypeptide is amino acids 1 to 187 of SEQ ID NO: 20. Amino acids −17 to −1 of SEQ ID NO: 20 is the signal peptide.

In one aspect, the mature polypeptide is amino acids 1 to 187 of SEQ ID NO: 23. Amino acids −17 to −1 of SEQ ID NO: 23 is the signal peptide.

In one aspect, the mature polypeptide is amino acids 1 to 187 of SEQ ID NO: 26. Amino acids −17 to −1 of SEQ ID NO: 26 is the signal peptide.

In one aspect, the mature polypeptide is amino acids 1 to 187 of SEQ ID NO: 29. Amino acids −18 to −1 of SEQ ID NO: 29 is the signal peptide.

In one aspect, the mature polypeptide is amino acids 1 to 188 of SEQ ID NO: 32. Amino acids −15 to −1 of SEQ ID NO: 32 is the signal peptide.

In one aspect, the mature polypeptide is amino acids 1 to 188 of SEQ ID NO: 35. Amino acids −15 to −1 of SEQ ID NO: 35 is the signal peptide.

In one aspect, the mature polypeptide is amino acids 1 to 188 of SEQ ID NO: 38. Amino acids −15 to −1 of SEQ ID NO: 38 is the signal peptide.

In one aspect, the mature polypeptide is amino acids 1 to 188 of SEQ ID NO: 41. Amino acids −15 to −1 of SEQ ID NO: 41 is the signal peptide.

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

The term "mature polypeptide coding sequence" means a polynucleotide that encodes a mature polypeptide having DNase activity.

In one aspect, the mature polypeptide coding sequence is nucleotides 55 to 748 of SEQ ID NO: 1 and nucleotides 1 to 54 of SEQ ID NO: 1 encode a signal peptide.

In one aspect, the mature polypeptide coding sequence is nucleotides 49 to 970 of SEQ ID NO: 4 and nucleotides 1 to 48 of SEQ ID NO: 4 encode a signal peptide.

In one aspect, the mature polypeptide coding sequence is nucleotides 55 to 725 of SEQ ID NO: 7 and nucleotides 1 to 54 of SEQ ID NO: 7 encode a signal peptide.

In one aspect, the mature polypeptide coding sequence is nucleotides 46 to 904 of SEQ ID NO: 10 and nucleotides 1 to 45 of SEQ ID NO: 10 encode a signal peptide.

In one aspect, the mature polypeptide coding sequence is nucleotides 58 to 819 of SEQ ID NO: 13 and nucleotides 1 to 57 of SEQ ID NO: 13 encode a signal peptide.

In one aspect, the mature polypeptide coding sequence is nucleotides 52 to 784 of SEQ ID NO: 16 and nucleotides 1 to 51 of SEQ ID NO: 16 encode a signal peptide.

In one aspect, the mature polypeptide coding sequence is nucleotides 52 to 781 of SEQ ID NO: 19 and nucleotides 1 to 51 of SEQ ID NO: 19 encode a signal peptide.

In one aspect, the mature polypeptide coding sequence is nucleotides 52 to 784 of SEQ ID NO: 22 and nucleotides 1 to 51 of SEQ ID NO: 22 encode a signal peptide.

In one aspect, the mature polypeptide coding sequence is nucleotides 52 to 790 of SEQ ID NO: 25 and nucleotides 1 to 51 of SEQ ID NO: 25 encode a signal peptide.

In one aspect, the mature polypeptide coding sequence is nucleotides 55 to 615 of SEQ ID NO: 28 and nucleotides 1 to 54 of SEQ ID NO: 28 encode a signal peptide.

In one aspect, the mature polypeptide coding sequence is nucleotides 46 to 954 of SEQ ID NO: 31 and nucleotides 1 to 45 of SEQ ID NO: 31 encode a signal peptide.

In one aspect, the mature polypeptide coding sequence is nucleotides 46 to 901 of SEQ ID NO: 34 and nucleotides 1 to 45 of SEQ ID NO: 34 encode a signal peptide.

In one aspect, the mature polypeptide coding sequence is nucleotides 46 to 902 of SEQ ID NO: 37 and nucleotides 1 to 45 of SEQ ID NO: 37 encode a signal peptide.

In one aspect, the mature polypeptide coding sequence is nucleotides 46 to 838 of SEQ ID NO: 40 and nucleotides 1 to 45 of SEQ ID NO: 40 encode a signal peptide.

The term "nucleic acid construct" means a nucleic acid molecule, either single- or double-stranded, which is isolated from a naturally occurring gene or is modified to contain segments of nucleic acids in a manner that would not otherwise exist in nature or which is synthetic, and which comprises one or more control sequences that may be heterologous.

The term "operably linked" means a configuration in which a control sequence is placed at an appropriate position relative to the coding sequence of a polynucleotide such that the control sequence directs expression of the coding sequence.

The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–
Total Number of Gaps in Alignment)

The term "variant" means a polypeptide having DNase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position Nomenclature For purposes of the present invention, the nomenclature [E/Q] means that the amino acid at this position may be a glutamic acid (Glu, E) or a glutamine (Gln, Q). Likewise, the nomenclature [V/G/A/I] means that the amino acid at this position may be a valine (Val, V), glycine (Gly, G), alanine (Ala, A) or isoleucine (Ile, I), and so forth for other combinations as described herein. Unless otherwise limited further, the amino acid X is defined such that it may be any of the 20 natural amino acids.

DETAILED DESCRIPTION OF THE
INVENTION

The present invention relates to novel polypeptides having deoxyribonuclease (DNase) activity which can be used for preventing, reducing or removing biofilm soiling on items such as textiles and/or fabric. A polypeptide having DNase activity or a deoxyribonuclease (DNase) is any enzyme that catalyzes the hydrolytic cleavage of phosphodiester linkages in the DNA backbone, thus degrading DNA. The two terms polypeptide having DNase activity and DNase are used interchangeably.

Polypeptides Having DNase Activity

The present invention relates to polypeptides having DNase activity i.e. DNases. Examples of polypeptides having DNase activity are polypeptides comprising the PFAM domain DUF1524 (pfam.xfam.org/), "The Pfam protein families database: towards a more sustainable future", R. D. Finn, et. al. Nucleic Acids Research (2016) Database Issue 44: D279-D285". The DUF1524 domain contains a conserved HXXP sequence motif commonly found in nucleases (M. A. Machnicka, et. al. Phylogenomics and sequence-structure-function relationships in the GmrSD family of Type IV restriction enzymes, BMC Bioinformatics, 2015, 16, 336). DUF means domain of unknown function, and the polypeptide families comprising, e.g., DUF have been collected together in the Pfam database. The Pfam data base provides sequence alignments and hidden Markov models that define the collected protein domains. A protein domain is a conserved part of a given protein sequence. Each domain forms a compact three-dimensional structure and often can be independently stable and folded. Many proteins consist of several structural domains. One domain may appear in a variety of different proteins.

One particular DUF may be identified using the prefix DUF followed by a number, e.g., 1524. The DUF1524 is a family of proteins all comprising the HXXP motif, where H is the amino acid histidine, P is the amino acid proline and X is any amino acid. In one embodiment of the invention the polypeptides having DNase activity comprise the DUF1524 domain. Thus, according to one embodiment the invention relates to polypeptides having DNase activity, wherein the polypeptides comprise the DUF1524 domain. The invention also relates to the use of such DNases e.g. for cleaning of textiles and/or fabric. The invention further relates to compositions comprising polypeptides having DNase activity, and which comprise a DUF1524 domain e.g. HXXP. Such compositions may be but are not limited to liquid or powder laundry compositions, tablets, unit dose, spray or soap bars. Polypeptides comprising the DUF1524 domain comprises several motifs, of which one example is [E/D/H]H[I/V/L/F/M]X[P/A/S] (SEQ ID NO: 43), situated in positions corresponding to positions 95 to 99 in the predicted mature DNase polypeptide from M. *costata* (SEQ ID NO: 12). H96 is a catalytic residue involved in the catalytic activity of DUF1524, and part of the HXXP motif. Another motif which may be comprised by the polypeptides of the invention is [T/D/S][G/N]PQL (SEQ ID NO: 44), corresponding to position 124 to 128 in SEQ ID NO: 12, where Q is involved in stabilizing the HXXP motif.

As already described the polypeptides of the invention having DNase activity may comprise the structural domains of DUF1524. A further domain, preferably shared by the DNases of the invention, was identified. This domain is termed NUC1 and polypeptides of this domain are in addition to having DNase activity, characterized by comprising certain motifs e.g. one or more of the motifs; [F/L/Y/I]A[N/R]D[L/I/P/V] (SEQ ID NO: 45), corresponding to position 119 to 123 in SEQ ID NO: 12 or C[D/N]T[A/R] (SEQ ID NO: 46), corresponding to position 50 to 53 in SEQ ID NO: 12. From the NUC1 domain a sub-domain has been identified and this domain is termed the NUC1_A domain. In addition to comprising any of the domains above the polypeptides having DNase activity belonging to the NUC1_A domain may share the common motif [D/Q][I/V]DH (SEQ ID NO: 47), corresponding to amino acid 93 to 96 in the reference polypeptide (SEQ ID NO: 12). The D at the position corresponding to position 93 of SEQ ID NO: 12 is predicted to be involved in binding of catalytic metal ion cofactor. In one embodiment the invention relates to polypeptides comprising the motif [D/Q][I/V]DH (SEQ ID NO: 47), wherein the polypeptides have DNase activity. In some embodiments of the invention the DNases of the invention belongs to a specific subgroup or clade comprising the motif RT[TS][DN][AP][TDPS]GY (SEQ ID NO: 48) corresponding to positions 28 to 35 of SEQ ID NO: 12 where D correspond to position 31 of SEQ ID NO: 12. In one aspect, the polypeptide of the invention having DNase activity belongs to the RTTDA clade and comprises the motif RT[TS][DN][AP][TDPS]GY (SEQ ID NO: 48). In one aspect, the polypeptide of the invention having DNase activity belongs to the RTTDA clade and comprises the motif RT[TS][DN][AP][TDPS]GY (SEQ ID NO: 48), wherein the DNase is derived from fungi e.g. is of fungal origin.

Figure 2:
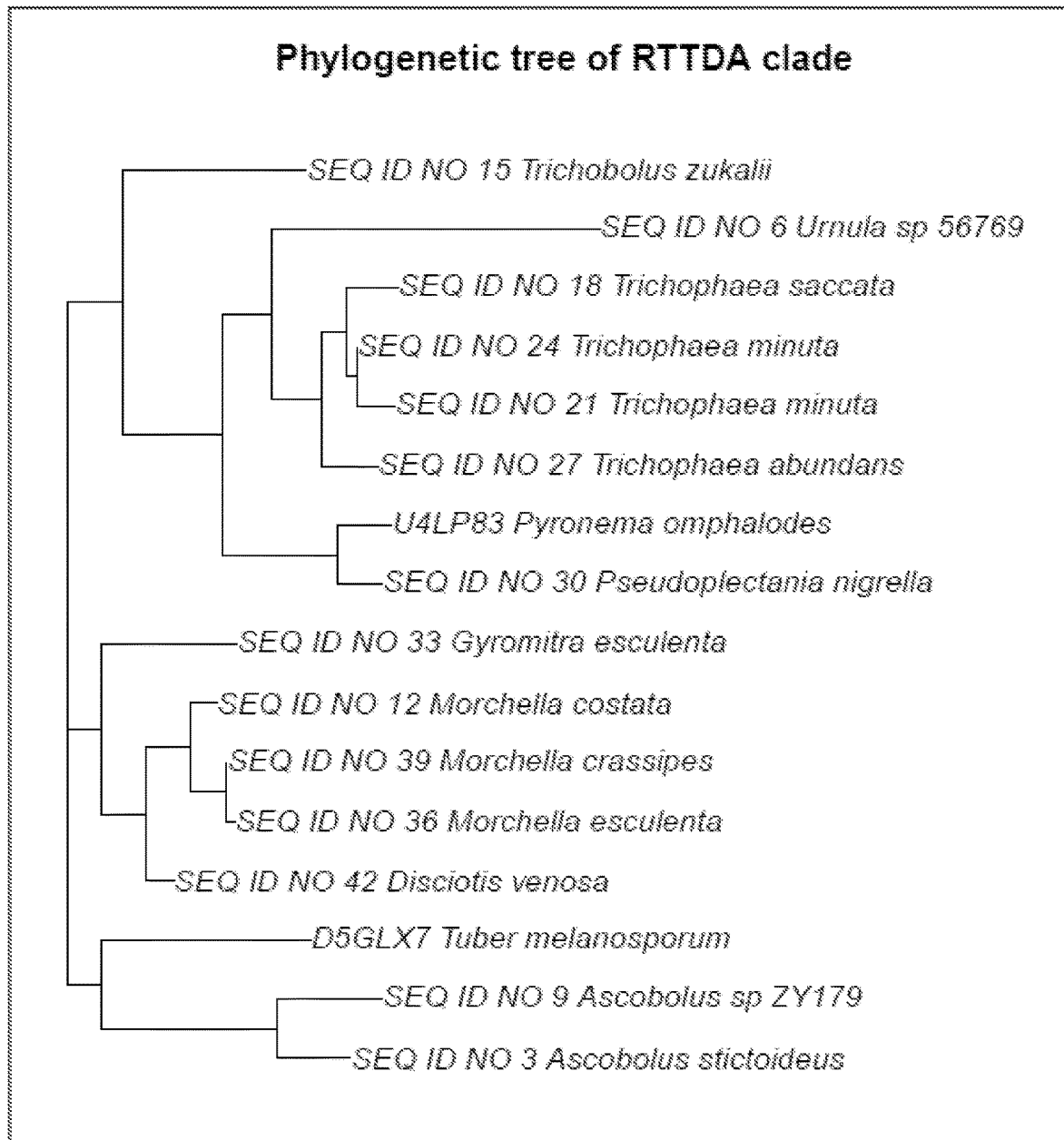
FIG. 2 shows a phyiogenetic tree of the RTTDA clade.

An alignment of the polypeptides of the invention comprised in the clades is shown in FIG. 1. A phylogenetic tree of the RTTDA clade is shown in FIG. 2. The RTTDA clade is defined in the present context as a subgroup of NUC1_A DNases which share the motif RT[TS][DN][AP][TDPS]GY (SEQ ID NO: 48) and is structurally and optionally also functionally more related than other NUC1_A DNases i.e. it is a subgroup of closely related DNases. In one aspect, the invention relates to a polypeptide having DNase activity, wherein the polypeptide belongs to the RTTDA clade and comprises the motif RT[TS][DN][AP][TDPS]GY (SEQ ID NO: 48), wherein the DNase is a fungal DNase i.e. of fungal origin. In one aspect, the invention relates to a polypeptide having DNase activity, wherein the polypeptide belongs to the RTTDA clade and comprises the motif RT[TS][DN][AP][TDPS]GY (SEQ ID NO: 48), wherein the polypeptide is selected from the group consisting of the polypeptides shown in SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42 and polypeptides having at least 80% sequence identity hereto.

In one aspect of the invention the DNases is a polypeptide comprising one of more of the motifs selected from the group consisting of [E/D/H]H[I/V/L/F/M]X[P/A/S] (SEQ ID NO: 43), [T/D/S][G/N]PQL (SEQ ID NO: 44), [F/L/Y/I]A[N/R]D[L/I/P/V] (SEQ ID NO: 45), C[D/N]T[A/R] (SEQ ID NO: 46), [D/Q][I/V]DH (SEQ ID NO: 47), and RT[TS][DN][AP][TDPS]GY (SEQ ID NO: 48). Preferably, the DNases of the invention comprise the motif RT[TS][DN][AP][TDPS]GY (SEQ ID NO: 48). One embodiment of the invention relates to a polypeptide having DNase activity, wherein the polypeptide comprises any of the motifs [E/D/H]H[I/V/L/F/M]X[P/A/S] (SEQ ID NO: 43), [T/D/S][G/N]PQL (SEQ ID NO: 44), [F/L/Y/I]A[N/R]D[L/I/P/V] (SEQ ID NO: 45), C[D/N]T[A/R] (SEQ ID NO: 46), [D/Q][I/V]DH (SEQ ID NO: 47), and RT[TS][DN][AP][TDPS]GY (SEQ ID NO: 48) and wherein the polypeptide is selected from the group consisting of;
  i) a polypeptide comprises or consisting of SEQ ID NO: 3 or a polypeptide having at least 80% sequence identity hereto;
  ii) a polypeptide comprises or consisting of SEQ ID NO: 6 or a polypeptide having at least 80% sequence identity hereto;
  iii) a polypeptide comprises or consisting of SEQ ID NO: 9 or a polypeptide having at least 80% sequence identity hereto;
  iv) a polypeptide comprises or consisting of SEQ ID NO: 12 or a polypeptide having at least 80% sequence identity hereto;
  v) a polypeptide comprises or consisting of SEQ ID NO: 15 or a polypeptide having at least 80% sequence identity hereto;
  vi) a polypeptide comprises or consisting of SEQ ID NO: 18 or a polypeptide having at least 80% sequence identity hereto;
  vii) a polypeptide comprises or consisting of SEQ ID NO: 21 or a polypeptide having at least 80% sequence identity hereto;
  viii) a polypeptide comprises or consisting of SEQ ID NO: 24 or a polypeptide having at least 80% sequence identity hereto;
  ix) a polypeptide comprises or consisting of SEQ ID NO: 27 or a polypeptide having at least 80% sequence identity hereto;
  x) a polypeptide comprises or consisting of SEQ ID NO: 30 or a polypeptide having at least 80% sequence identity hereto;
  xi) a polypeptide comprises or consisting of SEQ ID NO: 33 or a polypeptide having at least 80% sequence identity hereto;
  xii) a polypeptide comprises or consisting of SEQ ID NO: 36 or a polypeptide having at least 80% sequence identity hereto;
  xiii) a polypeptide comprises or consisting of SEQ ID NO: 39 or a polypeptide having at least 80% sequence identity hereto; and
  xiv) a polypeptide comprises or consisting of SEQ ID NO: 42 or a polypeptide having at least 80% sequence identity hereto.

In one embodiment, the DNase polypeptide comprises the motif RT[TS][DN][AP][TDPS]GY (SEQ ID NO: 48), and preferably is selected from the group selected from polypeptides comprising the amino acid sequences shown in SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO:27, SEQ ID NO: 30, SEQ ID NO: 33, SEQ ID NO: 36, SEQ ID NO: 39 and SEQ ID NO: 42 or polypeptides having at least 80% sequence identity hereto. In one embodiment, the DNase polypeptide is obtained or is obtainable from the taxonomic order Pezizales and is preferably is selected from the group selected from SEQ ID NO: 3, SEQ ID NO: 6, SEQ ID NO: 9, SEQ ID NO: 12, SEQ ID NO: 18, SEQ ID NO: 21, SEQ ID NO: 24, SEQ ID NO:27, SEQ ID NO: 30, SEQ ID NO: 33, SEQ ID NO: 36, SEQ ID NO: 39 and SEQ ID NO: 42 or polypeptides having at least 80% sequence identity hereto.

In one embodiment, the DNase polypeptide is obtained or is obtainable from the taxonomic order Pezizales. In one embodiment, the DNase polypeptide is obtained or is obtainable from the taxonomic family Pezizales and is selected from the group selected from SEQ ID NO: 3, SEQ ID NO: 6, SEQ ID NO: 9, SEQ ID NO: 12, SEQ ID NO: 18, SEQ ID NO: 21, SEQ ID NO: 24, SEQ ID NO:27, SEQ ID NO: 30, SEQ ID NO: 33, SEQ ID NO: 36, SEQ ID NO: 39 and SEQ ID NO: 42 or a polypeptide having at least 80% sequence identity hereto. The motifs and domains are defined cross-kingdom meaning that the domains and motifs comprise both fungal and bacterial DNases. It is well known that DNases deriving from organisms belonging to different taxonomic groups may nevertheless share common structural elements, which can be identified by comparing the primary structures e.g. amino acid sequences and grouping the DNases according to sequence homology. However, common structural elements may also be identified by comparing the three-dimensional (3D) structure of various DNases. Both approaches have been applied in the present invention.

The structural approach identified DNases, which derive from organisms from divergent taxonomic groups but share structural elements common for the identified group. Structural domains and sub-domains are groups of DNases from divergent taxa that share structural elements. A clade is a grouping that includes a common ancestor and all the descendants (living and extinct) of that ancestor (evolution-.berkeley.edu/evolibrary/article/0_0_0/evo_06). A clade has a shared phylogeny. In the examples is described building of phylogenetic trees, such trees have branches which represent clades, see FIGS. 1 and 2.

One embodiment of the invention relates a polypeptide of the RTTDA clade, wherein the polypeptide has DNase activity, and wherein the polypeptide is selected from the group consisting of:

(a) a polypeptide having at least 80% sequence identity to the polypeptide of SEQ ID NO: 3;
(b) a polypeptide having at least 80% sequence identity to the polypeptide of SEQ ID NO: 6;
(c) a polypeptide having at least 80% sequence identity to the polypeptide of SEQ ID NO: 9;
(d) a polypeptide having at least 80% sequence identity to the polypeptide of SEQ ID NO: 12;
(e) a polypeptide having at least 80% sequence identity to the polypeptide of SEQ ID NO: 15;
(f) a polypeptide having at least 80% sequence identity to the polypeptide of SEQ ID NO: 18;
(g) a polypeptide having at least 80% sequence identity to the polypeptide of SEQ ID NO: 21;
(h) a polypeptide having at least 80% sequence identity to the polypeptide of SEQ ID NO: 24;
(i) a polypeptide having at least 80% sequence identity to the polypeptide of SEQ ID NO: 27;
(j) a polypeptide having at least 80% sequence identity to the polypeptide of SEQ ID NO: 30;
(k) a polypeptide having at least 80% sequence identity to the polypeptide of SEQ ID NO: 33;
(l) a polypeptide having at least 80% sequence identity to the polypeptide of SEQ ID NO: 36;
(m) a polypeptide having at least 80% sequence identity to the polypeptide of SEQ ID NO: 39;
(n) a polypeptide having at least 80% sequence identity to the polypeptide of SEQ ID NO: 42;
(o) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39 and SEQ ID NO: 42, wherein the variant has DNase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions;
(p) a polypeptide comprising the polypeptide of (a) to (o) and a N-terminal and/or C-terminal His-tag and/or HQ-tag;
(q) a polypeptide comprising the polypeptide of (a) to (o) and a N-terminal and/or C-terminal extension of between 1 and 10 amino acids;
(r) a fragment of the polypeptide of (a) to (o) having DNase activity and having at least 90% of the length of the mature polypeptide; and
(s) a polypeptide comprising the motif RT[TS][DN][AP][TDPS]GY (SEQ ID NO: 48).

The DNases of the present invention are useful in cleaning compositions and are effective in deep cleaning of surfaces such as fabrics. The DNases of the present invention are effective in reducing or removing DNA soiling from e.g. organic matter. One example of organic matter is biofilm which is an extracellular matrix produced by various microorganisms. The extracellular polymeric matrix is composed of polysaccharides, extracellular DNA and proteins. Organic matter like biofilm may be sticky or glueing, which when present on textile, may give rise to redeposition or back-staining of soil resulting in a greying of the textile. Another drawback of organic matter e.g. biofilm is the malodor as various malodor related molecules are often associated with organic matter e.g. biofilm.

One aspect of the invention relates to a method for laundering an item comprising the steps of:

a. Exposing an item to a wash liquor comprising a polypeptide or a cleaning composition comprising a polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39 and SEQ ID NO: 42 or polypeptides having at least 80% sequence identity hereto, wherein the polypeptide has DNase activity;
b. Completing at least one wash cycle; and
c. Optionally rinsing the item,
wherein the item is a textile.

The DNases of the invention are therefore useful for prevention, reduction or removal of malodor and for prevention, reduction of redeposition and improving whiteness.

One embodiment of the invention relates to the use of polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39 and SEQ ID NO: 42 or polypeptides having at least 80% sequence identity hereto for deep cleaning of an item, wherein the item is a textile. One embodiment of the invention relates to the use of polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39 and SEQ ID NO: 42 or polypeptides having at least 80% sequence identity hereto;

(i) for preventing, reducing or removing stickiness of the item;
(ii) for pretreating stains on the item;
(iii) for preventing, reducing or removing redeposition of soil during a wash cycle;
(iv) for preventing, reducing or removing adherence of soil to the item;
(v) for maintaining or improving whiteness of the item;
(vi) for preventing, reducing or removal malodor from the item,
wherein the item is a textile.

The textile may e.g. be cotton or polyester or a mixture hereof.

One embodiment of the invention relates to a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39 or SEQ ID NO: 42.

In one embodiment, the present invention relates to polypeptides having a sequence identity to the mature polypeptide of SEQ ID NO: 2 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the DNase activity of the mature polypeptide of SEQ ID NO: 2, e.g. at least 80% or at least 90% of the DNase activity of the mature polypeptide of SEQ ID NO: 2.

In a particular embodiment the invention relates to polypeptides having a sequence identity to the mature polypeptide of SEQ ID NO: 5 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the DNase activity of the mature polypeptide of SEQ ID NO: 5, e.g. at least 80% or at least 90% of the DNase activity of the mature polypeptide of SEQ ID NO: 5.

In a particular embodiment the invention relates to polypeptides having a sequence identity to the mature polypeptide of SEQ ID NO: 8 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the DNase activity of the mature polypeptide of SEQ ID NO: 8, e.g. at least 80% or at least 90% of the DNase activity of the mature polypeptide of SEQ ID NO: 8.

In a particular embodiment the invention relates to polypeptides having a sequence identity to the mature polypeptide of SEQ ID NO: 11 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the DNase activity of the mature polypeptide of SEQ ID NO: 11, e.g. at least 80% or at least 90% of the DNase activity of the mature polypeptide of SEQ ID NO: 11.

In a particular embodiment the invention relates to polypeptides having a sequence identity to the mature polypeptide of SEQ ID NO: 14 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the DNase activity of the mature polypeptide of SEQ ID NO: 14, e.g. at least 80% or at least 90% of the DNase activity of the mature polypeptide of SEQ ID NO: 14.

In a particular embodiment the invention relates to polypeptides having a sequence identity to the mature polypeptide of SEQ ID NO: 17 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the DNase activity of the mature polypeptide of SEQ ID NO: 17, e.g. at least 80% or at least 90% of the DNase activity of the mature polypeptide of SEQ ID NO: 17.

In a particular embodiment the invention relates to polypeptides having a sequence identity to the mature polypeptide of SEQ ID NO: 20 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the DNase activity of the mature polypeptide of SEQ ID NO: 20, e.g. at least 80% or at least 90% of the DNase activity of the mature polypeptide of SEQ ID NO: 20.

In a particular embodiment the invention relates to polypeptides having a sequence identity to the mature polypeptide of SEQ ID NO: 23 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the DNase activity of the mature polypeptide of SEQ ID NO: 23, e.g. at least 80% or at least 90% of the DNase activity of the mature polypeptide of SEQ ID NO: 23.

In a particular embodiment the invention relates to polypeptides having a sequence identity to the mature polypeptide of SEQ ID NO: 26 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the DNase activity of the mature polypeptide of SEQ ID NO: 26, e.g. at least 80% or at least 90% of the DNase activity of the mature polypeptide of SEQ ID NO: 26.

In a particular embodiment the invention relates to polypeptides having a sequence identity to the mature polypeptide of SEQ ID NO: 29 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the DNase activity of the mature polypeptide of SEQ ID NO: 29, e.g. at least 80% or at least 90% of the DNase activity of the mature polypeptide of SEQ ID NO: 29.

In a particular embodiment the invention relates to polypeptides having a sequence identity to the mature polypeptide of SEQ ID NO: 32 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the DNase activity of the mature polypeptide of SEQ ID NO: 32, e.g. at least 80% or at least 90% of the DNase activity of the mature polypeptide of SEQ ID NO: 32.

In a particular embodiment the invention relates to polypeptides having a sequence identity to the mature polypeptide of SEQ ID NO: 35 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the DNase activity of the mature polypeptide of SEQ ID NO: 35, e.g. at least 80% or at least 90% of the DNase activity of the mature polypeptide of SEQ ID NO: 35.

In a particular embodiment the invention relates to polypeptides having a sequence identity to the mature polypeptide of SEQ ID NO: 38 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the DNase activity of the mature polypeptide of SEQ ID NO: 38, e.g. at least 80% or at least 90% of the DNase activity of the mature polypeptide of SEQ ID NO: 38.

In a particular embodiment the invention relates to polypeptides having a sequence identity to the mature polypeptide of SEQ ID NO: 41 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the DNase activity of the mature polypeptide of SEQ ID NO: 41, e.g. at least 80% or at least 90% of the DNase activity of the mature polypeptide of SEQ ID NO: 41.

One embodiment of the invention relates to a polypeptide selected from the group consisting of polypeptides:
(a) comprising or consisting of SEQ ID NO: 3 or the mature polypeptide of SEQ ID NO: 2;
(b) comprising or consisting of SEQ ID NO: 6 or the mature polypeptide of SEQ ID NO: 5;
(c) comprising or consisting of SEQ ID NO: 9 or the mature polypeptide of SEQ ID NO: 8;
(d) comprising or consisting of SEQ ID NO: 12 or the mature polypeptide of SEQ ID NO: 11;
(e) comprising or consisting of SEQ ID NO: 15 or the mature polypeptide of SEQ ID NO: 14;
(f) comprising or consisting of SEQ ID NO: 18 or the mature polypeptide of SEQ ID NO: 17;
(g) comprising or consisting of SEQ ID NO: 21 or the mature polypeptide of SEQ ID NO: 20;
(h) comprising or consisting of SEQ ID NO: 24 or the mature polypeptide of SEQ ID NO: 23;
(i) comprising or consisting of SEQ ID NO: 27 or the mature polypeptide of SEQ ID NO: 26;
(j) comprising or consisting of SEQ ID NO: 30 or the mature polypeptide of SEQ ID NO: 29;
(k) comprising or consisting of SEQ ID NO: 33 or the mature polypeptide of SEQ ID NO: 32;
(l) comprising or consisting of SEQ ID NO: 36 or the mature polypeptide of SEQ ID NO: 35;
(m) comprising or consisting of SEQ ID NO: 39 or the mature polypeptide of SEQ ID NO: 38; and
(n) comprising or consisting of SEQ ID NO: 42 or the mature polypeptide of SEQ ID NO: 41;

In some embodiments, the polypeptide has been isolated. A polypeptide of the present invention preferably comprises or consists of the amino acid sequence shown in SEQ ID NO: 3 or an allelic variant thereof; or is a fragment thereof having DNase activity. In another aspect, the polypeptide comprises or consists of the mature polypeptide of SEQ ID NO: 2. In another aspect, the polypeptide comprises or consists of amino acids 1 to 187 of SEQ ID NO: 2.

In one embodiment, the polypeptide preferably comprises or consists of the amino acid sequence shown in SEQ ID NO: 3; comprises the amino acid sequence shown in SEQ ID NO: 3 and a N-terminal and/or C-terminal His-tag and/or HQ-tag; comprises the amino acid sequence of SEQ ID NO: 3 and a N-terminal and/or C-terminal extension of between 1 and 10 amino acids;

or is a fragment thereof having DNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 3.

In some embodiments, the polypeptide has been isolated. A polypeptide of the present invention preferably comprises or consists of the amino acid sequence shown in SEQ ID NO: 6 or an allelic variant thereof; or is a fragment thereof having DNase activity. In another aspect, the polypeptide comprises or consists of the mature polypeptide of SEQ ID NO: 5. In another aspect, the polypeptide comprises or consists of amino acids 1 to 197 of SEQ ID NO: 5.

In one embodiment, the polypeptide preferably comprises or consists of the amino acid sequence shown in SEQ ID NO: 6; comprises the amino acid sequence shown in SEQ ID NO: 6 and a N-terminal and/or C-terminal His-tag and/or HQ-tag; comprises the amino acid sequence of SEQ ID NO: 6 and a N-terminal and/or C-terminal extension of between 1 and 10 amino acids; or is a fragment thereof having DNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 6.

In some embodiments, the polypeptide has been isolated. A polypeptide of the present invention preferably comprises or consists of the amino acid sequence shown in SEQ ID NO: 9 or an allelic variant thereof; or is a fragment thereof having DNase activity. In another aspect, the polypeptide comprises or consists of the mature polypeptide of SEQ ID NO: 8. In another aspect, the polypeptide comprises or consists of amino acids 1 to 187 of SEQ ID NO: 8.

In one embodiment, the polypeptide preferably comprises or consists of the amino acid sequence shown in SEQ ID NO: 9; comprises the amino acid sequence shown in SEQ ID NO: 9 and a N-terminal and/or C-terminal His-tag and/or HQ-tag; comprises the amino acid sequence of SEQ ID NO: 9 and a N-terminal and/or C-terminal extension of between 1 and 10 amino acids; or is a fragment thereof having DNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 9.

In some embodiments, the polypeptide has been isolated. A polypeptide of the present invention preferably comprises or consists of the amino acid sequence shown in SEQ ID NO: 12 or an allelic variant thereof; or is a fragment thereof having DNase activity. In another aspect, the polypeptide comprises or consists of the mature polypeptide of SEQ ID NO: 11. In another aspect, the polypeptide comprises or consists of amino acids 1 to 188 of SEQ ID NO: 11.

In one embodiment, the polypeptide preferably comprises or consists of the amino acid sequence shown in SEQ ID NO: 12; comprises the amino acid sequence shown in SEQ ID NO: 12 and a N-terminal and/or C-terminal His-tag and/or HQ-tag; comprises the amino acid sequence of SEQ ID NO: 12 and a N-terminal and/or C-terminal extension of between 1 and 10 amino acids; or is a fragment thereof having DNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 12.

In some embodiments, the polypeptide has been isolated. A polypeptide of the present invention preferably comprises or consists of the amino acid sequence shown in SEQ ID NO: 15 or an allelic variant thereof; or is a fragment thereof having DNase activity. In another aspect, the polypeptide comprises or consists of the mature polypeptide of SEQ ID NO: 14. In another aspect, the polypeptide comprises or consists of amino acids 1 to 192 of SEQ ID NO: 14.

In one embodiment, the polypeptide preferably comprises or consists of the amino acid sequence shown in SEQ ID NO: 15; comprises the amino acid sequence shown in SEQ ID NO: 15 and a N-terminal and/or C-terminal His-tag and/or HQ-tag; comprises the amino acid sequence of SEQ ID NO: 15 and a N-terminal and/or C-terminal extension of between 1 and 10 amino acids; or is a fragment thereof having DNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 15.

In some embodiments, the polypeptide has been isolated. A polypeptide of the present invention preferably comprises or consists of the amino acid sequence shown in SEQ ID NO: 15 or an allelic variant thereof; or is a fragment thereof having DNase activity. In another aspect, the polypeptide comprises or consists of the mature polypeptide of SEQ ID NO: 17. In another aspect, the polypeptide comprises or consists of amino acids 1 to 187 of SEQ ID NO: 17.

In one embodiment, the polypeptide preferably comprises or consists of the amino acid sequence shown in SEQ ID NO: 18; comprises the amino acid sequence shown in SEQ ID NO: 18 and a N-terminal and/or C-terminal His-tag and/or HQ-tag; comprises the amino acid sequence of SEQ ID NO: 18 and a N-terminal and/or C-terminal extension of between 1 and 10 amino acids; or is a fragment thereof having DNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 18.

In some embodiments, the polypeptide has been isolated. A polypeptide of the present invention preferably comprises or consists of the amino acid sequence shown in SEQ ID NO: 21 or an allelic variant thereof; or is a fragment thereof having DNase activity. In another aspect, the polypeptide comprises or consists of the mature polypeptide of SEQ ID NO: 20. In another aspect, the polypeptide comprises or consists of amino acids 1 to 187 of SEQ ID NO: 20.

In one embodiment, the polypeptide preferably comprises or consists of the amino acid sequence shown in SEQ ID NO: 21; comprises the amino acid sequence shown in SEQ ID NO: 21 and a N-terminal and/or C-terminal His-tag and/or HQ-tag; comprises the amino acid sequence of SEQ ID NO: 21 and a N-terminal and/or C-terminal extension of between 1 and 10 amino acids; or is a fragment thereof having DNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 21.

In some embodiments, the polypeptide has been isolated. A polypeptide of the present invention preferably comprises or consists of the amino acid sequence shown in SEQ ID NO: 24 or an allelic variant thereof; or is a fragment thereof having DNase activity. In another aspect, the polypeptide comprises or consists of the mature polypeptide of SEQ ID NO: 23. In another aspect, the polypeptide comprises or consists of amino acids 1 to 187 of SEQ ID NO: 23.

In one embodiment, the polypeptide preferably comprises or consists of the amino acid sequence shown in SEQ ID NO: 24; comprises the amino acid sequence shown in SEQ ID NO: 24 and a N-terminal and/or C-terminal His-tag and/or HQ-tag; comprises the amino acid sequence of SEQ ID NO: 24 and a N-terminal and/or C-terminal extension of between 1 and 10 amino acids; or is a fragment thereof having DNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 24.

In some embodiments, the polypeptide has been isolated. A polypeptide of the present invention preferably comprises or consists of the amino acid sequence shown in SEQ ID NO: 27 or an allelic variant thereof; or is a fragment thereof having DNase activity. In another aspect, the polypeptide comprises or consists of the mature polypeptide of SEQ ID NO: 26. In another aspect, the polypeptide comprises or consists of amino acids 1 to 187 of SEQ ID NO: 26.

In one embodiment, the polypeptide preferably comprises or consists of the amino acid sequence shown in SEQ ID NO: 27; comprises the amino acid sequence shown in SEQ ID NO: 27 and a N-terminal and/or C-terminal His-tag and/or HQ-tag; comprises the amino acid sequence of SEQ ID NO: 27 and a N-terminal and/or C-terminal extension of between 1 and 10 amino acids; or is a fragment thereof having DNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 27.

In some embodiments, the polypeptide has been isolated. A polypeptide of the present invention preferably comprises or consists of the amino acid sequence shown in SEQ ID NO: 30 or an allelic variant thereof; or is a fragment thereof having DNase activity. In another aspect, the polypeptide comprises or consists of the mature polypeptide of SEQ ID NO: 29. In another aspect, the polypeptide comprises or consists of amino acids 1 to 187 of SEQ ID NO: 29.

In one embodiment, the polypeptide preferably comprises or consists of the amino acid sequence shown in SEQ ID NO: 30; comprises the amino acid sequence shown in SEQ ID NO: 30 and a N-terminal and/or C-terminal His-tag and/or HQ-tag; comprises the amino acid sequence of SEQ ID NO: 30 and a N-terminal and/or C-terminal extension of between 1 and 10 amino acids; or is a fragment thereof having DNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 30.

In some embodiments, the polypeptide has been isolated. A polypeptide of the present invention preferably comprises or consists of the amino acid sequence shown in SEQ ID NO: 33 or an allelic variant thereof; or is a fragment thereof having DNase activity. In another aspect, the polypeptide comprises or consists of the mature polypeptide of SEQ ID NO: 32. In another aspect, the polypeptide comprises or consists of amino acids 1 to 188 of SEQ ID NO: 32.

In one embodiment, the polypeptide preferably comprises or consists of the amino acid sequence shown in SEQ ID NO: 33; comprises the amino acid sequence shown in SEQ ID NO: 33 and a N-terminal and/or C-terminal His-tag and/or HQ-tag; comprises the amino acid sequence of SEQ ID NO: 33 and a N-terminal and/or C-terminal extension of between 1 and 10 amino acids; or is a fragment thereof having DNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 33.

In some embodiments, the polypeptide has been isolated. A polypeptide of the present invention preferably comprises or consists of the amino acid sequence shown in SEQ ID NO: 36 or an allelic variant thereof; or is a fragment thereof having DNase activity. In another aspect, the polypeptide comprises or consists of the mature polypeptide of SEQ ID NO: 35. In another aspect, the polypeptide comprises or consists of amino acids 1 to 188 of SEQ ID NO: 35.

In one embodiment, the polypeptide preferably comprises or consists of the amino acid sequence shown in SEQ ID NO: 36; comprises the amino acid sequence shown in SEQ ID NO: 36 and a N-terminal and/or C-terminal His-tag and/or HQ-tag; comprises the amino acid sequence of SEQ ID NO: 36 and a N-terminal and/or C-terminal extension of between 1 and 10 amino acids; or is a fragment thereof having DNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 36.

In some embodiments, the polypeptide has been isolated. A polypeptide of the present invention preferably comprises or consists of the amino acid sequence shown in SEQ ID NO: 39 or an allelic variant thereof; or is a fragment thereof having DNase activity. In another aspect, the polypeptide comprises or consists of the mature polypeptide of SEQ ID NO: 38. In another aspect, the polypeptide comprises or consists of amino acids 1 to 188 of SEQ ID NO: 38.

In one embodiment, the polypeptide preferably comprises or consists of the amino acid sequence shown in SEQ ID NO: 39; comprises the amino acid sequence shown in SEQ ID NO: 39 and a N-terminal and/or C-terminal His-tag and/or HQ-tag; comprises the amino acid sequence of SEQ ID NO: 39 and a N-terminal and/or C-terminal extension of between 1 and 10 amino acids; or is a fragment thereof having DNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 39.

In some embodiments, the polypeptide has been isolated. A polypeptide of the present invention preferably comprises or consists of the amino acid sequence shown in SEQ ID NO: 42 or an allelic variant thereof; or is a fragment thereof having DNase activity. In another aspect, the polypeptide comprises or consists of the mature polypeptide of SEQ ID NO: 41. In another aspect, the polypeptide comprises or consists of amino acids 1 to 188 of SEQ ID NO: 41.

In one embodiment, the polypeptide preferably comprises or consists of the amino acid sequence shown in SEQ ID NO: 42; comprises the amino acid sequence shown in SEQ ID NO: 42 and a N-terminal and/or C-terminal His-tag and/or HQ-tag; comprises the amino acid sequence of SEQ ID NO: 42 and a N-terminal and/or C-terminal extension of between 1 and 10 amino acids; or is a fragment thereof having DNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 42.

In some embodiments, the present invention relates to variants of the mature polypeptide shown in SEQ ID NO: 3 comprising a substitution, deletion, and/or insertion at one or more (e.g., several) positions. In some embodiments, the number of amino acid substitutions, deletions and/or insertions introduced into the mature polypeptide shown in SEQ ID NO: 3 is up to 10, e.g., 1, 2, 3, 4, 5, 6, 7, 8, 9, or 10.

In one embodiment, the present invention relates to variants of the mature polypeptide shown in SEQ ID NO: 6 comprising a substitution, deletion, and/or insertion at one or more (e.g., several) positions. In some embodiments, the number of amino acid substitutions, deletions and/or insertions introduced into the mature polypeptide shown in SEQ ID NO: 6 is up to 10, e.g., 1, 2, 3, 4, 5, 6, 7, 8, 9, or 10.

In one embodiment, the present invention relates to variants of the mature polypeptide shown in SEQ ID NO: 9 comprising a substitution, deletion, and/or insertion at one or more (e.g., several) positions. In some embodiments, the number of amino acid substitutions, deletions and/or insertions introduced into the mature polypeptide shown in SEQ ID NO: 9 is up to 10, e.g., 1, 2, 3, 4, 5, 6, 7, 8, 9, or 10.

In one embodiment, the present invention relates to variants of the mature polypeptide shown in SEQ ID NO: 12 comprising a substitution, deletion, and/or insertion at one or more (e.g., several) positions. In some embodiments, the number of amino acid substitutions, deletions and/or insertions introduced into the mature polypeptide shown in SEQ ID NO: 12 is up to 10, e.g., 1, 2, 3, 4, 5, 6, 7, 8, 9, or 10.

In one embodiment, the present invention relates to variants of the mature polypeptide shown in SEQ ID NO: 15 comprising a substitution, deletion, and/or insertion at one or more (e.g., several) positions. In some embodiments, the number of amino acid substitutions, deletions and/or insertions introduced into the mature polypeptide shown in SEQ ID NO: 15 is up to 10, e.g., 1, 2, 3, 4, 5, 6, 7, 8, 9, or 10.

In one embodiment, the present invention relates to variants of the mature polypeptide shown in SEQ ID NO: 18 comprising a substitution, deletion, and/or insertion at one or more (e.g., several) positions. In some embodiments, the number of amino acid substitutions, deletions and/or insertions introduced into the mature polypeptide shown in SEQ ID NO: 18 is up to 10, e.g., 1, 2, 3, 4, 5, 6, 7, 8, 9, or 10.

In one embodiment, the present invention relates to variants of the mature polypeptide shown in SEQ ID NO: 21 comprising a substitution, deletion, and/or insertion at one or more (e.g., several) positions. In some embodiments, the number of amino acid substitutions, deletions and/or insertions introduced into the mature polypeptide shown in SEQ ID NO: 21 is up to 10, e.g., 1, 2, 3, 4, 5, 6, 7, 8, 9, or 10.

In one embodiment, the present invention relates to variants of the mature polypeptide shown in SEQ ID NO: 24 comprising a substitution, deletion, and/or insertion at one or more (e.g., several) positions. In some embodiments, the number of amino acid substitutions, deletions and/or insertions introduced into the mature polypeptide shown in SEQ ID NO: 24 is up to 10, e.g., 1, 2, 3, 4, 5, 6, 7, 8, 9, or 10.

In one embodiment, the present invention relates to variants of the mature polypeptide shown in SEQ ID NO: 27 comprising a substitution, deletion, and/or insertion at one or more (e.g., several) positions. In some embodiments, the number of amino acid substitutions, deletions and/or insertions introduced into the mature polypeptide shown in SEQ ID NO: 27 is up to 10, e.g., 1, 2, 3, 4, 5, 6, 7, 8, 9, or 10.

In one embodiment, the present invention relates to variants of the mature polypeptide shown in SEQ ID NO: 30 comprising a substitution, deletion, and/or insertion at one or more (e.g., several) positions. In some embodiments, the number of amino acid substitutions, deletions and/or insertions introduced into the mature polypeptide shown in SEQ ID NO: 30 is up to 10, e.g., 1, 2, 3, 4, 5, 6, 7, 8, 9, or 10.

In one embodiment, the present invention relates to variants of the mature polypeptide shown in SEQ ID NO: 33 comprising a substitution, deletion, and/or insertion at one or more (e.g., several) positions. In some embodiments, the number of amino acid substitutions, deletions and/or insertions introduced into the mature polypeptide shown in SEQ ID NO: 33 is up to 10, e.g., 1, 2, 3, 4, 5, 6, 7, 8, 9, or 10.

In one embodiment, the present invention relates to variants of the mature polypeptide shown in SEQ ID NO: 36 comprising a substitution, deletion, and/or insertion at one or more (e.g., several) positions. In some embodiments, the number of amino acid substitutions, deletions and/or insertions introduced into the mature polypeptide shown in SEQ ID NO: 36 is up to 10, e.g., 1, 2, 3, 4, 5, 6, 7, 8, 9, or 10.

In one embodiment, the present invention relates to variants of the mature polypeptide shown in SEQ ID NO: 39 comprising a substitution, deletion, and/or insertion at one or more (e.g., several) positions. In some embodiments, the number of amino acid substitutions, deletions and/or insertions introduced into the mature polypeptide shown in SEQ ID NO: 39 is up to 10, e.g., 1, 2, 3, 4, 5, 6, 7, 8, 9, or 10.

In one embodiment, the present invention relates to variants of the mature polypeptide shown in SEQ ID NO: 42 comprising a substitution, deletion, and/or insertion at one or more (e.g., several) positions. In some embodiments, the number of amino acid substitutions, deletions and/or insertions introduced into the mature polypeptide shown in SEQ ID NO: 42 is up to 10, e.g., 1, 2, 3, 4, 5, 6, 7, 8, 9, or 10.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant molecules are tested for DNase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having DNase Activity

A polypeptide having DNase activity of the present invention may be obtained from microorganisms of any genus but is preferably obtained from a genus belonging to the order Pezizales. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

In one aspect, the polypeptide is a *Ascobolus* polypeptide, e.g., a polypeptide obtained from *Ascobolus stictoideus* or *Ascobolus* sp. ZY179.

In one aspect, the polypeptide is a *Umula* polypeptide, e.g., a polypeptide obtained from *Umula* sp-56769.

In one aspect, the polypeptide is a *Morchella* polypeptide, e.g., a polypeptide obtained from *Morchella costata*, *Morchella esculenta* or *Morchella crassipes*.

In one aspect, the polypeptide is a Trichobolus polypeptide, e.g., a polypeptide obtained from *Trichobolus zukalii*.

In one aspect, the polypeptide is a *Trichophaea* polypeptide, e.g., a polypeptide obtained from *Trichophaea saccata*, *Trichophaea minuta* or *Trichophaea abundans*.

In one aspect, the polypeptide is a *Pseudoplectania* polypeptide, e.g., a polypeptide obtained from *Pseudoplectania nigrella*.

In one aspect, the polypeptide is a *Gyromitra* polypeptide, e.g., a polypeptide obtained from *Gyromitra esculenta*.

In one aspect, the polypeptide is a *Disciotis* polypeptide, e.g., a polypeptide obtained from *Disciotis venosa*.

In one aspect, the polypeptide is a *Pseudoplectania* polypeptide, e.g., a polypeptide obtained from *Pseudoplectania nigrella*.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to polynucleotides encoding a polypeptide of the present invention, as described herein. In some embodiments, the polynucleotide encoding the polypeptide of the present invention has been isolated.

One embodiment of the invention relates to a polypeptide encoded by a polynucleotide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO: 1, SEQ ID NO: 4, SEQ ID NO: 7, SEQ ID NO: 10, SEQ ID NO: 13, SEQ ID NO: 16, SEQ ID NO: 19, SEQ ID NO: 22, SEQ ID NO: 25, SEQ ID NO: 28, SEQ ID NO: 31, SEQ ID NO: 34, SEQ ID NO: 37 or SEQ ID NO: 40.

In one embodiment, the present invention relates to a polynucleotide encoding a polypeptide having DNase activity, wherein the polynucleotide having a sequence identity to the mature polypeptide coding sequence of SEQ ID NO: 1 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having DNase activity, wherein the polynucleotide having a sequence identity to the mature polypeptide coding sequence of SEQ ID NO: 4 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having DNase activity, wherein the polynucleotide having a sequence identity to the mature polypeptide coding sequence of SEQ ID NO: 7 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having DNase activity, wherein the polynucleotide having a sequence identity to the mature polypeptide coding sequence of SEQ ID NO: 10 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having DNase activity, wherein the polynucleotide having a sequence identity to the mature polypeptide coding sequence of SEQ ID NO: 13 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having DNase activity, wherein the polynucleotide having a sequence identity to the mature polypeptide coding sequence of SEQ ID NO: 16 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having DNase activity, wherein the polynucleotide having a sequence identity to the mature polypeptide coding sequence of SEQ ID NO: 19 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having DNase activity, wherein the polynucleotide having a sequence identity to the mature polypeptide coding sequence of SEQ ID NO: 22 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having DNase activity, wherein the polynucleotide having a sequence identity to the mature polypeptide coding sequence of SEQ ID NO: 25 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having DNase activity, wherein the polynucleotide having a sequence identity to the mature polypeptide coding sequence of SEQ ID NO: 28 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having DNase activity, wherein the polynucleotide having a sequence identity to the mature polypeptide coding sequence of SEQ ID NO: 31 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having DNase activity, wherein the polynucleotide having a sequence identity to the mature polypeptide coding sequence of SEQ ID NO: 34 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having DNase activity, wherein the polynucleotide having a sequence identity to the mature polypeptide coding sequence of SEQ ID NO: 37 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having DNase activity, wherein the polynucleotide having a sequence identity to the mature polypeptide coding sequence of SEQ ID NO: 40 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

The techniques used to isolate or clone a polynucleotide are known in the art and include isolation from genomic DNA or cDNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences. The control sequence may be heterologous to the host cell The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including variant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, Molecular Microbiology 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus* nigeracid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and variant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIA gene (WO 94/25612) and a *Bacillus subtilis* SP82 gene (Hue et al., 1995, Journal of Bacteriology 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCI B 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences, which may be heterologous to each other, may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMß1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. The control sequence(s) may be heterologous to the host cell. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus,* and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella,* and *Ureaplasma.*

The bacterial host cell may be any *Bacillus* cell including, but not limited to, *Bacillus alkalophilus, Bacillus altitudinis, Bacillus amyloliquefaciens, B. amyloliquefaciens* subsp. *plantarum, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus methylotrophicus, Bacillus pumilus, Bacillus safensis, Bacillus stearothermophilus, Bacillus subtilis,* and *Bacillus thuringiensis* cells.

The bacterial host cell may also be any *Streptococcus* cell including, but not limited to, *Streptococcus equisimilis, Streptococcus pyogenes, Streptococcus uberis,* and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus,* and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, Biotechniques 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell. The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, Ainsworth and Bisby's Dictionary of The Fungi, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series No. 9,* 1980).

The yeast host cell may be a *Candida, Hansenula, Kluyveromyces, Pichia, Saccharomyces, Schizosaccharomyces,* or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium*

*graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally, (b) recovering the polypeptide.

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides having DNase activity. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification,* Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In some embodiments, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may, for example, be produced by a method described in WO 90/15861 or WO 2010/096673.

Enzyme Compositions

The invention relates to compositions comprising a DNase of the present invention in combination with one or more additional component(s). The choice of additional components is within the skill of the artisan and includes conventional ingredients, including the exemplary non-limiting components set forth below.

One embodiment of the invention relates to a composition comprising:
a) at least 0.001 ppm of at least one polypeptide having DNase activity, wherein the DNase is selected for the group consisting of: SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42 and polypeptides having at least 80% sequence identity hereto;
b) one or more adjunct ingredient.

One embodiment of the invention relates to a cleaning composition comprising:
a) at least 0.001 ppm of at least one polypeptide having DNase activity, wherein the DNase is selected for the group consisting of: SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42 and polypeptides having at least 80% sequence identity hereto;
b) one or more cleaning composition component, preferably selected from surfactants, builders, bleach components, polymers, dispersing agents and additional enzymes.

The choice of cleaning components may include, for textile care, the consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

Surfactants

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and may include any conventional surfactant(s) known in the art.

When included therein the detergent will usually contain from about 1% to about 40% by weight of an anionic surfactant, such as from about 5% to about 30%, including from about 5% to about 15%, or from about 15% to about 20%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

When included therein the detergent will usually contain from about 1% to about 40% by weigh of a cationic surfactant, for example from about 0.5% to about 30%, in particular from about 1% to about 20%, from about 3% to about 10%, such as from about 3% to about 5%, from about 8% to about 12% or from about 10% to about 12%. Non-limiting examples of cationic surfactants include alkyldimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, ester quats, and combinations thereof.

When included therein the detergent will usually contain from about 0.2% to about 40% by weight of a nonionic surfactant, for example from about 0.5% to about 30%, in particular from about 1% to about 20%, from about 3% to about 10%, such as from about 3% to about 5%, from about 8% to about 12%, or from about 10% to about 12%. Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof.

When included therein the detergent will usually contain from about 0.1% to about 10% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, and combinations thereof.

When included therein the detergent will usually contain from about 0.1% to about 10% by weight of a zwitterionic surfactant. Non-limiting examples of zwitterionic surfactants include betaines such as alkyldimethylbetaines, sulfobetaines, and combinations thereof.

Builders and Co-Builders

The detergent composition may contain about 0-65% by weight, such as about 5% to about 50% of a detergent builder or co-builder, or a mixture thereof. In a dish wash detergent, the level of builder is typically 40-65%, particularly 50-65%. The builder and/or co-builder may particularly be a chelating agent that forms water-soluble complexes with Ca and Mg. Any builder and/or co-builder known in the art for use in cleaning detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as 2,2'-iminodiethan-1-ol), triethanolamine (TEA, also known as 2,2',2"-nitrilotriethan-1-01), and (carboxymethyl)inulin (CMI), and combinations thereof.

The detergent composition may also contain 0-50% by weight, such as about 5% to about 30%, of a detergent co-builder. The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra(methylenephosphonic acid) (ED™ PA), diethylenetriaminepentakis(methylenephosphonic acid) (DTMPA or DTPMPA), N-(2-hydroxyethyl)iminodiacetic acid (EDG), aspartic acid-N-monoacetic acid (ASMA), aspartic acid-N, N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MI DA), α-alanine-N, N-diacetic acid (α-ALDA), serine-N, N-diacetic acid (SEDA), isoserine-N, N-diacetic acid (ISDA), phenylalanine-N,N-diacetic acid (PHDA), anthranilic acid-N, N-diacetic acid (ANDA), sulfanilic acid-N,N-diacetic acid (SLDA), taurine-N,N-diacetic acid (TUDA) and sulfomethyl-N,N-diacetic acid (SM DA), N-(2-hydroxyethyl)ethylenediamine-N,N',N"-triacetic acid (HEDTA), diethanolglycine (DEG), diethylenetriamine penta(methylenephosphonic acid) (DTPMP), aminotris(methylenephosphonic acid) (ATMP), and combinations and salts thereof. Further exemplary builders and/or co-builders are described in, e.g., WO 09/102854, U.S. Pat. No. 5,977,053

Bleaching Systems

The detergent may contain 0-30% by weight, such as about 1% to about 20%, of a bleaching system. Any bleaching system comprising components known in the art for use in cleaning detergents may be utilized. Suitable bleaching system components include sources of hydrogen peroxide; sources of peracids; and bleach catalysts or boosters.

Sources of Hydrogen Peroxide:

Suitable sources of hydrogen peroxide are inorganic persalts, including alkali metal salts such as sodium percarbonate and sodium perborates (usually mono- or tetrahydrate), and hydrogen peroxide–urea (1/1).

Sources of Peracids:

Peracids may be (a) incorporated directly as preformed peracids or (b) formed in situ in the wash liquor from hydrogen peroxide and a bleach activator (perhydrolysis) or (c) formed in situ in the wash liquor from hydrogen peroxide and a perhydrolase and a suitable substrate for the latter, e.g., an ester.

a) Suitable preformed peracids include, but are not limited to, peroxycarboxylic acids such as peroxybenzoic acid and its ring-substituted derivatives, peroxy-α-naphthoic acid, peroxyphthalic acid, peroxylauric acid, peroxystearic acid, ε-phthalimidoperoxycaproic acid [phthalimidoperoxyhexanoic acid (PAP)], and o-carboxybenzamidoperoxycaproic acid; aliphatic and aromatic diperoxydicarboxylic acids such as diperoxydodecanedioic acid, diperoxyazelaic acid, diperoxysebacic acid, diperoxybrassylic acid, 2-decyldiperoxybutanedioic acid, and diperoxyphthalic, -isophthalic and -terephthalic acids; perimidic acids; peroxymonosulfuric acid; peroxydisulfuric acid; peroxyphosphoric acid; peroxysilicic acid; and mixtures of said compounds. It is understood that the peracids mentioned may in some cases be best added as suitable salts, such as alkali metal salts (e.g., Oxone®) or alkaline earth-metal salts.

b) Suitable bleach activators include those belonging to the class of esters, amides, imides, nitriles or anhydrides and, where applicable, salts thereof. Suitable examples are tetraacetylethylenediamine (TAED), sodium 4-[(3,5,5-trimethylhexanoyl)oxy]benzene-1-sulfonate (ISONOBS), sodium 4-(dodecanoyloxy)benzene-1-sulfonate (LOBS), sodium 4-(decanoyloxy)benzene-1-sulfonate, 4-(decanoyloxy)benzoic acid (DOBA), sodium 4-(nonanoyloxy)benzene-1-sulfonate (NOBS), and/or those disclosed in WO98/17767. A particular family of bleach activators of interest was disclosed in EP624154 and particularly preferred in that family is acetyl triethyl citrate (ATC). ATC or a short chain triglyceride like triacetin has the advantage that they are environmentally friendly. Furthermore, acetyl triethyl citrate and triacetin have good hydrolytical stability in the product upon storage and are efficient bleach activators. Finally, ATC is multifunctional, as the citrate released in the perhydrolysis reaction may function as a builder.

Bleach Catalysts and Boosters

The bleaching system may also include a bleach catalyst or booster.

Some non-limiting examples of bleach catalysts that may be used in the compositions of the present invention include manganese oxalate, manganese acetate, manganese-collagen, cobalt-amine catalysts and manganese triazacyclononane (MnTACN) catalysts; particularly preferred are complexes of manganese with 1,4,7-trimethyl-1,4,7-triazacyclononane (Me3-TACN) or 1,2,4,7-tetramethyl-1,4,7-triazacyclononane (Me4-TACN), in particular Me3-TACN, such as the dinuclear manganese complex [(Me3-TACN)Mn(O)3Mn(Me3-TACN)](PF6)2, and [2,2',2"-nitrilotris(ethane-1,2-diylazanylylidene-κN-methanylylidene)triphenolato-κ3O]manganese(III). The bleach catalysts may also be other metal compounds; such as iron or cobalt complexes.

In some embodiments, where a source of a peracid is included, an organic bleach catalyst or bleach booster may be used having one of the following formulae:

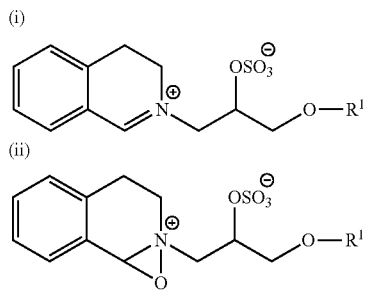

(iii) and mixtures thereof; wherein each R1 is independently a branched alkyl group containing from 9 to 24 carbons or linear alkyl group containing from 11 to 24 carbons, preferably each R1 is independently a branched alkyl group containing from 9 to 18 carbons or linear alkyl group containing from 11 to 18 carbons, more preferably each R1 is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl.

Other exemplary bleaching systems are described, e.g. in WO2007/087258, WO2007/087244, WO2007/087259, EP1867708 (Vitamin K) and WO2007/087242. Suitable photobleaches may for example be sulfonated zinc or aluminium phthalocyanines.

Metal Care Agents

Metal care agents may prevent or reduce the tarnishing, corrosion or oxidation of metals, including aluminium, stainless steel and non-ferrous metals, such as silver and copper. Suitable examples include one or more of the following:

(a) benzatriazoles, including benzotriazole or bis-benzotriazole and substituted derivatives thereof. Benzotriazole derivatives are those compounds in which the available substitution sites on the aromatic ring are partially or completely substituted. Suitable substituents include linear or branch-chain Ci-C20-alkyl groups (e.g., C1-C20-alkyl groups) and hydroxyl, thio, phenyl or halogen such as fluorine, chlorine, bromine and iodine.

(b) metal salts and complexes chosen from the group consisting of zinc, manganese, titanium, zirconium, hafnium, vanadium, cobalt, gallium and cerium salts and/or complexes, the metals being in one of the oxidation states II, III, IV, V or VI. In one aspect, suitable metal salts and/or metal complexes may be chosen from the group consisting of Mn(II) sulphate, Mn(II) citrate, Mn(II) stearate, Mn(II) acetylacetonate, K^TiF6 (e.g., K2TiF6), K^ZrF6 (e.g., K2ZrF6), CoSO4, Co(NOs)2 and Ce(NOs)3, zinc salts, for example zinc sulphate, hydrozincite or zinc acetate;

(c) silicates, including sodium or potassium silicate, sodium disilicate, sodium metasilicate, crystalline phyllosilicate and mixtures thereof.

Further suitable organic and inorganic redox-active substances that act as silver/copper corrosion inhibitors are disclosed in WO 94/26860 and WO 94/26859. Preferably the composition of the invention comprises from 0.1 to 5% by weight of the composition of a metal care agent, preferably the metal care agent is a zinc salt.

Hydrotropes

The detergent may contain 0-10% by weight, for example 0-5% by weight, such as about 0.5 to about 5%, or about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Polymers

The detergent may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or antifoaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly (ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly (oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Suitable examples include PVP-K15, PVP-K30, ChromaBond S-400, ChromaBond S-403E and Chromabond S-100 from Ashland Aqualon, and Sokalan® HP 165, Sokalan® HP 50 (Dispersing agent), Sokalan® HP 53 (Dispersing agent), Sokalan® HP 59 (Dispersing agent), Sokalan® HP 56 (dye transfer inhibitor), Sokalan® HP 66 K (dye transfer inhibitor) from BASF. Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated. Particularly preferred polymer is ethoxylated homopolymer Sokalan® HP 20 from BASF, which helps to prevent redeposition of soil in the wash liquor.

Fabric Hueing Agents

The detergent compositions of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/ reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO2007/087243.

Enzymes

The detergent additive as well as the detergent composition may comprise one or more additional enzymes such as one or more lipase, cutinase, an amylase, carbohydrase, cellulase, pectinase, mannanase, arabinase, galactanase, xylanase, oxidase, e.g., a laccase, and/or peroxidase.

In general, the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO99/001544.

Other cellulases are endo-beta-1,4-glucanase enzyme having a sequence of at least 97% identity to the amino acid sequence of position 1 to position 773 of SEQ ID NO:2 of WO 2002/099091 or a family 44 xyloglucanase, which a xyloglucanase enzyme having a sequence of at least 60% identity to positions 40-559 of SEQ ID NO: 2 of WO 2001/062903.

Commercially available cellulases include Celluzyme™, and Carezyme™ (Novozymes A/S) Carezyme Premium™ (Novozymes A/S), Celluclean™ (Novozymes A/S), Celluclean Classic™ (Novozymes A/S), Cellusoft™ (Novozymes A/S), Whitezyme™ (Novozymes A/S), Clazinase™, and Puradax HA™ (Genencor International Inc.), and KAC-500(B)™ (Kao Corporation).

Mannanases

Suitable mannanases include those of bacterial or fungal origin. Chemically or genetically modified mutants are included. The mannanase may be an alkaline mannanase of Family 5 or 26. It may be a wild-type from *Bacillus* or *Humicola*, particularly *B. agaradhaerens, B. licheniformis, B. halodurans, B. clausii*, or *H. insolens*. Suitable mannanases are described in WO 1999/064619. A commercially available mannanase is Mannaway (Novozymes A/S).

Peroxidases/Oxidases

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially available peroxidases include Guardzyme™ (Novozymes A/S).

Lipases and Cutinases:

Suitable lipases and cutinases include those of bacterial or fungal origin. Chemically modified or protein engineered mutant enzymes are included. Examples include lipase from *Thermomyces*, e.g. from *T. lanuginosus* (previously named *Humicola lanuginosa*) as described in EP258068 and EP305216, cutinase from *Humicola*, e.g. *H. insolens* (WO96/13580), lipase from strains of *Pseudomonas* (some of these now renamed to *Burkholderia*), e.g. *P. alcaligenes* or *P. pseudoalcaligenes* (EP218272), *P. cepacia* (EP331376), P. sp. strain SD705 (WO95/06720 & WO96/27002), *P. wisconsinensis* (WO96/12012), GDSL-type *Streptomyces* lipases (WO10/065455), cutinase from *Magnaporthe grisea* (WO10/107560), cutinase from *Pseudomonas mendocina* (U.S. Pat. No. 5,389,536), lipase from *Thermobifida fusca* (WO11/084412), *Geobacillus stearothermophilus* lipase (WO11/084417), lipase from *Bacillus subtilis* (WO11/084599), and lipase from *Streptomyces griseus* (WO11/150157) and *S. pristinaespiralis* (WO12/137147).

Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Preferred commercial lipase products include Lipolase™, Lipex™; Lipolex™ and Lipoclean™ (Novozymes A/S), Lumafast (originally from Genencor) and Lipomax (originally from Gist-Brocades).

Still other examples are lipases sometimes referred to as acyltransferases or perhydrolases, e.g. acyltransferases with homology to *Candida antarctica* lipase A (WO10/111143), acyltransferase from *Mycobacterium smegmatis* (WO05/56782), perhydrolases from the CE 7 family (WO09/67279), and variants of the *M. smegmatis* perhydrolase in particular the S54V variant used in the commercial product Gentle Power Bleach from Huntsman Textile Effects Pte Ltd (WO10/100028).

Amylases:

Suitable amylases include alpha-amylases and/or a glucoamylases and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase derived from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase derived from *B. amyloliquefaciens* shown in SEQ ID NO: 6 of WO 2006/066594 and residues 36-483 of SEQ ID NO: 4 are those having the substitutions:

M197T;

H156Y+A181T+N190F+A209V+Q264S; or

G48A+T49I+G107A+H156Y+A181T+N190F+I201F+A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO 96/023873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E,R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128C+K178L+T182G+Y305R+G475K;

N128C+K178L+T182G+F202Y+Y305R+D319T+G475K;

S125A+N128C+K178L+T182G+Y305R+G475K; or

S125A+N128C+T131I+T165I+K178L+T182G+Y305R+G475K wherein the variants are C-terminally truncated and optionally further comprises a substitution at position 243 and/or a deletion at position 180 and/or position 181.

Further suitable amylases are amylases having SEQ ID NO: 1 of WO13184577 or variants having 90% sequence identity to SEQ ID NO: 1 thereof. Preferred variants of SEQ ID NO: 1 are those having a substitution, a deletion or an insertion in one of more of the following positions: K176, R178, G179, T180, G181, E187, N192, M199, I203, S241, R458, T459, D460, G476 and G477. More preferred variants of SEQ ID NO: 1 are those having the substitution in one of more of the following positions: K176L, E187P, N192FYH, M199L, I203YF, S241QADN, R458N, T459S, D460T, G476K and G477K and/or deletion in position R178 and/or S179 or of T180 and/or G181. Most preferred amylase variants of SEQ ID NO: 1 are those having the substitutions:

E187P+I203Y+G476K

E187P+I203Y+R458N+T459S+D460T+G476K wherein the variants optionally further comprise a substitution at position 241 and/or a deletion at position 178 and/or position 179.

Further suitable amylases are amylases having SEQ ID NO: 1 of WO10104675 or variants having 90% sequence identity to SEQ ID NO: 1 thereof. Preferred variants of SEQ ID NO: 1 are those having a substitution, a deletion or an insertion in one of more of the following positions: N21, D97, V128 K177, R179, S180, I181, G182, M200, L204, E242, G477 and G478. More preferred variants of SEQ ID NO: 1 are those having the substitution in one of more of the following positions: N21D, D97N, V128I K177L, M200L, L204YF, E242QA, G477K and G478K and/or deletion in position R179 and/or S180 or of I181 and/or G182. Most preferred amylase variants of SEQ ID NO: 1 are those having the substitutions:

N21D+D97N+V128I wherein the variants optionally further comprise a substitution at position 200 and/or a deletion at position 180 and/or position 181.

Other suitable amylases are the alpha-amylase having SEQ ID NO: 12 in WO01/66712 or a variant having at least 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO2011/098531, WO2013/001078 and WO2013/001087.

Commercially available amylases are Duramyirm, Termamyirm, Fungamyirm, Stainzyme™, Stainzyme Plus™, Natalase™, Liquozyme X and BAN™ (from Novozymes A/S), and Rapidase™, Purastar™/Effectenz™, Powerase, Preferenz S1000, Preferenz S100 and Preferenz S110 (from Genencor International Inc./DuPont).

Proteases:

Suitable proteases include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4 or other metalloprotease such as those from M5, M7 or M8 families.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those derived from Bacillus such as Bacillus lentus, B. alkalophilus, B. subtilis, B. amyloliquefaciens, Bacillus pumilus and Bacillus gibsonii described in; U.S. Pat. No. 7,262,042 and WO09/021867, and subtilisin lentus, subtilisin Novo, subtilisin Carlsberg, Bacillus licheniformis, subtilisin BPN', subtilisin 309, subtilisin 147 and subtilisin 168 described in WO89/06279 and protease PD138 described in (WO93/18140). Other useful proteases may be those described in WO 92/175177, WO 01/016285, WO 02/026024 and WO 02/016547. Examples of trypsin-like proteases are trypsin (e.g. of porcine or bovine origin) and the Fusarium protease described in WO 89/06270, WO 94/25583 and WO 05/040372, and the chymotrypsin proteases derived from Cellumonas described in WO 05/052161 and WO 05/052146.

A further preferred protease is the alkaline protease from Bacillus lentus DSM 5483, as described for example in WO 95/23221, and variants thereof which are described in WO 92/21760, WO 95/23221, EP 1921147 and EP 1921148.

Examples of metalloproteases are the neutral metalloprotease as described in WO07/044993 (Genencor Int.) such as those derived from Bacillus amyloliquefaciens.

Examples of useful proteases are the variants described in: WO 92/19729, WO 96/034946, WO 98/20115, WO 98/20116, WO 99/011768, WO 01/44452, WO 03/006602, WO 04/03186, WO 04/041979, WO 07/006305, WO 11/036263, WO 11/036264, especially the variants with substitutions in one or more of the following positions: 3, 4, 9, 15, 24, 27, 42, 55, 59, 60, 66, 74, 85, 96, 97, 98, 99, 100, 101, 102, 104, 116, 118, 121, 126, 127, 128, 154, 156, 157, 158, 161, 164, 176, 179, 182, 185, 188, 189, 193, 198, 199, 200, 203, 206, 211, 212, 216, 218, 226, 229, 230, 239, 246, 255, 256, 268 and 269 wherein the positions correspond to the positions of the Bacillus lentus protease shown in SEQ ID NO: 1 of WO 2016/001449. More preferred the subtilase variants may comprise one or more of the following mutations the mutations: S3T, V41, S9R, S9E, A15T, S24G, S24R, K27R, N42R, S55P, G59E, G59D, N60D, N60E, V66A, N74D, N85S, N85R, G96S, G96A, S97G, S97D, S97A, S97SD, S99E, S99D, S99G, S99M, S99N, S99R, S99H, S101A, V102I, V102Y, V102N, S104A, G116V, G116R, H118D, H118N, N120S, S126L, P127Q, S128A, S154D, A156E, G157D, G157P, S158E, Y161A, R164S, Q176E, N179E, S182E, Q185N, A188P, G189E, V193M, N198D, V1991, Y203W, 5206G, L211Q, L211D, N212D, N2125, M2165, A226V, K229L, Q230H, Q239R, N246K, N255W, N255D, N255E, L256E, L256D T268A, R269H. The protease variants are preferably variants of the Bacillus lentus protease (Savinase®) shown in SEQ ID NO: 1 of WO 2016/001449, the Bacillus amyloliquefaciens protease (BPN') shown in SEQ ID NO: 2 of WO2016/001449. The protease variants preferably have at least 80% sequence identity to SEQ ID NO: 1 or SEQ ID NO: 2 of WO 2016/001449.

A protease variant comprising a substitution at one or more positions corresponding to positions 171, 173, 175, 179, or 180 of SEQ ID NO: 1 of WO2004/067737, wherein said protease variant has a sequence identity of at least 75% but less than 100% to SEQ ID NO: 1 of WO 2004/067737.

Suitable commercially available protease enzymes include those sold under the trade names Alcalase®, Duralase™, Durazym$^T$m, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Blaze®, Blaze Evity® 100T, Blaze Evity® 125T, Blaze Evity® 150T, Neutrase®, Everlase® and Esperase® (Novozymes A/S), those sold under the tradename Maxatase®, Maxacal®, Maxapem®, Purafect Ox®, Purafect OxP®, Puramax®, FN2®, FN3®, FN4®, Excellase®, Excellenz P1000™, Excellenz P1250™, Eraser®, Preferenz P100™, Purafect Prime®, Preferenz P110™, Effectenz P1000™, Purafect®™, Effectenz P1050™, Purafect Ox®™, Effectenz P2000™, Purafast®, Properase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (Bacillus alkalophilus subtilisin) from Kao.

Peroxidases/Oxidases

A peroxidase according to the invention is a peroxidase enzyme comprised by the enzyme classification EC 1.11.1.7, as set out by the Nomenclature Committee of the International Union of Biochemistry and Molecular Biology (IUBMB), or any fragment derived therefrom, exhibiting peroxidase activity.

Suitable peroxidases include those of plant, bacterial or fungal origin. Chemically modified or protein engineered mutants are included. Examples of useful peroxidases include peroxidases from Coprinopsis, e.g., from C. cinerea (EP 179,486), and variants thereof as those described in WO 93/24618, WO 95/10602, and WO 98/15257.

A suitable peroxidase includes a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions. Preferably, the haloperoxidase is a vanadium haloperoxidase, i.e., a vanadate-containing haloperoxidase. Haloperoxidases have been isolated from many different fungi, in particular from the fungus group dematiaceous hyphomycetes, such as Caldariomyces, e.g., C. fumago, Alternaria, Curvularia, e.g., C. verruculosa and C. inaequalis, Drechslera, Ulocladium and Botrytis.

Haloperoxidases have also been isolated from bacteria such as Pseudomonas, e.g., P. pyrrocinia and Streptomyces, e.g., S. aureofaciens.

A suitable oxidase includes in particular, any laccase enzyme comprised by the enzyme classification EC 1.10.3.2, or any fragment derived therefrom exhibiting laccase activity, or a compound exhibiting a similar activity, such as a catechol oxidase (EC 1.10.3.1), an o-aminophenol oxidase (EC 1.10.3.4), or a bilirubin oxidase (EC 1.3.3.5). Preferred laccase enzymes are enzymes of microbial origin. The enzymes may be derived from plants, bacteria or fungi (including filamentous fungi and yeasts). Suitable examples from fungi include a laccase derivable from a strain of *Aspergillus, Neurospora,* e.g., *N. crassa, Podospora, Botrytis, Collybia, Fomes, Lentinus, Pleurotus, Trametes,* e.g., *T. villosa* and *T. versicolor, Rhizoctonia,* e.g., *R. solani, Coprinopsis,* e.g., *C. cinerea, C. comatus, C. friesii,* and *C. plicatilis, Psathyrella,* e.g., *P. condelleana, Panaeolus,* e.g., *P. papilionaceus, Myceliophthora,* e.g., *M. thermophila, Schytalidium,* e.g., *S. thermophilum, Polyporus,* e.g., *P. pinsitus, Phlebia,* e.g., *P. radiata* (WO 92/01046), or *Coriolus,* e.g., *C. hirsutus* (JP 2238885). Suitable examples from bacteria include a laccase derivable from a strain of *Bacillus*. A laccase derived from *Coprinopsis* or *Myceliophthora* is preferred; in particular, a laccase derived from *Coprinopsis cinerea,* as disclosed in WO 97/08325; or from *Myceliophthora thermophila,* as disclosed in WO 95/33836.

Dispersants

The detergent compositions of the present invention can also contain dispersants. In particular, powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents

The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Agent

The detergent compositions of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino) stilbene-2,2'-disulfonate, 4,4'-bis-(2,4-dianilino-s-triazin-6-ylamino) stilbene-2.2'-disulfonate, 4,4'-bis-(2-anilino-4-(N-methyl-N-2-hydroxy-ethylamino)-s-triazin-6-ylamino) stilbene-2,2'-disulfonate, 4,4'-bis-(4-phenyl-1,2,3-triazol-2-yl)stilbene-2,2'-disulfonate and sodium 5-(2H-naphtho[1,2-d][1,2,3]triazol-2-yl)-2-[(E)-2-phenylvinyl]benzenesulfonate.

Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins. Suitable fluorescent brightener levels include lower levels of from about 0.01, from 0.05, from about 0.1 or even from about 0.2 wt % to upper levels of 0.5 or even 0.75 wt %.

Soil Release Polymers

The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers is amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore, random graft co-polymers are suitable soil release polymers. Suitable graft co-polymers are described in more detail in WO 2007/138054, WO 2006/108856 and WO 2006/113314 (hereby incorporated by reference). Suitable polyethylene glycol polymers include random graft co-polymers comprising: (i) hydrophilic backbone comprising polyethylene glycol; and (ii) side chain(s) selected from the group consisting of: C4-C25 alkyl group, polypropylene, polybutylene, vinyl ester of a saturated C1-C6 mono-carboxylic acid, CI-C 6 alkyl ester of acrylic or methacrylic acid, and mixtures thereof. Suitable polyethylene glycol polymers have a polyethylene glycol backbone with random grafted polyvinyl acetate side chains. The average molecular weight of the polyethylene glycol backbone can be in the range of from 2,000 Da to 20,000 Da, or from 4,000 Da to 8,000 Da. The molecular weight ratio of the polyethylene glycol backbone to the polyvinyl acetate side chains can be in the range of from 1:1 to 1:5, or from 1:1.2 to 1:2. The average number of graft sites per ethylene oxide units can be less than 1, or less than 0.8, the average number of graft sites per ethylene oxide units can be in the range of from 0.5 to 0.9, or the average number of graft sites per ethylene oxide units can be in the range of from 0.1 to 0.5, or from 0.2 to 0.4. A suitable polyethylene glycol polymer is Sokalan HP22. Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents

The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Rheology Modifiers

The detergent compositions of the present invention may also include one or more rheology modifiers, structurants or thickeners, as distinct from viscosity reducing agents. The rheology modifiers are selected from the group consisting of non-polymeric crystalline, hydroxy-functional materials, polymeric rheology modifiers which impart shear thinning characteristics to the aqueous liquid matrix of a liquid detergent composition. The rheology and viscosity of the detergent can be modified and adjusted by methods known in the art, for example as shown in EP 2169040. Other suitable cleaning composition components include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Formulation of Detergent Products

The detergent composition of the invention may be in any convenient form, e.g., a bar, a homogenous tablet, a tablet having two or more layers, a pouch having one or more compartments, a regular or compact powder, a granule, a paste, a gel, or a regular, compact or concentrated liquid.

Pouches can be configured as single or multicompartments. It can be of any form, shape and material which is suitable for hold the composition, e.g. without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be of blended compositions comprising hydrolytically degradable and water soluble polymer blends such as polylactide and polyvinyl alcohol (known under the Trade reference M8630 as sold by Mono-Sol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids: US2009/0011970 A1.

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent. A liquid or gel detergent may be non-aqueous.

Granular Detergent Formulations

The composition(s) of the invention may be formulated as a granule for example as a co-granule that combines one or more enzymes. Each enzyme will then be present in more granules securing a more uniform distribution of enzymes in the detergent. This also reduces the physical segregation of different enzymes due to different particle sizes. Methods for producing multi-enzyme co-granulates for the detergent industry are disclosed in the IP.com disclosure IPCOM000200739D.

Another example of formulation of enzymes by the use of co-granulates are disclosed in WO 2013/188331, which relates to a detergent composition comprising (a) a multi-enzyme co-granule; (b) less than 10 wt zeolite (anhydrous basis); and (c) less than 10 wt phosphate salt (anhydrous basis), wherein said enzyme co-granule comprises from 10 to 98 wt % moisture sink component and the composition additionally comprises from 20 to 80 wt % detergent moisture sink component. A multi-enzyme co-granule may comprise an DNase of the invention and (a) one or more enzymes selected from lipases, cellulases, xyloglucanases, perhydrolases, peroxidases, lipoxygenases, laccases, hemicellulases, proteases, care cellulases, cellobiose dehydrogenases, xylanases, phospho lipases, esterases, cutinases, pectinases, mannanases, pectate lyases, keratinases, reductases, oxidases, phenoloxidases, ligninases, pullulanases, tannases, pentosanases, lichenases glucanases, arabinosidases, hyaluronidase, chondroitinase, amylases, and mixtures thereof.

In one aspect, the present invention provides a granule, which comprises:

(a) a core comprising a polypeptide comprising the amino acid sequence shown in SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42 or polypeptides having at least 80% sequence identity hereto, and (b) optionally a coating consisting of one or more layer(s) surrounding the core.

Uses

The polypeptides of the invention having DNase activity may be used for deep cleaning of an item, such as a textile. One embodiment of the invention relates to the use of a DNase according to the invention for prevention reduction or removal of malodor. One embodiment of the invention relates to the use of an DNase of the invention for prevention or reduction of anti-redeposition and improvement of whiteness of a textile subjected to multiple washes. One embodiment of the invention relates to the use of a polypeptide according to the invention for deep cleaning of an item, wherein the item is a textile. One embodiment of the invention relates to the use of a polypeptide according to the invention
  (i) for preventing, reducing or removing stickiness of the item;
  (ii) for pretreating stains on the item;
  (iii) for preventing, reducing or removing redeposition of soil during a wash cycle;
  (iv) for preventing, reducing or removing adherence of soil to the item;
  (v) for maintaining or improving whiteness of the item;
  (vi) for preventing, reducing or removal malodor from the item,
  wherein the item is a textile.

The invention is further summarized in the following paragraphs:

1. Use of a polypeptide having DNase activity and comprising the motif RT[TS][DN][AP][TDPS]GY (SEQ ID NO: 48) for deep cleaning of an item, wherein the item is a textile.
2. Use according to paragraph 1 for preventing, reducing or removing stickiness of the item.
3. Use according to any of paragraphs 1 or 2 for pre-treating stains on the item.
4. Use according to any of paragraphs 1-3 for preventing, reducing or removing re-deposition of soil during a wash cycle.
5. Use according to any of paragraphs 1-4 for preventing, reducing or removing adherence of soil to the item.
6. Use according to any of the preceding paragraphs for maintaining or improving the whiteness of the item.
7. Use according to any of the preceding paragraphs, wherein a malodor is reduced or removed from the item.
8. Use according to any of the preceding composition paragraphs, wherein the surface is a textile surface.
9. Use according to any of the preceding composition paragraphs, wherein the textile is made of cotton, cotton/polyester, polyester, polyamide, polyacrylic and/or silk.
10. Use according to any of the preceding paragraphs, wherein the polypeptide is a polypeptide of paragraphs 47-61
11. A composition comprising a polypeptide having DNase activity, the polypeptide comprising the motif RT[TS][DN][AP][TDPS]GY (SEQ ID NO: 48), and at least one detergent adjunct ingredient.
12. Composition according to paragraph 11, wherein the polypeptide is the polypeptide of paragraphs 45-59.
13. Composition according to any of the preceding composition paragraphs, wherein the detergent adjunct ingredient is selected from the group consisting of surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, builders and co-builders, fabric huing agents, anti-foaming agents, dispersants, processing aids, and/or pigments.
14. Composition according to any of the preceding composition paragraphs wherein the composition comprises from about 5 wt % to about 50 wt %, from about 5 wt % to about 40 wt %, from about 5 wt % to about 30 wt %, from about 5 wt % to about 20 wt %, from about 5 wt % to about 10 wt % anionic surfactant, preferably selected from linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.
15. Composition according to any of the preceding composition paragraphs wherein the composition comprises from about 10 wt % to about 50 wt % of at least one builder, preferably selected from citric acid, methylglycine-N,N-diacetic acid (MGDA) and/or glutamic acid-N,N-diacetic acid (GLDA) and mixtures thereof.
16. Composition according to any of the preceding paragraphs comprising from about 5 wt % to about 40 wt % nonionic surfactant, and from about 0 wt % to about 5 wt % anionic surfactant.
17. Composition according to paragraph 16, wherein the nonionic surfactant is selected from alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA) and combinations thereof.
18. Composition according to any of the preceding composition paragraphs, wherein the composition further comprises one or more enzymes selected from the group consisting of proteases, lipases, cutinases, amylases, carbohydrases, cellulases, pectinases, mannanases, arabinases, galactanases, xylanases and oxidases.
19. Composition according to any of the preceding composition paragraphs, wherein the composition is a bar, a homogenous tablet, a tablet having two or more layers, a pouch having one or more compartments, a regular or compact powder, a granule, a paste, a gel, or a regular, compact or concentrated liquid.
20. Composition according to any of the preceding composition paragraphs, wherein the composition is a cleaning composition selected from liquid detergent, powder detergent and granule detergent compositions.
21. Composition according to any of the preceding composition paragraphs, wherein the polypeptide comprises the motif RT[TS][DN][AP][TDPS]GY (SEQ ID NO: 48) and optionally selected is selected from the group consisting of polypeptides having the amino acid sequence shown in SEQ ID NO: 3, 6, 9, 12, 15, 18, 21, 24, 27, 30, 33, 36, 39 or 42 and polypeptides having at least 80% sequence identity hereto.
22. Composition according to any of the preceding composition paragraphs wherein the polypeptide comprises the motif RT[TS][DN][AP][TDPS]GY (SEQ ID NO: 48) and comprises the amino acid sequence shown in SEQ ID NO:

3 or a sequence having at least 60% sequence identity hereto, e.g. at least 70%, at least 80% or at least 90%.

23. Composition according to any of the preceding composition paragraphs wherein the polypeptide comprises the motif RT[TS][DN][AP][TDPS]GY (SEQ ID NO: 48) and comprises the amino acid sequence shown in SEQ ID NO: 6 or a sequence having at least 60% sequence identity hereto, e.g. at least 70%, at least 80% or at least 90%.

24. Composition according to any of the preceding composition paragraphs wherein the polypeptide comprises the motif RT[TS][DN][AP][TDPS]GY (SEQ ID NO: 48) and comprises the amino acid sequence shown in SEQ ID NO: 9 or a sequence having at least 60% sequence identity hereto, e.g. at least 70%, at least 80% or at least 90%.

25. Composition according to any of the preceding composition paragraphs wherein the polypeptide comprises the motif RT[TS][DN][AP][TDPS]GY (SEQ ID NO: 48) and comprises the amino acid sequence shown in SEQ ID NO: 12 or a sequence having at least 60% sequence identity hereto, e.g. at least 70%, at least 80% or at least 90%.

26. Composition according to any of the preceding composition paragraphs wherein the polypeptide comprises the motif RT[TS][DN][AP][TDPS]GY (SEQ ID NO: 48) and comprises the amino acid sequence shown in SEQ ID NO: 15 or a sequence having at least 60% sequence identity hereto, e.g. at least 70%, at least 80% or at least 90%.

27. Composition according to any of the preceding composition paragraphs wherein the polypeptide comprises the motif RT[TS][DN][AP][TDPS]GY (SEQ ID NO: 48) and comprises the amino acid sequence shown in SEQ ID NO: 18 or a sequence having at least 60% sequence identity hereto, e.g. at least 70%, at least 80% or at least 90%.

28. Composition according to any of the preceding composition paragraphs wherein the polypeptide comprises the motif RT[TS][DN][AP][TDPS]GY (SEQ ID NO: 48) and comprises the amino acid sequence shown in SEQ ID NO: 21 or a sequence having at least 60% sequence identity hereto, e.g. at least 70%, at least 80% or at least 90%.

29. Composition according to any of the preceding composition paragraphs wherein the polypeptide comprises the motif RT[TS][DN][AP][TDPS]GY (SEQ ID NO: 48) and comprises the amino acid sequence shown in SEQ ID NO: 24 or a sequence having at least 60% sequence identity hereto, e.g. at least 70%, at least 80% or at least 90%.

30. Composition according to any of the preceding composition paragraphs wherein the polypeptide comprises the motif RT[TS][DN][AP][TDPS]GY (SEQ ID NO: 48) and comprises the amino acid sequence shown in SEQ ID NO: 27 or a sequence having at least 60% sequence identity hereto, e.g. at least 70%, at least 80% or at least 90%.

31. Composition according to any of the preceding composition paragraphs wherein the polypeptide comprises the motif RT[TS][DN][AP][TDPS]GY (SEQ ID NO: 48) and comprises the amino acid sequence shown in SEQ ID NO: 30 or a sequence having at least 60% sequence identity hereto, e.g. at least 70%, at least 80% or at least 90%.

32. Composition according to any of the preceding composition paragraphs wherein the polypeptide comprises the motif RT[TS][DN][AP][TDPS]GY (SEQ ID NO: 48) and comprises the amino acid sequence shown in SEQ ID NO: 33 or a sequence having at least 60% sequence identity hereto.

33. Composition according to any of the preceding composition paragraphs wherein the polypeptide comprises the motif RT[TS][DN][AP][TDPS]GY (SEQ ID NO: 48) and comprises the amino acid sequence shown in SEQ ID NO: 36 or a sequence having at least 60% sequence identity hereto.

34. Composition according to any of the preceding composition paragraphs wherein the polypeptide comprises the motif RT[TS][DN][AP][TDPS]GY (SEQ ID NO: 48) and comprises the amino acid sequence shown in SEQ ID NO: 39 or a sequence having at least 60% sequence identity hereto.

35. Composition according to any of the preceding composition paragraphs wherein the polypeptide comprises the motif RT[TS][DN][AP][TDPS]GY (SEQ ID NO: 48) and comprises the amino acid sequence shown in SEQ ID NO: 42 or polypeptides having at least 60% sequence identity hereto.

36. A method for laundering an item comprising the steps of:
    a. Exposing an item to a wash liquor comprising a polypeptide of paragraphs 50-64 or a composition according to any of paragraphs 11-35;
    b. Completing at least one wash cycle; and
    c. Optionally rinsing the item,
    wherein the item is a textile.

37. A method of treating an item, wherein the item is preferably a textile e.g. a fabric, said method comprising the step of exposing an item to a polypeptide selected from the group consisting of a polypeptide having at least 80% sequence identity to the mature polypeptide of SEQ ID NO: 2, 5, 8, 11, 14, 17, 20, 23, 26, 29, 32, 35, 38 or 41; a wash liquor comprising said polypeptide or a detergent composition according to any preceding paragraph.

38. Method according to any preceding paragraph, wherein the pH of the wash liquor is in the range of 1 toll.

39. Method according to any of the preceding method paragraphs, wherein the pH of the wash liquor is in the range 5.5 to 11, such as in the range of 7 to 9, in the range of 7 to 8 or in the range of 7 to 8.5.

40. Method according to any of the preceding method paragraphs, wherein the temperature of the wash liquor is in the range of 5° C. to 95° C., or in the range of 10° C. to 80° C., in the range of 10° C. to 70° C., in the range of 10° C. to 60° C., in the range of 10° C. to 50° C., in the range of 15° C. to 40° C., in the range of 20° C. to 40° C., in the range of 15° C. to 30° C. or in the range of 20° C. to 30° C.

41. Method according to any of the preceding method paragraphs, wherein the temperature of the wash liquor is from about 20° C. to about 40° C.

42. Method according to any of the preceding method paragraphs, wherein the temperature of the wash liquor is from about 15° C. to about 30° C.

43. Method according to any of the preceding method paragraphs, wherein stains present on the item is pretreated with a polypeptide of paragraphs 50-64 or a detergent composition according to any of paragraphs 11-35.

44. Method according to any of the preceding method paragraphs, wherein stickiness of the item is reduced.

45. Method according to any of the preceding method paragraphs, wherein redeposition of soil is reduced.

46. Method according to any of the preceding method paragraphs, wherein adherence of soil to the item is reduced or removed.

47. Method according to any of the preceding method paragraphs, wherein whiteness of the item is maintained or improved.

48. Method according to any of the preceding method paragraphs, wherein malodor is reduced or removed from the item.

49. Method according to any of the preceding method paragraphs, wherein the concentration of the polypeptide having DNase activity in the wash liquor is at least 0,001 mg of polypeptide, such as at least 5 mg of protein, preferably at least 10 mg of protein, more preferably at least 15 mg of protein, per liter of wash liquor, optionally the concentration of polypeptide in the wash liquor is in the range 0,002 mg/L to 2 mg/L, such as 0.02 mg/L til 2 mg/L, such as 0.2 mg/L to 2 mg/L or in the range of 0,0001 mg/L to 10 mg/L or in the range of in the range of 0,001 mg/L to 10 mg/L, or in the range of 0.01 mg/L to 10 mg/L, or in in the range of 0.1 mg/L to 10 mg/L per liter of wash liquor, optionally the concentration of the polypeptide of the invention is 0.0001% to 2 wt %, such as 0.001 to 0.1 wt %, such as 0.005 to 0.1 wt %, such as 0.01 to 0.1 wt %, such as 0.01 to 0.5 wt % or most preferred 0.002 to 0.09 wt % in the total detergent concentration.

50. A polypeptide having DNase activity, selected from the group consisting of:
  a. a polypeptide having at least 80% sequence identity to the mature polypeptide of SEQ ID NO: 2, 5, 8, 11, 14, 17, 20, 23, 26, 29, 32, 35, 38, 41 ora polypeptide having at least 80% sequence identity to the mature polypeptide shown in SEQ ID NO: 3, 6, 9, 12, 15, 18, 21, 24, 27, 30, 33, 36, 39, 42;
  b. a polypeptide encoded by a polynucleotide that hybridizes under low stringency conditions with
    i. the mature polypeptide coding sequence of SEQ ID NO: 1, 4, 7, 10, 13, 16, 19, 22, 25, 28, 31, 34, 37, or 40;
    ii. the cDNA sequence thereof, or
    iii. the full-length complement of (i) or (ii);
  c. a polypeptide encoded by a polynucleotide having at least 60% sequence identity to the mature polypeptide coding sequence of SEQ ID NO: 1, 4, 7, 10, 13, 16, 19, 22, 25, 28, 31, 34, 37 or 40 or the cDNA sequence thereof;
  d. a variant of the mature polypeptide shown in SEQ ID NO: 23, 6, 9, 12, 15, 18, 21, 24, 27, 30, 33, 36, 39, 42 comprising a substitution, deletion, and/or insertion at one or more positions or a variant of the mature polypeptide shown in SEQ ID NO: 3, 6, 9, 12, 15, 18, 21, 24, 27, 30, 33, 36, 39, 42 comprising a substitution, deletion, and/or insertion at one or more positions; and
  e. a fragment of the polypeptide of (a), (b), (c), or (d) that comprises one or more of the motifs RT[TS][DN][AP][TDPS]GY (SEQ ID NO: 48).

51. The polypeptide of paragraph 50, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2, 5, 8, 11, 14, 17, 20, 23, 26, 29, 32, 35, 38, or 41 or to the mature polypeptide shown in SEQ ID NO: 3, 6, 9, 12, 15, 18, 21, 24, 27, 30, 33, 36, 39, 42.

52. The polypeptide of paragraph 50, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2 or to the mature polypeptide shown in SEQ ID NO: 3.

53. The polypeptide of paragraph 50, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 5 or to the mature polypeptide shown in SEQ ID NO: 6.

54. The polypeptide of paragraph 50, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 8 or to the mature polypeptide shown in SEQ ID NO: 9.

55. The polypeptide of paragraph 50, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 11 or to the mature polypeptide shown in SEQ ID NO: 12.

56. The polypeptide of paragraph 50, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 14 or to the mature polypeptide shown in SEQ ID NO: 15.

57. The polypeptide of paragraph 50, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 17 or to the mature polypeptide shown in SEQ ID NO: 18.

58. The polypeptide of paragraph 50, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 20 or to the mature polypeptide shown in SEQ ID NO: 21.

59. The polypeptide of paragraph 50, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 23 or to the mature polypeptide shown in SEQ ID NO: 24.

60. The polypeptide of paragraph 50, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 26 or to the mature polypeptide shown in SEQ ID NO: 27.

61. The polypeptide of paragraph 50, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 29 or to the mature polypeptide shown in SEQ ID NO: 30.

62. The polypeptide of paragraph 50, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 32 or to the mature polypeptide shown in SEQ ID NO: 33.
63. The polypeptide of paragraph 50, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 35 or to the mature polypeptide shown in SEQ ID NO: 36.
64. The polypeptide of paragraph 50, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 38 or to the mature polypeptide shown in SEQ ID NO: 39.
65. The polypeptide of paragraph 50, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 41 or to the mature polypeptide shown in SEQ ID NO: 42.
66. The polypeptide according to any of paragraphs 50 to 65, which is encoded by a polynucleotide that hybridizes under low stringency conditions, low-medium stringency conditions, medium stringency conditions, medium-high stringency conditions, high stringency conditions, or very high stringency conditions with
    i. the mature polypeptide coding sequence of SEQ ID NO: 1, 4, 7, 10, 13, 16, 19, 22, 25, 28, 31, 34, 37 or 40,
    ii. the cDNA sequence thereof, or
    iii. the full-length complement of (i) or (ii).
67. The polypeptide according to any of paragraphs 50-66, which is encoded by a polynucleotide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO: 1, 4, 7, 10, 13, 16, 19, 22, 25, 28, 31, 34, 37 or 40 or the cDNA sequence thereof.
68. The polypeptide according to any of paragraphs 50 to 67, comprising or consisting of SEQ ID NO: 3, 6, 9, 12, 15, 18, 21, 24, 27, 30, 33, 36, 39 or 42 or the mature polypeptide of SEQ ID NO: 2, 5, 8, 11, 14, 17, 20, 23, 26, 29, 32, 35, 38 or 41.
69. The polypeptide according to any of paragraphs 50 to 68, which is a variant of the any of the polypeptides with SEQ ID NO: 3, 6, 9, 12, 15, 18, 21, 24, 27, 30, 33, 36, 39, or 42 comprising a substitution, deletion, and/or insertion at one or more positions.
70. A polynucleotide encoding the polypeptide according to any of paragraphs 50-69.
71. A nucleic acid construct or expression vector comprising the polynucleotide of paragraph 70 operably linked to one or more optionally heterologous control sequences that direct the production of the polypeptide in an expression host.
72. A recombinant host cell comprising the polynucleotide of paragraph 70 operably linked to one or more optionally heterologous control sequences that direct the production of the polypeptide.
73. A method of producing the polypeptide of any of paragraphs 50-69, comprising cultivating a cell, which in its wild-type form produces the polypeptide, under conditions conducive for production of the polypeptide.
74. The method of paragraph 73, further comprising recovering the polypeptide.
75. A method of producing a polypeptide according to any of paragraphs 50-69, comprising cultivating the host cell of paragraph 72 under conditions conducive for production of the polypeptide.
76. The method of paragraph 75, further comprising recovering the polypeptide.
77. A nucleic acid construct or expression vector comprising a gene encoding a protein operably linked to the polynucleotide of paragraph 70, wherein the gene is foreign or heterologous to the polynucleotide encoding the signal peptide.
78. A recombinant host cell comprising a gene encoding a protein operably linked to the polynucleotide of paragraph 70, wherein the gene is foreign or heterologous to the polynucleotide encoding the signal peptide.
79. A method of producing a protein, comprising cultivating a recombinant host cell comprising a gene encoding a protein operably linked to the polynucleotide of paragraph 70, wherein the gene is foreign to the polynucleotide encoding the signal peptide, under conditions conducive for production of the protein.
80. The method of paragraph 79, further comprising recovering the protein.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

EXAMPLES

Assay I
Testing of DNase Activity
DNase activity may be determined on DNase Test Agar with Methyl Green (BD, Franklin Lakes, N.J., USA), which is prepared according to the manual from the supplier. Briefly, 21 g of agar is dissolved in 500 ml water and then autoclaved for 15 min at 121° C. Autoclaved agar is tempered to 48° C. in a water bath, and 20 ml of agar is poured into Petri dishes and allowed to solidify by incubation overnight at room temperature. On solidified agar plates, 5 µl of enzyme solutions are added and DNase activity is observed as colorless zones around the spotted enzyme solutions.

Assay II
DNase activity may be determined by fluorescence using a fluorescence-quenched DNA oligonucleotide probe. This probe emits a signal after nuclease degradation according to the manual from the supplier (DNase alert kit, Integrated DNA Technology, Coralville, Iowa, USA). Briefly, 5 µl of the substrate is added to 95 µl of DNase. If the signal is too high, further dilutions of DNase are performed in a suitable buffer. Kinetic curves are measured for 20 min at 22° C. using a Clariostar microplate reader (536 nm excitation, 556 nm emission).

Strains

*Escherichia coli* Top-10 strain purchased from TIANGEN (TIANGEN Biotech Co. Ltd., Beijing, China) was used to propagate our expression vector. *Aspergillus oryzae* MT3568 strain was used for heterologous expression of the gene encoding a polypeptide having homology with polypeptides with DNase activity. *A. oryzae* MT3568 is an amdS (acetamidase) disrupted gene derivative of *A. oryzae* JaL355 (WO02/40694) in which pyrG auxotrophy was restored by disrupting the *A. oryzae* acetamidase (amdS) gene with the pyrG gene.

Media

YPM medium was composed of 10 g yeast extract, 20 g Bacto-peptone, 20 g maotose, and deionised water to 1000 ml. LB plates were composed of 10 g of Bacto-tryptone, 5 g of yeast extract, 10 g of sodium chloride, 15 g of Bacto-agar, and deionised water to 1000 ml. LB medium was composed of 1 g of Bacto-tryptone, 5 g of yeast extract, and 10 g of sodium chloride, and deionised water to 1000 ml.

COVE sucrose plates were composed of 342 g of sucrose, 20 g of agar powder, 20 ml of COVE salt solution, and deionized water to 1 liter. The medium was sterilized by autoclaving at 15 psi for 15 minutes. The medium was cooled to 60° C. and 10 mM acetamide, 15 mM CsCl, Triton X-100 (50 µl/500 ml) were added.

COVE-2 plate/tube for isolation: 30 g/L sucrose, 20 ml/L COVE salt solution, 10 mM acetamide, 30 g/L noble agar (Difco, Cat#214220).

COVE salt solution was composed of 26 g of $MgSO_4.7H_2O$, 26 g of KCL, 26 g of $KH_2PO_4$, 50 ml of COVE trace metal solution, and deionised water to 1000 ml.

COVE trace metal solution was composed of 0.04 g of $Na_2B_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_4.2H_2O$, 10 g of $ZnSO_4.7H_2O$, and deionised water to 1000 ml.

Methyl green DNA test agar plates were made by suspending 42.05 g "DNase Test Agar Base w/ methyl green" (HiMedia Laboratories Pvt. Ltd., Inida) in 1000 ml distilled water and sterilized by autoclaving.

Example 1: Cloning, Expression and Fermentation of Fungal DNases

The DNases were derived from fungal strains isolated from environmental samples by standard microbiological isolation techniques. Strains were identified and taxonomy was assigned based on DNA sequencing of the ITS (Table 1).

TABLE 1

| DNA | Protein | Donor Organism name | source country |
|---|---|---|---|
| SEQ ID NO 7 | SEQ ID NO 9 | *Ascobolus* sp. ZY179 | China |

Chromosomal DNA from *Ascobolus* sp. ZY179 was isolated by QIAamp DNA Blood Mini Kit (Qiagen, Hilden, Germany). 5 µg of chromosomal DNA were sent for full genome sequencing using Illumina technology. Genome sequencing, the subsequent assembly of reads and the gene discovery (i.e. annotation of gene functions) are known to the person skilled in the art and the services can be purchased commercially.

The genome sequence was analyzed for putative DNases from the PFAM database families PF07510 (R. D. Finn et al. Nucleic Acids Research (2014), 42:D222-D230). This analysis identified one gene encoding a putative DNase which was subsequently cloned and recombinantly expressed in *Aspergillus oryzae*.

The DNase gene from *Ascobolus* sp. ZY179 was amplified by PCR from above isolated genomic DNA. The purified PCR product was cloned into the previously digested expression vector pCaHj505 by ligation with an IN-FUSION™ CF Dry-down Cloning Kit (Clontech Laboratories, Inc., Mountain View, Calif., USA) according to the manufacturer's instructions. The ligation mixture was used to transform *E. coli* TOP10 chemically competent cells (described in Strains). A correct colony containing SEQ ID NO: 7 was selected and verified by DNA sequencing (by SinoGenoMax Company Limited, Beijing, China). The SEQ ID NO: 7 comprising colony was cultivated overnight in 3 ml of LB medium supplemented with 100 µg of ampicillin per ml. Plasmid DNA was purified using a Qiagen Spin Miniprep kit (Cat. 27106) (QIAGEN GmbH, Hilden, Germany) according to the manufacturer's instructions.

Using the SignalP program v.3 (Nielsen et al., 1997, Protein Engineering 10: 1-6), the signal peptide and accordingly the mature peptide of SEQ ID NO: 9 was predicted (see sequence file).

Protoplasts of *Aspergillus oryzae* MT3568 (see strains section) were prepared according to WO95/002043. 100 µl of protoplasts were respectively mixed with 2.5-10 µg of each *Aspergillus* expression vector comprising SEQ ID NO: 7 and 250 µl of 60% PEG 4000, 10 mM $CaCl_2$, and 10 mM Tris-HCl pH7.5 and gently mixed. The mixture was incubated at 37° C. for 30 minutes and the protoplasts were spread onto COVE sucrose plates for selection. After incubation for 4-7 days at 37° C. spores of 4 transformants were inoculated into 3 ml of YPM medium. After 3 days cultivation at 30° C., the culture broths were analyzed by SDS-PAGE using Novex® 4-20% Tris-Glycine Gel (Invitrogen Corporation, Carlsbad, Calif., USA) to identify the transformant producing the largest amount of recombinant DNase with respective estimated mature peptide size. The hydrolytic activity of the DNase produced by the *Aspergillus* transformants was investigated using methyl green DNA test agar plates. 20 µl aliquots of the culture broth from the different transformants, or buffer (negative control) were distributed into punched holes with a diameter of 3 mm and incubated for 1 hour at 37° C. The plates were subsequently examined for the presence or absence of a white zone around the holes corresponding to phospholipase activity. Based on those two selection criteria, spores of the best transformant were spread on COVE-2 plates for re-isolation in order to isolate single colonies. Then a single colony was spread on a COVE-2 tube until sporulation. Spores from the best expressed transformant were cultivated in 2400 ml of YPM medium in shake flasks during 3 days at a temperature of 30° C. under 80 rpm agitation. Culture broth was harvested by filtration using a 0.2 µm filter device. The filtered fermentation broth was used for enzyme characterization.

Example 2: Purification of Recombinant DNase (SEQ ID NO: 9) by Metal Ion Affinity Chromatography (IMAC)

The culture broth harvested in example 1 was precipitated with ammonium sulfate (80% saturated). Precipitates were re-dissolved in 50 ml of 20 mM PBS pH 7.0, and then filtered through a 0.45 µm filter. The filtered crude protein solution was applied to a 50 ml self-packed Ni sepharose excel affinity column (GE Healthcare, Buckinghamshire, UK) equilibrated with 20 mM PBS pH 7.0 and 300 mM sodium chloride. Proteins were eluted with a linear 0-0.5 M imidazole gradient. Fractions were analyzed by SDS-PAGE using a Mini-PROTEAN TGX Stain-Free 4-15% Precast Gel (Bio-Rad Laboratories, CA, United States). DNase activities of fractions were assessed on BD Difco™ DNase Test Agar with Methyl Green (Becton, Dickinson and Company, New Jersey, United States) at pH 8.0, 40° C. Fractions were pooled containing recombinant protein bands and showing positive activities. Then the pooled solution was concentrated by ultrafiltration.

Example 3: Cloning, Expression and Fermentation of DNases

DNases were cloned from a variety of fungal strains that were isolated from environmental samples or obtained from culture collections and derived from the sources listed in the tables 2 and 3 below.

TABLE 2

| Strain | Source country | Mature protein |
| --- | --- | --- |
| Morchella costata | Japan | SEQ ID 12 |
| Gyromitra esculenta | Denmark | SEQ ID 33 |
| Disciotis venosa | Sweden | SEQ ID 42 |
| Morchella crassipes | Denmark | SEQ ID 39 |
| Morchella esculenta | Japan | SEQ ID 36 |
| Urnula sp-56769 | Japan | SEQ ID 6 |
| Ascobolus stictoideus | Denmark | SEQ ID 3 |
| Pseudoplectania nigrella | Denmark | SEQ ID 30 |

| Strain | Collection | Source country | Mature protein |
| --- | --- | --- | --- |
| Trichophaea saccata | CBS | England | SEQ ID 18 |
| Trichobolus zukalii | CBS | USA | SEQ ID 15 |
| Trichophaea minuta | CBS | Canada | SEQ ID 21 |
| Trichophaea minuta | CBS | Canada | SEQ ID 24 |
| Trichophaea abundans | CBS | The Netherlands | SEQ ID 27 |

CBS = CBS-KNAW Fungal Biodiversity Centre, Utrecht, The Netherlands

TABLE 3

| Strain | Collection | Source country | Mature protein |
| --- | --- | --- | --- |
| Trichophaea saccata | CBS | England | SEQ ID 18 |
| Trichobolus zukalii | CBS | USA | SEQ ID 15 |
| Trichophaea minuta | CBS | Canada | SEQ ID 21 |
| Trichophaea minuta | CBS | Canada | SEQ ID 24 |
| Trichophaea abundans | CBS | The Netherlands | SEQ ID 27 |

CBS = CBS-KNAW Fungal Biodiversity Centre, Utrecht, The Netherlands

For *Pseudoplectania nigrella*, a cDNA library of *P. nigrella* was made and a selection of cDNAs coding for secreted proteins were identified as in WO03/044049, herein incorporated by reference. One of the selected cDNAs encoded the mature peptide in SEQ ID NO: 30. For the other strains, chromosomal DNA was isolated from the strains and the full genome of each strain was sequenced, assembled and annotated by standard methods known to the person skilled in the art, or by purchasing the services commercially. The annotated genomes were searched for predicted peptides with the NUC1_A domain, and 12 putative DNases were identified. The genes encoding these putative DNases were cloned into an *Aspergillus* expression vector either by using PCR to amplify the DNase gene from genomic DNA or by purchasing a custom synthesized gene encoding the DNase. The cloning method used for each DNase is given in table 4 below.

TABLE 4

| Source strain | Cloning method | Mature protein |
| --- | --- | --- |
| Morchella costata | PCR | SEQ ID 12 |
| Trichophaea saccata | PCR | SEQ ID 18 |
| Trichobolus zukalii | PCR | SEQ ID 15 |
| Gyromitra esculenta | Synthesis | SEQ ID 33 |
| Disciotis venosa | PCR | SEQ ID 42 |
| Morchella crassipes | PCR | SEQ ID 39 |
| Morchella esculenta | PCR | SEQ ID 36 |
| Urnula sp-56769 | Synthesis | SEQ ID 6 |
| Trichophaea minuta | PCR | SEQ ID 21 |
| Trichophaea minuta | PCR | SEQ ID 24 |
| Trichophaea abundans | PCR | SEQ ID 27 |
| Ascobolus stictoideus | PCR | SEQ ID 3 |

*Aspergillus* expression vector pMStr57 is described in WO04/032648 and pDAu222 is described in WO13/024021. DNases cloned by PCR were amplified from genomic DNA with gene-specific primers that also append a Kozak translation initiation sequence "TCACC" immediately 5' of the start codon and cloned into BamHI and XhoI digested pMStr57. DNases cloned by synthesis were reverse translated with a method that preferentially utilizes codons that are used frequently in *Aspergillus oryzae*, and analyzes the resulting DNA sequences with algorithms designed to identify and remove sequence features that might hinder cloning or expression as described in WO06/066595. These DNase encoding genes were purchased from Thermo Fisher Scientific/GeneArt, Regensburg, Germany, as custom syntheses cloned into the BamHI and HindIII sites of pDAu222.

For *Pseudoplectania nigrella*, an aliquot of the original cDNA library was used to PCR amplify the open reading frame of SEQ ID NO. 28, and the open reading frame was cloned into the BamHI and HindIII sites of pDAu222. The cloned NUC1_A encoding genes were sequenced and confirmed to be identical to the corresponding genes found in the genome sequences or previously determined cDNA sequence, and transformed into the *Aspergillus oryzae* strain BECh2 (WO/039322) for the *Pseudoplectania nigrella* DNase or MT3568 (WO 11/057140) for the remaining DNases, by the methods described in Christensen et al., 1988, *Biotechnology* 6, 1419-1422 and WO 04/032648. Transformants were selected during regeneration from protoplasts based on the ability to utilize acetamide as a nitrogen source conferred by a selectable marker in the expression vectors, and were subsequently re-isolated under selection. Production of the recombinant DNases was evaluated by culturing the transformants in 96-well deep-well microtiter plates for 4 days at 30° C. in YPG medium (WO05/066338) and monitoring DNase expression by SDS-PAGE. For larger-scale production of the recombinant DNases, select transformants were cultured in 500 ml baffled flasks containing 150 ml of DAP-4C-1 medium (WO12/103350). The cultures were shaken on a rotary table at 150 RPM at for 4 days. The culture broth was subsequently separated from cellular material by passage through a 0.22 um filtration unit.

Example 4: Purification of DNAses pH of the filtered sample was adjusted to around pH 7.5 and 1.8M ammonium sulfate was added. The sample was applied to a 5 ml HiTrap™ Phenyl (HS) column on an Äkta Explorer. Prior to loading, the column had been equilibrated in 5 column volumes (CV) of 50 mM HEPES+1.8M AMS pH 7. In order to remove unbound material, the column was washed with 5 CV of 50 mM HEPES+1.8M AMS pH 7. The target protein was eluted from the column into a 10 ml loop using 50 mM HEPES+20% isopropanol pH 7. From the loop, the sample was loaded onto a desalting column (HiPrep™ 26/10 Desalting), which had been equilibrated with 3 CV of 50 mM HEPES+100 mM NaCl pH 7.0. The target protein was eluted with 50 mM HEPES+100 mM NaCl pH 7.0 and relevant fractions were selected and pooled based on the chromatogram. The flow rate was 5 ml/min.

Protein concentration in the final sample was estimated by measuring absorption at 280 nm.

Example 5: Deep Cleaning Effect of DNases

Isolating Laundry Specific Bacterial Strains

One strain of *Brevundimonas* sp. isolated from laundry was used in the present example. The *Brevundimonas* sp. was isolated during a study, where the bacterial diversity in laundry after washing at 15, 40 and 60° C., respectively, was investigated. The study was conducted on laundry collected from Danish households. For each wash, 20 g of laundry items (tea towel, towel, dish cloth, bib, T-shirt armpit, T-shirt collar, socks) in the ratio 4:3:2:2:1:1:1 was used. Washing was performed in a Laundr-O-Meter (LOM) at 15, 40 or 60° C. For washing at 15 and 40° C., Ariel Sensitive White & Color was used, whereas WFK IEC-A* model detergent was used for washing at 60° C. Ariel Sensitive White & Color was prepared by weighing out 5.1 g and adding tap water up to 1000 ml followed by stirring for 5 minutes. WFK IEC-A* model detergent (which is available from WFK Testgewebe GmbH) was prepared by weighing out 5 g and adding tap water up to 1300 ml followed by stirring for 15 min. Washing was performed for 1 hour at 15, 40 and 60° C., respectively, followed by 2 times rinsing with tap water for 20 min at 15° C.

Laundry was sampled immediately after washing at 15, 40 and 60° C., respectively. Twenty grams of laundry was added 0.9% (w/v) NaCl (1.06404; Merck, Darmstadt, Germany) with 0.5% (w/w) Tween 80 to yield a 1:10 dilution in stomacher bag. The mixture was homogenized using a Stomacher for 2 minutes at medium speed. After homogenization, ten-fold dilutions were prepared in 0.9% (w/v) NaCl. Bacteria were enumerated on Tryptone Soya Agar (TSA) (CM0129, Oxoid, Basingstoke, Hampshire, UK) incubated aerobically at 30° C. for 5-7 days. To suppress growth of yeast and moulds, 0.2% sorbic acid (359769, Sigma) and 0.1% cycloheximide (18079; Sigma) were added. Bacterial colonies were selected from countable plates and purified by restreaking twice on TSA. For long time storage, purified isolates were stored at −80° C. in TSB containing 20% (w/v) glycerol (49779; Sigma).

Preparation of Swatches with Biofilm

Swatches with biofilm of *Brevundimonas* sp. and *Micrococcus luteus* NN60909 were included in the present study. Bacteria was pre-grown on Tryptone Soya Agar (TSA) (pH 7.3) (CM0131; Oxoid Ltd, Basingstoke, UK) for 2-5 days at 30° C. From a single colony, a loop-full was transferred to 10 mL of TSB and incubated for 1 day at 30° C. with shaking (240 rpm). After propagation, cells were pelleted by centrifugation (Sigma Laboratory Centrifuge 6K15) (3000 g at 21° C. in 7 min) and resuspended in 10 mL of TSB diluted twice with water. Optical density (OD) at 600 nm was measured using a spectophometer (POLARstar Omega (BMG Labtech, Ortenberg, Germany). Fresh TSB diluted twice with water was inoculated to an $OD_{600\ nm}$ of 0.03, and 20 mL was added into a petridish (diameter 9 mm), in which a swatch (50 mm×50 mm) of either sterile cotton (WFK10A), Polyester-cotton (WFK20A) or polyester (WFK30A) was placed. After incubation (48 h at 15° C. with shaking (100 rpm), swatches were rinsed twice with 0.9% (w/v) NaCl.

Wash Experiment

Wash liquor of liquid Ariel Color&Style was prepared by weighing out and dissolving detergents in water with water hardness 15° dH. (Pigmentschmutz, 09V, wfk, Krefeld, Germany) (0.7 g/L) was added to the wash liquor, and 1000 ml was added to each TOM beaker. Two rinsed WFK10A swatches with *Brevundimonas* sp. biofilm, two rinsed WFK20A swatches with *Brevundimonas* sp. biofilm, two rinsed WFK30A swatches with *Brevundimonas* sp. biofilm, two rinsed WFK10A swatches with *Micrococcus luteus* biofilm, two rinsed WFK20A swatches with *Micrococcus luteus* biofilm, two rinsed WFK30A swatches with *Micrococcus luteus* biofilm, two sterile WFK10A swatches, two sterile WFK20A swatches and two sterile WFK30A swatches were added and washed for 35 min at 30° C. In washes where DNase was included, DNase was dosed 0.2, 0.02 or 0.002 ppm to the wash liquor. After wash, all swatches were rinsed twice in tap water and dried on filter paper over night. Color difference (L values) was measured using a Color Eye (Macbeth Color Eye 7000 reflectance spectrophotometer). The measurements were made without UV in the incident light and the L value from the CIE Lab color space was extracted.

The color difference (L value, L*) represents the darkest black at L*=0, and the brightest white at L*=100. Data is represented as Delta L values meaning the L value of the swatch washed with DNase minus the L value of swatch washed without DNase.

TABLE 5

Deep-cleaning of *Morchella costata* (SEQ ID NO 12) DNase on *Brevundimonas* sp. biofilm.

| | | Remission | | | ΔRemission | | |
|---|---|---|---|---|---|---|---|
| | Textile | 10A | 20A | 30A | 10A | 20A | 30A |
| DNase | 0 | 64 | 66 | 66 | | | |
| DNase | 0.2 ppm | 66 | 67 | 70 | 2 | 1 | 4 |
| DNase | 0.02 ppm | 67 | 70 | 69 | 3 | 4 | 3 |
| DNase | 0.002 ppm | 66 | 69 | 68 | 3 | 3 | 3 |

TABLE 6

Deep-cleaning of *Morchella costata* (SEQ ID NO 12) DNase on *Micrococcus luteus* biofilm

| | | Remission | | | ΔRemission | | |
|---|---|---|---|---|---|---|---|
| | Textile | 10A | 20A | 30A | 10A | 20A | 30A |
| DNase | 0 | 64 | 64 | 61 | | | |
| DNase | 0.2 ppm | 68 | 69 | 64 | 4 | 5 | 3 |
| DNase | 0.02 ppm | 69 | 71 | 67 | 5 | 7 | 6 |
| DNase | 0.002 ppm | 68 | 70 | 70 | 4 | 6 | 9 |

TABLE 7

Soil inhibition transfer of *Morchella costata* (SEQ ID NO 12) DNase Sterile swatches (no biofilm).

| | | Remission | | | ΔRemission | | |
|---|---|---|---|---|---|---|---|
| | Textile | 10A | 20A | 30A | 10A | 20A | 30A |
| DNase | 0 | 4 | 66 | 63 | | | |
| DNase | 0.2 ppm | 9 | 70 | 71 | 5 | 4 | 7 |

TABLE 7-continued

Soil inhibition transfer of *Morchella costata* (SEQ ID NO 12) DNase Sterile swatches (no biofilm).

|  |  | Remission | | | ΔRemission | | |
| --- | --- | --- | --- | --- | --- | --- | --- |
|  | Textile | 10A | 20A | 30A | 10A | 20A | 30A |
| DNase | 0.02 ppm | 9 | 72 | 72 | 5 | 6 | 9 |
| DNase | 0.002 ppm | 8 | 71 | 72 | 4 | 5 | 8 |

Examples 6: Wash Performance of DNases

Preparation of Biofilm Swatches

Biofilm swatches were made by growing *Brevundimonas* sp. on polyester swatches for two days. The biofilm swatches were rinsed twice in water and dried for 1 h under a flow and subsequently punched into small circles and stored at 4° C. for further use.

Washing Experiment

Biofilm swatch punctures were placed in a deep well 96 format plate. The 96 well plate was placed in a Hamilton robot and subjected to a wash simulation program using the following conditions: Shaking speed: 30 sec at 1000 rpm. Duration of wash cycle: 30 minutes with shaking; temperature 30° C.; Volume of wash liquor (total): 0.5 ml per well. (490 wash liquor+10 uL sample). For screening of wash performance of WT DNases, Model detergent A (3.3 g/L) dissolved in water hardness 15° dH was used.

Model detergent A wash liquor (100%) was prepared by dissolving 3.33 g/l of model detergent A containing 12% LAS, 11% AEO Biosoft N25-7 (NI), 5% AEOS (SLES), 6% MPG (mono propylene glycol), 3% ethanol, 3% TEA (triethanolamine), 2.75% cocoa soap, 2.75% soya soap, 2% glycerol, 2% sodium hydroxide, 2% sodium citrate, 1% sodium formiate, 0.2% DTMPA and 0.2% PCA (Propenoic acid=acrylic maleic copolymer)(all percentages are w/w (weight volume) in water with hardness 15 dH.

Soil was subsequently added to reach a concentration of 0.7 g soil/L (WFK 09V pigment soil). A 96 well plate was filled with each enzyme sample, and the program was started on the robot. DNases were tested in concentration 0.5-0.05 ppm. The blank consisted of biofilm swatches without any enzyme addition. After completion of the wash simulation cycle, the swatch punctures were removed from the wash liquor and dried on a filter paper. The dried swatch punctures were fixed on a sheet of white paper for scanning. The scanned picture was further used with the software color-analyzer. Each sample has an intensity measurement from the color analyzer software analysis that is used to calculate the delta intensity (remission), by subtracting the intensity of the blank, without enzyme. Values over 70 are visual for the human eye.

TABLE 8

Wash performance of DNases

| SEQ ID NO | Name | Intensity (with DNAse) | Intensity (without DNAse) | Delta Intensity |
| --- | --- | --- | --- | --- |
| SEQ ID NO 33 | *Gyromitra esculenta* | 380 | 288 | 92 |
| SEQ ID NO 42 | *Disciotis venosa* | 353 | 288 | 65 |
| SEQ ID NO 39 | *Morchella crassipes* | 372 | 288 | 84 |
| SEQ ID NO 36 | *Morchella esculenta* | 376 | 288 | 88 |
| SEQ ID NO 30 | *Pseudoplectania nigrella* | 372 | 288 | 84 |
| SEQ ID NO 6 | *Urnula* sp-56769 | 364 | 288 | 76 |
| SEQ ID NO 24 | *Trichophaea minuta* | 369 | 288 | 81 |
| SEQ ID NO 21 | *Trichophaea minuta* | 370 | 288 | 82 |
| SEQ ID NO 27 | *Trichophaea abundans* | 374 | 288 | 86 |
| SEQ ID NO 3 | *Ascobolus stictoideus* | 374 | 288 | 86 |
| SEQ ID NO 12 | *Morchella costata* | 356 | 258 | 98 |
| SEQ ID NO 18 | *Trichophaea saccata* | 349 | 258 | 92 |
| SEQ ID NO 15 | *Trichobolus zukalii* | 341 | 258 | 83 |

Example 7: Construction of Phylogenetic Trees

The NUC1 domain includes the polypeptides of the invention having DNase activity and comprises the NUC1_A domain as well as the clusters such as the clades.

A phylogenetic tree was constructed of polypeptide sequences containing a DUF1524 domain as defined in PFAM (PF07510, Pfam version 30.0 Finn (2016). Nucleic Acids Research, Database Issue 44:D279-D285). The phylogenetic tree was constructed from a multiple alignment of mature polypeptide sequences containing at least one DUF1524 domain. The sequences were aligned using the MUSCLE algorithm version 3.8.31 (Edgar, 2004. *Nucleic Acids Research* 32(5): 1792-1797), and the trees were constructed using FastTree version 2.1.8 (Price et al., 2010, *PloS one* 5(3)) and visualized using iTOL (Letunic & Bork, 2007. *Bioinformatics* 23(1): 127-128).

The polypeptide comprises of the DUF1524 domain comprises several motifs. One example is [E/D/H]H[I/V/L/F/M]X[P/A/S] (SEQ ID NO: 43) situated in positions corresponding to positions 95 to 99 in the DNase polypeptide from *M. costata* (SEQ ID NO: 12). H96 is a catalytic residue involved in the catalytic activity of DUF1524, and part of the HXXP motif. Another motif which may be comprised by the polypeptides of the invention is [T/D/S][G/N]PQL (SEQ ID NO: 44), where Q is involved in stabilizing the HXXP motif.

The polypeptides in DUF1524 can be separated into distinct sub-clusters. The sub-clusters are defined by one or more short sequence motifs, as well as by containing a DUF1524 domain as defined in PFAM (PF07510, Pfam version 30.0). We denoted one sub-cluster comprising the motif [F/L/Y/I]A[N/R]D[L/I/P/V][(SEQ ID NO: 45) as family NUC1. Another motif characteristic of this domain is C[D/N]T[A/R] (SEQ ID NO: 46). All polypeptide sequences containing a DUF1524 as well as the two motifs will be denoted as containing a NUC1 domain.

Generation of NUC1 a Domain

A phylogenetic tree was constructed of polypeptide sequences containing a NUC1 domain, as defined above. The phylogenetic tree was constructed from a multiple alignment of mature polypeptide sequences containing at least one NUC1 domain. The sequences were aligned using the MUSCLE algorithm version 3.8.31 (Edgar, 2004. *Nucleic Acids Research* 32(5): 1792-1797), and the tree was constructed using FastTree version 2.1.8 (Price et al., 2010, *PloS one* 5(3)) and visualized using iTOL (Letunic & Bork, 2007. *Bioinformatics* 23(1): 127-128). The polypeptides in NUC1 can be separated into at least distinct sub-clusters, one of which is denoted NUC1_A. A characteristic motif for this subgroup is the motif [DQ][IV]DH (SEQ ID NO: 47) corresponding to amino acid 93 to 96 in the reference polypeptide (SEQ ID NO: 12). The D at the position corresponding to position 93 of SEQ ID NO: 12 is predicted to be involved in binding of catalytic metal ion cofactor.

Generation of Phylogenetic Trees

A phylogenetic tree was constructed of polypeptide sequences containing a DUF1524 domain, a NUC1 domain, and a NUC1_A domain, as defined above. The phylogenetic tree was constructed from a multiple alignment of mature polypeptide sequences containing at least one NUC1_A domain. The sequences were aligned using the MUSCLE algorithm version 3.8.31 (Edgar, 2004. *Nucleic Acids Research* 32(5): 1792-1797), and the tree was constructed using FastTree version 2.1.8 (Price et al., 2010, *PloS one* 5(3)) and visualized using iTOL (Letunic & Bork, 2007, *Bioinformatics* 23(1): 127-128). The polypeptides in NUC1_A can be separated into multiple distinct sub-clusters, or clades, where we denoted the clades listed below. The distinct motifs for each clade are described in details below.

Generation of RTTDA Clade

The RTTDA clade comprises NUC1_A polypeptides of fungal origin, containing a DUF1524 domain, a NUC1 domain, and a NUC1_A domain, having DNase activity. The polypeptides of the clade comprises the motif example RT[TS][DN][AP][TDPS]GY (SEQ ID NO: 48), corresponding to positions 28 to 35 of SEQ ID NO: 12 where R and T (corresponding to position 31 and 32 of SEQ ID NO: 12) is fully conserved in RTTDA clade. An alignment of the polypeptides of the invention comprised in the clade is shown in FIG. 1. A phylogenetic tree of the RTTDA clade is shown in FIG. 2.

---

The invention claimed is:

1. An isolated polypeptide, which is of the RTTDA clade, has DNase activity, and is selected from the group consisting of:
   (a) a polypeptide having at least 80% sequence identity to the polypeptide of SEQ ID NO: 3;
   (b) a polypeptide having at least 80% sequence identity to the polypeptide of SEQ ID NO: 6;
   (c) a polypeptide having at least 80% sequence identity to the polypeptide of SEQ ID NO: 9;
   (d) a polypeptide having at least 85% sequence identity to the polypeptide of SEQ ID NO: 12;
   (e) a polypeptide having at least 80% sequence identity to the polypeptide of SEQ ID NO: 15;
   (f) a polypeptide having at least 80% sequence identity to the polypeptide of SEQ ID NO: 18;
   (g) a polypeptide having at least 80% sequence identity to the polypeptide of SEQ ID NO: 21;
   (h) a polypeptide having at least 80% sequence identity to the polypeptide of SEQ ID NO: 24;
   (i) a polypeptide having at least 80% sequence identity to the polypeptide of SEQ ID NO: 27;
   (j) a polypeptide having at least 80% sequence identity to the polypeptide of SEQ ID NO: 30;
   (k) a polypeptide having at least 80% sequence identity to the polypeptide of SEQ ID NO: 33;
   (l) a polypeptide having at least 80% sequence identity to the polypeptide of SEQ ID NO: 36;
   (m) a polypeptide having at least 80% sequence identity to the polypeptide of SEQ ID NO: 39;
   (n) a polypeptide having at least 80% sequence identity to the polypeptide of SEQ ID NO: 42;
   (o) a polypeptide comprising the polypeptide of (a) to (n) and an N-terminal and/or C-terminal His-tag and/or HQ-tag;
   (p) a polypeptide comprising the polypeptide of (a) to (n) and an N-terminal and/or C-terminal extension of between 1 and 10 amino acids; and
   (q) a fragment of the polypeptide of (a) to (n) SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39 or SEQ ID NO: 42, wherein the fragment has DNase activity and at least 90% of the length thereof.

2. The polypeptide of claim 1, which comprises the motif RT[TS][DN][AP][TDPS]GY (SEQ ID NO: 48).

3. The polypeptide of claim 1, which at least 90% sequence identity to the polypeptide shown in SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39 or SEQ ID NO: 42.

4. The polypeptide of claim 1, which is a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39 and SEQ ID NO: 42, wherein the variant has DNase activity and has at least 90% sequence identity to the polypeptide shown in SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39 or SEQ ID NO: 42.

5. The polypeptide of claim 1, which is a fragment of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39 and SEQ ID NO: 42, wherein the fragment has DNase activity and at least 90% of the length of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39 or SEQ ID NO: 42.

6. The polypeptide of claim 1, which comprises the amino acid sequence of SEQ ID NO: 3, SEQ ID NO: 6; SEQ ID NO: 9; SEQ ID NO: 12; SEQ ID NO: 15; SEQ ID NO: 18; SEQ ID NO: 21; SEQ ID NO: 24; SEQ ID NO: 27; SEQ ID NO: 30; SEQ ID NO: 33; SEQ ID NO: 36; SEQ ID NO: 39; or SEQ ID NO: 42.

7. A composition comprising the polypeptide of claim 1 and at least one detergent adjunct ingredient.

8. The composition of claim 7, wherein the composition is a cleaning or detergent composition, an automatic dish wash (ADVV) composition or a laundry composition.

9. The composition of claim 7, which is in the form of a bar, a homogenous tablet, a tablet having two or more layers, a pouch having one or more compartments, a regular or compact powder, a granule, a paste, a gel, or a regular, compact or concentrated liquid.

10. A method for laundering a textile, comprising:
  a. exposing the textile to a wash liquor comprising a polypeptide of claim 1; and
  b. completing at least one wash cycle.

11. The method of claim 10, further comprising rinsing the textile.

12. A polynucleotide encoding the polypeptide of claim 1.

13. A recombinant host cell comprising the polynucleotide of claim 12 operably linked to one or more control sequences that direct the production of the polypeptide in the recombinant host cell.

14. The recombinant host cell of claim 13, which comprises multiple copies of the polynucleotide.

15. A method of producing a polypeptide having DNase activity, comprising cultivating the recombinant host cell of claim 13 under conditions conducive for production of the polypeptide.

16. A method of producing a polypeptide having DNase activity, comprising cultivating the recombinant host cell of claim 14 under conditions conducive for production of the polypeptide.

17. The method of claim 16, further comprising recovering the polypeptide.

18. The method of claim 15, wherein the recombinant host cell is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

19. The method of claim 15, wherein the polypeptide has at least 90% sequence identity to the polypeptide shown in SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39 or SEQ ID NO: 42.

20. The method of claim 15, wherein the polypeptide has at least 95% sequence identity to the polypeptide shown in SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39 or SEQ ID NO: 42.

21. The polypeptide of claim 1, which at least 90% sequence identity to the polypeptide shown in SEQ ID NO: 12.

22. The polypeptide of claim 1, which at least 95% sequence identity to the polypeptide shown in SEQ ID NO: 12.

23. A composition comprising the polypeptide of claim 21 and at least one detergent adjunct ingredient.

24. The composition of claim 23, which is in the form of a bar, a homogenous tablet, a tablet having two or more layers, a pouch having one or more compartments, a regular or compact powder, a granule, a paste, a gel, or a regular, compact or concentrated liquid.

25. A polynucleotide encoding the polypeptide of claim 21.

26. A recombinant host cell comprising the polynucleotide of claim 25 operably linked to one or more control sequences that direct the production of the polypeptide in the recombinant host cell.

27. The recombinant host cell of claim 26, which comprises multiple copies of the polynucleotide.

28. A method of producing a polypeptide having DNase activity, comprising cultivating the recombinant host cell of claim 26 under conditions conducive for production of the polypeptide.

* * * * *

UNITED STATES PATENT AND TRADEMARK OFFICE
CERTIFICATE OF CORRECTION

PATENT NO. : 11,180,720 B2
APPLICATION NO. : 16/495147
DATED : November 23, 2021
INVENTOR(S) : Klaus Gori et al.

It is certified that error appears in the above-identified patent and that said Letters Patent is hereby corrected as shown below:

In the Claims

Please amend Claim 1 (Column 137, Line 42 – Column 138, Line 57) as follows:
1. An isolated polypeptide, which is of the RTTDA clade, has DNase activity, and is selected from the group consisting of:
    (a) a polypeptide having at least 80% sequence identity to the polypeptide of SEQ ID NO: 3;
    (b) a polypeptide having at least 80% sequence identity to the polypeptide of SEQ ID NO: 6;
    (c) a polypeptide having at least 80% sequence identity to the polypeptide of SEQ ID NO: 9;
    (d) a polypeptide having at least 85% sequence identity to the polypeptide of SEQ ID NO: 12;
    (e) a polypeptide having at least 80% sequence identity to the polypeptide of SEQ ID NO: 15;
    (f) a polypeptide having at least 80% sequence identity to the polypeptide of SEQ ID NO: 18;
    (g) a polypeptide having at least 80% sequence identity to the polypeptide of SEQ ID NO: 21;
    (h) a polypeptide having at least 80% sequence identity to the polypeptide of SEQ ID NO: 24;
    (i) a polypeptide having at least 80% sequence identity to the polypeptide of SEQ ID NO: 27;
    (j) a polypeptide having at least 80% sequence identity to the polypeptide of SEQ ID NO: 30;
    (k) a polypeptide having at least 80% sequence identity to the polypeptide of SEQ ID NO: 33;
    (l) a polypeptide having at least 80% sequence identity to the polypeptide of SEQ ID NO: 36;
    (m) a polypeptide having at least 80% sequence identity to the polypeptide of SEQ ID NO: 39;
    (n) a polypeptide having at least 80% sequence identity to the polypeptide of SEQ ID NO: 42;
    (o) a polypeptide comprising the polypeptide of (a) to (n) and an N-terminal and/or C-terminal His-tag and/or HQ-tag;
    (p) a polypeptide comprising the polypeptide of (a) to (n) and an N-terminal and/or C-terminal extension of between 1 and 10 amino acids; and
    (q) a fragment of the polypeptide of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39 or SEQ ID NO: 42, wherein the fragment has DNase activity and at least 90% of the length thereof.

Please amend Claim 8 (Column 139, Lines 30-32) as follows:

Signed and Sealed this
Thirty-first Day of May, 2022

Katherine Kelly Vidal
*Director of the United States Patent and Trademark Office*

8. The composition of claim 7, wherein the composition is a cleaning or detergent composition, an automatic dish wash (ADW) composition or a laundry composition.